(12) United States Patent
Chaudhari et al.

(10) Patent No.: US 8,318,928 B2
(45) Date of Patent: Nov. 27, 2012

(54) FUSED IMIDAZOLE CARBOXAMIDES AS TRPV3 MODULATORS

(75) Inventors: Sachin Sundarlal Chaudhari, Navi Mumbai (IN); Thomas Abraham, Navi Mumbai (IN); Ashok Bhausaheb Kadam, Maharashtra (IN); Sachin Vasantrao Dhone, Maharashtra (IN); Suresh Mahadev Kadam, Maharashtra (IN); Neelima Khairatkar-Joshi, Thane (IN); Vidya Ganapati Kattige, Thane (IN)

(73) Assignee: Glenmark Pharmaceuticals, S.A., La Chaux-de-Fonds (CH)

( * ) Notice: Subject to any disclaimer, the term of this patent is extended or adjusted under 35 U.S.C. 154(b) by 272 days.

(21) Appl. No.: 12/636,213

(22) Filed: Dec. 11, 2009

(65) Prior Publication Data

US 2010/0152192 A1    Jun. 17, 2010

Related U.S. Application Data

(60) Provisional application No. 61/141,133, filed on Dec. 29, 2008, provisional application No. 61/150,248, filed on Feb. 5, 2009, provisional application No. 61/221,615, filed on Jun. 30, 2009, provisional application No. 61/237,456, filed on Aug. 27, 2009.

(30) Foreign Application Priority Data

Dec. 15, 2008 (IN) .......................... 2610/MUM/2008
Jan. 22, 2009 (IN) ............................ 145/MUM/2009
Jun. 10, 2009 (IN) .......................... 1397/MUM/2009
Jul. 29, 2009 (IN) .......................... 1730/MUM/2009

(51) Int. Cl.
| | |
|---|---|
| *C07D 345/00* | (2006.01) |
| *C07D 517/00* | (2006.01) |
| *C07D 513/04* | (2006.01) |
| *C07D 403/00* | (2006.01) |
| *C07D 405/00* | (2006.01) |
| *C07D 409/00* | (2006.01) |
| *C07D 487/00* | (2006.01) |
| *C07D 491/00* | (2006.01) |
| *C07D 495/00* | (2006.01) |
| *C07D 513/02* | (2006.01) |
| *C07D 515/02* | (2006.01) |

(52) U.S. Cl. ............ 540/1; 544/364; 544/350; 546/121; 548/155

(58) Field of Classification Search ...... 540/1; 544/364, 544/350; 546/121; 548/155
See application file for complete search history.

(56) References Cited

U.S. PATENT DOCUMENTS

| | | |
|---|---|---|
| 4,444,770 A | 4/1984 | Meyer et al. |
| 5,204,352 A | 4/1993 | Sundberg et al. |
| 6,420,391 B1 | 7/2002 | Konishi et al. |
| 6,555,555 B1 | 4/2003 | Konishi et al. |
| 2004/0009537 A1 | 1/2004 | Roos et al. |
| 2006/0074124 A1 | 4/2006 | Napper et al. |
| 2007/0135477 A1 | 6/2007 | Berdini et al. |

FOREIGN PATENT DOCUMENTS

| | | |
|---|---|---|
| JP | 07242666 | 9/1995 |
| JP | 02105085 A2 | 4/2002 |
| WO | 2006017995 A1 | 2/2006 |
| WO | 2006065686 A2 | 6/2006 |
| WO | 2007042906 A1 | 4/2007 |
| WO | 2007056124 A2 | 5/2007 |
| WO | 2008001101 A2 | 1/2008 |
| WO | 2008001115 A2 | 1/2008 |
| WO | 2008012010 A1 | 1/2008 |
| WO | 2008114006 A1 | 9/2008 |

OTHER PUBLICATIONS

J. G. Cannon, Chapter Nineteen in Burger's Medicinal Chemistry and Drug Discovery, Fifth Edition, vol. I: Principles and Practice, Wiley-Interscience 1995, pp. 783-802).*

Hu H. Z. et al., 2-Aminoethoxydiphenyl Borate Is a Common Activator of TRPV1, TRPV2 and TRPV3, Journal Biol. Chem (2004), 279, 35741-35747.

Hu, H. Z. et al, Potentiation of TRPV3 Channel Function by Unsaturated Fatty Acids, Journal of Cellular Physiology, (2006), 208, 201-212.

Peterlin-Masic L. et al., Synthesis of New Functionalized Imidazo[2,1-b]Thiazoles and Thiazolo[3,2-a]Pyrimidines, J. Het. Chem., (2000), 37, 95-101.

Laneri, S. et at., Research on Heterocyclic Compounds—Part XXXIX, Eur. J. Med. Chem., (1998), 33, 163-170.

(Continued)

*Primary Examiner* — Marcos Sznaidman
(74) *Attorney, Agent, or Firm* — Gilman Pergament LLP; Edwards D. Pergament; Milagros A. Cepeda

(57) ABSTRACT

The present invention provides transient receptor potential vanilloid (TRPV) modulators of formula (I). In particular, compounds described herein are useful for treating or preventing diseases, conditions and/or disorders modulated by TRPV3. Also provided herein are processes for preparing compounds described herein, intermediates used in their synthesis, pharmaceutical compositions thereof, and methods for treating or preventing diseases, conditions and/or disorders modulated by TRPV3.

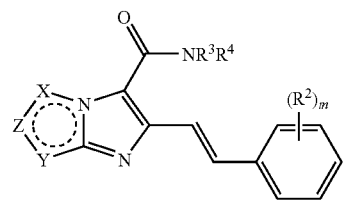

(I)

20 Claims, No Drawings

OTHER PUBLICATIONS

Nilius, B. et al., Transient Receptor Potential Cation Channels in Disease, Physiol Rev (2007), 87, 165-217.

Okuhara, D. Y. et al, Transient Receptor Potential Channels As Drug Targets, Expert Opinion on Therapeutic Targets (2007), 11, 391-401.

Cesur Z. et al., Synthesis and Antimycobacterial Activity of new Imidazo[2,1-b]Thiazole Derivatives, Eur. J. Med. Chem., (1994), 29, 981-983.

Peier, et al., A Heat-Sensitive TRP Channel Expressed in Keratinocytes, Science (2002), 296, 2046-2049.

Smith et al., TRPV3 Is a Temperature-Sensitive Vanilloid Receptor-Like Protein, Nature (2002), 418, 186-188.

Starrett J. E. et.al., Synthesis and Biological Activity of 3-Substituted Imidazo [1,2-a] Pyridines As Antiulcer Agents, J. Med. Chem., (1989), 32, 2204-2210.

Toth, A. et al., Arachidonyl Dopamine As a Ligand for the Vanilloid Receptor VR1 of the Rat, Life Sciences (2003), 73, 487-498.

Wissenbach, U. et al, TRP Channels As Potential Drug Targets, Biology of the cell (2004), 96, 47-54.

Xu et al., TRPV3 Is a Calcium-Permeable Temperature-Sensitive Cation Channel, Nature (2002), 418, 181-185.

Andreani et al., Potential Antitumor Agents, Part 291 :Synthesis and Potential Coanthracyclinic Activity of Imidazo [2,1-b] thiazole Guanylhydrazones Bioorganic & Medicinal Chemistry (2000), 8(9), 2359-2366.

Andreani et al., Dihydropyridines bearing an imidazo[2,1-b]thiazole system, European Journal of Medicinal Chemistry (1997), 32(2), 151-157.

* cited by examiner

FUSED IMIDAZOLE CARBOXAMIDES AS TRPV3 MODULATORS

RELATED APPLICATIONS

This application claims the benefit of Indian Provisional Applications 2610/MUM/2008, filed on Dec. 15, 2008; 145/MUM/2009, filed on Jan. 22, 2009; 1397/MUM/2009, filed on Jun. 10, 2009; and 1730/MUM/2009, filed on Jul. 29, 2009, and U.S. Provisional Applications 61/141,133, filed on Dec. 29, 2008; 61/150,248, filed on Feb. 5, 2009; 61/221,615, filed on Jun. 30, 2009; and 61/237,456, filed on Aug. 27, 2009; all of which are hereby incorporated by reference in their entirety.

TECHNICAL FIELD

The present patent application relates to fused imidazole carboxamides as transient receptor potential vanilloid 3 (TRPV3) activity.

BACKGROUND OF THE INVENTION

Movement of ions across cellular membranes is carried out by specialized proteins. TRP channels are one large family of non-selective cation channels that function to help regulate ion flux and membrane potential. TRP channels are subdivided into 6 sub-families including the TRPV family. TRPV3 is a member of the TRPV class of TRP channels.

TRPV3 is a calcium permeable nonselective cation channel. In addition to calcium ions, TRPV3 channels are permeable to other cations, for example sodium. Thus, TRPV3 channels modulate membrane potential by modulating the flux of cations such as calcium and sodium ions. TRPV3 receptors are mechanistically distinct from voltage-gated calcium channels. Generally, voltage-gated calcium channels respond to membrane depolarization and open to permit an influx of calcium from the extracellular medium that result in an increase in intracellular calcium levels or concentrations. In contrast, TRP channels which are non-selective, long lasting, produce more prolonged changes in ion concentration and are ligand gated (modulated by chemicals such as 2-aminoethoxydiphenyl borate [2-APB], vanilloids and heat). These mechanistic differences are accompanied by structural differences among voltage-gated and TRP channels. Thus, although many diverse channels act to regulate ion flux and membrane potential in various cell types and in response to numerous stimuli, it is important to recognize the significant structural, functional, and mechanistic differences among different classes of ion channels.

TRPV3 proteins are thermosensitive channels expressed in skin cells (Peier et al. *Science* (2002), 296, 2046-2049) and dorsal root ganglion, trigeminal ganglion, spinal cord and brain (Xu et al. *Nature* (2002), 418, 181-185; Smith et al. *Nature* (2002), 418, 186-188). In a keratinocyte cell line, stimulation of TRPV3 leads to release of inflammatory mediators including interleukin-1. Thus TRPV3 may also play an important role in regulating inflammation and pain that results from the release of inflammatory stimuli. Particular TRPV3 proteins that may be used in screening assays, as described herein, to identify compounds that modulate a function of TRPV3 include, but are not limited to human TRPV3, mouse TRPV3, rat TRPV3 and Drosophila TRPV3. US2004/0009537 (the '537 application) disclosed sequences corresponding to human, mouse, and Drosophila TRPV3. For example, SEQ ID Nos 106 and 107 of the '537 application correspond to the human nucleic acid and amino acid sequences, respectively. SEQ ID Nos 108 and 109 of the '537 application correspond to the mouse nucleic acid and amino acid sequences, respectively.

TRPV3 function has been basically implicated in the reception and transduction of pain. Accordingly, it would be desirable to identify and make compounds that can modulate one or more functions of TRPV3.

WO 2007/056124, WO 2008/140750 and WO 2008/033564 disclose TRPV3 modulators, in particular antagonists, for treatment of various diseases mediated TRPV3.

In efforts to discover better analgesics, there still exists a need for therapeutic treatment of diseases, conditions and/or disorders modulated by TRPV3.

SUMMARY OF THE INVENTION

In accordance with one aspect, the present patent application provides compounds of the formula (I):

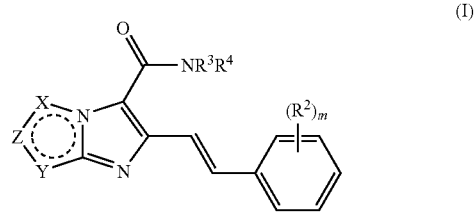

wherein the ring

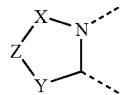

is a 5-membered or 6-membered heterocyclic or heteroaromatic ring containing one or two double bonds, in which X and Z are independently selected from —N=, and —C($R^1$)—; and Y is —O—, —S—, =N—, —N($R^1$)—, —C($R^1$)=C($R^1$)—, or —C($R^1$)=N—;
Y being —O—, —S— and —N($R^1$)— when

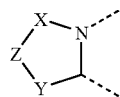

is a 5-membered ring containing one double bond; and Y being —C($R^1$)=C($R^1$)— or —C($R^1$)=N— when

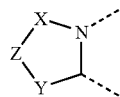

is a 6-membered ring containing two double bonds;

optionally, X and Z may be joined together to form substituted or unsubstituted 5 to 7 membered ring to result in a tricyclic core;

$R^1$, which may be same or different at each occurrence, is independently hydrogen, halogen, nitro, cyano, substituted or unsubstituted alkyl, alkenyl, haloalkyl, alkoxy, cycloalkyl, cycloalkyloxy, aryl, aryloxy, arylalkyl, heterocyclyl, or heteroaryl;

at each occurrence, R², which may be same or different, is independently selected from the group consisting of nitro, cyano, halogen, —OR, substituted or unsubstituted alkyl, alkenyl, haloalkyl, cyanoalkyl, cycloalkyl, aryl, heterocyclic ring, and heteroaryl;

R³ and R⁴, which may be same or different, are each independently hydrogen, alkali (including lithium, sodium, or potassium), substituted or unsubstituted alkyl, haloalkyl, cyanoalkyl, alkenyl, alkynyl, cycloalkyl, cycloalkenyl, aryl, heteroaryl, heterocyclyl, —S(O)NR⁵R⁶, —S(O)₂NR⁵R⁶, —S(O)R⁵ or —S(O)₂R⁵; or R³ and R⁴, together with the nitrogen atom to which they are attached, may form an optionally substituted 4 to 12 membered cyclic ring; which cyclic ring may be heterocyclyl or heteroaryl;

R is selected from hydrogen, substituted or unsubstituted alkyl, haloalkyl, cyanoalkyl, alkenyl, cycloalkyl, cycloalkylalkyl, alkoxyalkyl, aryl, heteroaryl, heterocyclic ring, arylalkyl, heteroarylalkyl, and heterocyclylalkyl;

at each occurrence, R⁵ and R⁶, which may be same or different, are independently hydrogen, substituted or unsubstituted alkyl, alkenyl, cycloalkyl, cycloalkylalkyl, cycloalkenyl, aryl, arylalkyl, heteroaryl, heteroarylalkyl, heterocyclyl, or heterocyclylalkyl; and 'm' is an integer ranging from 0 to 5, both inclusive; or pharmaceutically acceptable salt thereof.

According to one embodiment, there is provided a compound of the formula (II):

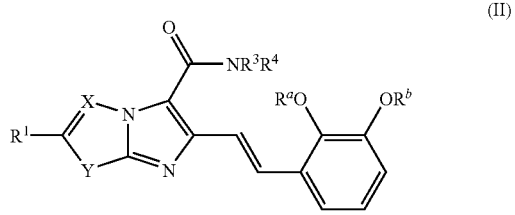

(II)

wherein X is N or CR¹; and Y is O, S, NH or NR¹;

R¹, which may be same or different at each occurrence, is independently hydrogen, halogen, hydroxy, nitro, cyano, substituted or unsubstituted alkyl, alkenyl, haloalkyl, alkoxy, cycloalkyl, cycloalkyloxy, aryl, aryloxy, arylalkyl, heterocyclyl, or heteroaryl;

R¹ and X may join together to form an optionally substituted 5 to 7 membered ring to result in a tricyclic core;

R³ and R⁴, which may be same or different, are each independently hydrogen, alkali (including lithium, sodium, or potassium), substituted or unsubstituted alkyl, haloalkyl, cyanoalkyl, alkenyl, alkynyl, cycloalkyl, cycloalkenyl, aryl, heteroaryl, heterocyclyl, —S(O)NR⁵R⁶, —S(O)₂NR⁵R⁶, or —S(O)R⁵, or —S(O)₂R⁵; or R³ and R⁴, together with the nitrogen atom to which they are attached, may form an optionally substituted 4 to 12 membered cyclic ring; which cyclic ring may be heterocyclyl or heteroaryl; and at each occurrence, R⁵ and R⁶, which may be same or different, are independently hydrogen, substituted or unsubstituted alkyl, alkenyl, cycloalkyl, cycloalkylalkyl, cycloalkenyl, aryl, arylalkyl, heteroaryl, heteroarylalkyl, heterocyclyl, or heterocyclylalkyl; and R$^a$ and R$^b$, which may be same or different, are each independently hydrogen, substituted or unsubstituted alkyl, haloalkyl, cyanoalkyl, alkenyl, cycloalkyl, cycloalkylalkyl, alkoxyalkyl, aryl, heteroaryl, heterocyclyl, arylalkyl, heteroarylalkyl, or heterocyclylalkyl;

or pharmaceutically acceptable salt thereof.

According to one embodiment, specifically provided are compounds of the formula (I) and/or (II) in which Y is S.

According to another embodiment, specifically provided are compounds of the formula (I) and/or (II) in which X is CR¹, wherein R¹ is hydrogen.

According to another embodiment, specifically provided are compounds of the formula (II) in which R$^a$ is selected from hydrogen, substituted or unsubstituted alkyl (example C₁-C₆ alkyl, preferably n-pentyl, iso-butyl, iso-pentyl, or neo-pentyl), substituted or unsubstituted haloalkyl (example difluoromethyl), substituted or unsubstituted cycloalkyl (example cyclobutyl or cyclopentyl), and substituted or unsubstituted cycloalkylalkyl (example cyclopropylmethyl or cyclobutylmethyl).

According to another embodiment, specifically provided are compounds of the formula (II) in which R$^b$ is selected from hydrogen, substituted or unsubstituted alkyl (example C₁-C₆ alkyl, preferably methyl) and substituted or unsubstituted haloalkyl (example difluoromethyl).

According to another embodiment, specifically provided are compounds of the formula (I) and/or (II) in which any one of R³ and R⁴ is hydrogen or substituted or unsubstituted alkyl (example ethyl), and the other is substituted or unsubstituted heteroaryl, preferably thiazole. In this embodiment, substituent(s) on heteroaryl is C₁-C₆ alkyl (example methyl, iso-propyl, tent-butyl), haloalkyl (example trifluoromethyl), cycloalkyl (example cyclopropyl, cyclobutyl) or 4-cyanophenyl.

According to another embodiment, specifically provided are compounds of the formula (I) and/or (II) in which any one of R³ and R⁴ is hydrogen or substituted or unsubstituted alkyl (example ethyl) and the other is substituted or unsubstituted heteroaryl, preferably thiazole. In this embodiment, two vicinal substituents on heteroaryl together with thiazole ring form optionally substituted 5 or 6-membered cyclic system in order to form bicyclic ring with including thiazole, wherein bicyclic ring is 5,6-dihydro-4H cyclopenta[1,3]thiazole or 6-fluoro-1,3-benzothiazol.

According to another embodiment, specifically provided are compounds of the formula (I) and/or (II) in which any one of R³ and R⁴ is hydrogen and other is substituted or unsubstituted aryl (e.g., phenyl), arylalkyl (e.g., benzyle), or substituted or unsubstituted heteroaryl (e.g., pyridyl, oxazole or thiadiazole). In this embodiment, substituent(s) on aryl, arylalkyl or heteroaryl may be one or more are independently selected from cyano, halogen, haloalkyl (for example trifluoromethyl), haloalkoxy (for example trifluoromethoxy).

According to another embodiment, specifically provided are compounds of the formula (I) and/or (II) in which any one of R³ and R⁴ is hydrogen and other is cyanoethyl, or substituted or unsubstituted haloalkyl (for example difluoroethyl).

According to another embodiment, specifically provided are compounds of the formula (I) and/or (II) in which R³ and R⁴ together with the nitrogen atom which they are attached to, can form an optionally substituted 6 to 12 membered cyclic ring, wherein cyclic ring is 1,2,3,4-tetrahydroquinoline, 3-trifluoromethyl-5,6,7,8-tetrahydro[1,2,4]triazolo[4,3-a]pyrazine.

According to another embodiment, specifically provided are compounds of the formula (I) and/or (II) in which R³ and R⁴ together with the nitrogen atom which they are attached to, can form an optionally substituted 6 to 8 membered piperazine ring, wherein piperazine is substituted with cyanopyridyl or 3-chloro-5-trifluoromethylpyridyl.

According to another embodiment, there is provided a compound of formula (III):

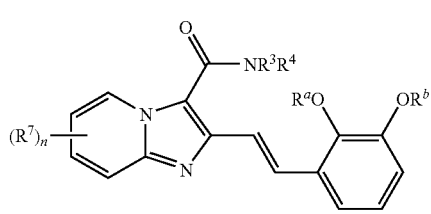

R⁷, which may be same or different at each occurrence, is halogen, hydroxy, nitro, cyano, substituted or unsubstituted alkyl, alkoxy, aryl, aryloxy, heterocyclyl, or heteroaryl;

R³ and R⁴, which may be same or different, are each independently hydrogen, alkali (including lithium, sodium, or potassium), substituted or unsubstituted alkyl, haloalkyl, cyanoalkyl, alkenyl, alkynyl, cycloalkyl, cycloalkenyl, aryl, heteroaryl, heterocyclyl, —S(O)NR⁵R⁶, —S(O)₂NR⁵R⁶, —S(O)R⁵, or —S(O)₂R⁵; or R³ and R⁴, together with the nitrogen atom to which they are attached, may form an optionally substituted 4 to 12 membered cyclic ring; which cyclic ring may be heterocyclyl or heteroaryl;

at each occurrence, R⁵ and R⁶, which may be same or different, are independently hydrogen, substituted or unsubstituted alkyl, alkenyl, cycloalkyl, cycloalkylalkyl, cycloalkenyl, aryl, arylalkyl, heteroaryl, heteroarylalkyl, heterocyclyl, or heterocyclylalkyl;

Rᵃ and Rᵇ, which may be same or different, are each independently hydrogen, substituted or unsubstituted alkyl, haloalkyl, cyanoalkyl, alkenyl, cycloalkyl, cycloalkylalkyl, alkoxyalkyl, aryl, heteroaryl, heterocyclyl, arylalkyl, heteroarylalkyl, or heterocyclylalkyl; and 'n' is an integer ranging from 0 to 4, both inclusive; or pharmaceutically acceptable salt thereof.

It should be understood that the formulas (I), (II), and (III) structurally encompasses all geometrical isomers, stereoisomers, enantiomers and diastereomers, and pharmaceutically acceptable salts that may be contemplated from the chemical structure of the genera described herein.

According to another embodiment, specifically provided are compounds of the formula (III) in which Rᵃ is hydrogen or substituted or unsubstituted, branched or unbranched alkyl (example 2,2-dimethylpropyl or 3-methylbutyl).

According to another embodiment, specifically provided are compounds of the formula (III) in which Rᵇ is hydrogen or substituted or unsubstituted alkyl, preferably methyl or difluoromethyl.

According to one embodiment, specifically provided are compounds of the formula (III) in which any one of R³ and R⁴ is hydrogen and the other is substituted or unsubstituted heteroaryl, preferably thiazole. In this embodiment the substituent(s) is haloalkyl (example trifluoromethyl) or cycloalkyl (example cyclopropyl or cyclobutyl).

According to one embodiment, specifically provided are compounds of the formula (III) in which 'n' is 0.

According to another embodiment, specifically provided are compounds of Formula I, Formula II, or Formula III, and salts thereof, that inhibit a TRPV3 function with an $IC_{50}$ value of less than 10,000 nM, or even less than 1000, 500, 250 or 100 nM. In other embodiments, specifically provided are compounds of Formula I, Formula II or Formula III or a salt thereof, that inhibits a TRPV3 function with an $IC_{50}$ value of less than 100 nM, preferably as measured via the methods described herein.

In accordance with another aspect, the present patent application provides a pharmaceutical composition that includes at least one compound of described herein and at least one pharmaceutically acceptable excipient (such as a carrier or diluent). Preferably, the pharmaceutical composition comprises a therapeutically effective amount of at least one compound described herein. The compound of the present application may be associated with a pharmaceutically acceptable excipient (such as a carrier or a diluent) or be diluted by a carrier, or enclosed within a carrier which may be in the form of a capsule, sachet, paper or other container.

The compounds and pharmaceutical compositions described herein are useful in the treatment of diseases, conditions and/or disorders modulated by TRPV3 receptors.

In accordance with another aspect, the present patent application further provides a method of treating a disease, condition and/or disorder modulated by TRPV3 receptors in a subject in need thereof by administering to the subject one or more compounds described herein in the amount effective to cause inhibition of such receptor.

Also provided herein are processes for preparing compounds described herein.

DETAILED DESCRIPTION OF THE INVENTION

The invention is defined by the claims and not limited by the description provided herein below. The terms used in the appended claims are defined herein in this glossary section, with the proviso that the claim terms may be used in a different manner if so defined by express recitation.

The terms "halogen" or "halo" means fluorine, chlorine, bromine, or iodine

The term "alkyl" refers to a hydrocarbon chain radical that includes solely carbon and hydrogen atoms in the backbone, containing no unsaturation, having from one to eight carbon atoms, and which is attached to the rest of the molecule by a single bond, e.g., methyl, ethyl, n-propyl, 1-methylethyl (isopropyl), n-butyl, n-pentyl, and 1,1-dimethylethyl (t-butyl). The term "$C_{1-6}$ alkyl" refers to an alkyl chain having 1 to 6 carbon atoms. Unless set forth or recited to the contrary, all alkyl groups described or claimed herein may be straight chain or branched, substituted or unsubstituted.

The term "alkenyl" refers to a hydrocarbon chain containing from 2 to 10 carbon atoms and including at least one carbon-carbon double bond. Non-limiting examples of alkenyl groups include ethenyl, 1-propenyl, 2-propenyl (allyl), iso-propenyl, 2-methyl-1-propenyl, 1-butenyl, and 2-butenyl. Unless set forth or recited to the contrary, all alkenyl groups described or claimed herein may be straight chain or branched, substituted or unsubstituted.

The term "alkynyl" refers to a hydrocarbyl radical having at least one carbon-carbon triple bond, and having 2 to about 12 carbon atoms (with radicals having 2 to about 10 carbon atoms being preferred). Non-limiting examples of alkynyl groups include ethynyl, propynyl, and butynyl. Unless set forth or recited to the contrary, all alkynyl groups described or claimed herein may be straight chain or branched, substituted or unsubstituted.

The term "alkoxy" denotes an alkyl group attached via an oxygen linkage to the rest of the molecule. Representative examples of such groups are —OCH₃ and —OC₂H₅. Unless set forth or recited to the contrary, all alkoxy groups described or claimed herein may be straight chain or branched, substituted or unsubstituted.

The term "cycloalkyl" denotes a non-aromatic mono or multicyclic ring system of 3 to about 12 carbon atoms, such as cyclopropyl, cyclobutyl, cyclopentyl, and cyclohexyl. Examples of multicyclic cycloalkyl groups include, but are not limited to, perhydronapththyl, adamantyl and norbornyl groups, bridged cyclic groups or sprirobicyclic groups, e.g., sprio(4,4)non-2-yl. Unless set forth or recited to the contrary, all cycloalkyl groups described or claimed herein may be substituted or unsubstituted.

The term "cycloalkylalkyl" refers to a cyclic ring-containing radical having 3 to about 8 carbon atoms directly attached to an alkyl group. The cycloalkylalkyl group may be attached to the main structure at any carbon atom in the alkyl group that results in the creation of a stable structure. Non-limiting examples of such groups include cyclopropylmethyl, cyclobutylethyl, and cyclopentylethyl. Unless set forth or recited to the contrary, all cycloalkylalkyl groups described or claimed herein may be substituted or unsubstituted.

The term "cycloalkenyl" refers to a cyclic ring-containing radical having 3 to about 8 carbon atoms with at least one carbon-carbon double bond, such as cyclopropenyl, cyclobutenyl, and cyclopentenyl. Unless set forth or recited to the contrary, all cycloalkenyl groups described or claimed herein may be substituted or unsubstituted.

The term "aryl" refers to an aromatic radical having 6 to 14 carbon atoms, including monocyclic, bicyclic and tricyclic aromatic systems, such as phenyl, naphthyl, tetrahydronapthyl, indanyl, and biphenyl. Unless set forth or recited to the contrary, all aryl groups described or claimed herein may be substituted or unsubstituted.

The term "arylalkyl" refers to an aryl group as defined above directly bonded to an alkyl group as defined above, e.g., —$CH_2C_6H_5$ and —$C_2H_4C_6H_5$. Unless set forth or recited to the contrary, all arylalkyl groups described or claimed herein may be substituted or unsubstituted.

The term "heterocyclic ring" or "heterocyclyl" unless otherwise specified refers to substituted or unsubstituted non-aromatic 3 to 15 membered ring radical which consists of carbon atoms and from one to five heteroatoms selected from nitrogen, phosphorus, oxygen and sulfur. The heterocyclic ring radical may be a mono-, bi- or tricyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized; also, unless otherwise constrained by the definition the heterocyclic ring or heterocyclyl may optionally contain one or more olefinic bond(s). Examples of such heterocyclic ring radicals include, but are not limited to azepinyl, azetidinyl, benzodioxolyl, benzodioxanyl, chromanyl, dioxolanyl, dioxaphospholanyl, decahydroisoquinolyl, indanyl, indolinyl, isoindolinyl, isochromanyl, isothiazolidinyl, isoxazolidinyl, morpholinyl, oxazolinyl, oxazolidinyl, oxadiazolyl, 2-oxopiperazinyl, 2-oxopiperidinyl, 2-oxopyrrolidinyl, 2-oxoazepinyl, octahydroindolyl, octahydroisoindolyl, perhydroazepinyl, piperazinyl, 4-piperidonyl, pyrrolidinyl, piperidinyl, phenothiazinyl, phenoxazinyl, quinuclidinyl, tetrahydroisquinolyl, tetrahydrofuryl, tetrahydropyranyl, thiazolinyl, thiazolidinyl, thiamorpholinyl, thiamorpholinyl sulfoxide and thiamorpholinyl sulfone. The heterocyclic ring radical may be attached to the main structure at any heteroatom or carbon atom that results in the creation of a stable structure. Unless set forth or recited to the contrary, all heterocyclyl groups described or claimed herein may be substituted or unsubstituted.

The term "heterocyclylalkyl" refers to a heterocyclic ring radical directly bonded to an alkyl group. The heterocyclylalkyl radical may be attached to the main structure at any carbon atom in the alkyl group that results in the creation of a stable structure. Unless set forth or recited to the contrary, all heterocyclylalkyl groups described or claimed herein may be substituted or unsubstituted.

The term "heteroaryl" unless otherwise specified refers to substituted or unsubstituted 5 to 14 membered aromatic heterocyclic ring radical with one or more heteroatom(s) independently selected from N, O or S. The heteroaryl may be a mono-, bi- or tricyclic ring system. The heteroaryl ring radical may be attached to the main structure at any heteroatom or carbon atom that results in the creation of a stable structure. Examples of such heteroaryl ring radicals include, but are not limited to oxazolyl, isoxazolyl, imidazolyl, furyl, indolyl, isoindolyl, pyrrolyl, triazolyl, triazinyl, tetrazoyl, thienyl, thiazolyl, isothiazolyl, pyridyl, pyrimidinyl, pyrazinyl, pyridazinyl, benzofuranyl, benzothiazolyl, benzoxazolyl, benzimidazolyl, benzothienyl, benzopyranyl, carbazolyl, quinolinyl, isoquinolinyl, quinazolinyl, cinnolinyl, naphthyridinyl, pteridinyl, purinyl, quinoxalinyl, quinolyl, isoquinolyl, thiadiazolyl, indolizinyl, acridinyl, phenazinyl and phthalazinyl. Unless set forth or recited to the contrary, all heteroaryl groups described or claimed herein may be substituted or unsubstituted.

The term "heteroarylalkyl" refers to a heteroaryl ring radical directly bonded to an alkyl group. The heteroarylalkyl radical may be attached to the main structure at any carbon atom in the alkyl group that results in the creation of a stable structure. Unless set forth or recited to the contrary, all heteroarylalkyl groups described or claimed herein may be substituted or unsubstituted.

Unless otherwise specified, the term "substituted" as used herein refers to a group or moiety having one or more of the substituents attached to the structural skeleton of the group or moiety, including, but not limited to such substituents as hydroxy, halogen, carboxyl, cyano, nitro, oxo (=O), thio (=S), substituted or unsubstituted alkyl, substituted or unsubstituted haloalkyl, substituted or unsubstituted alkoxy, substituted or unsubstituted haloalkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkylalkyl, substituted or unsubstituted cycloalkenyl, substituted or unsubstituted amino, substituted or unsubstituted aryl, substituted or unsubstituted heteroaryl, substituted or unsubstituted heterocyclylalkyl ring, substituted or unsubstituted heteroarylalkyl, substituted or unsubstituted heterocyclic ring, substituted or unsubstituted guanidine, —$COOR^x$, —$C(O)R^x$, —$C(S)R^x$, —$C(O)NR^xR^y$, —$C(O)ONR^xR^y$, —$NR^xCONR^yR^z$, —$N(R)SOR^y$, —$N(R^x)SO_2R^y$, —(=N—N($R^x$)$R^y$), —$NR^xC(O)OR^y$, —$NR^xR^y$, —$NR^xC(O)R^y$, —$NR^xC(S)R^y$, —$NR^xC(S)NR^yR^z$, —$SONR^xR^y$, —$SO_2NR^xR^y$, —$OR^x$, —$OR^xC(O)NR^yR^z$, —$OR^xC(O)OR^y$, —$OC(O)R^x$, —$OC(O)NR^xR^y$, —$R^xNR^yC(O)R^z$, —$R^xOR^y$, —$R^xC(O)OR^y$, —$R^xC(O)NR^yR^z$, —$R^xC(O)R^y$, —$R^xOC(O)R^y$, —$SR^x$, —$SOR^x$, —$SO_2R^x$, and —$ONO_2$, wherein $R^x$, $R^y$ and $R^z$ are independently selected from hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, substituted heterocyclylalkyl ring, substituted or unsubstituted heteroarylalkyl, or substituted or unsubstituted heterocyclic ring. The substituents in the aforementioned "substituted" groups cannot be further substituted. For example, when the substituent on "substituted alkyl" is "substituted aryl", the substituent on "substituted aryl" cannot be "substituted alkenyl".

The term "treating" or "treatment" of a state, disorder or condition includes: (a) preventing or delaying the appearance of clinical symptoms of the state, disorder or condition developing in a subject that may be afflicted with or predisposed to the state, disorder or condition but does not yet experience or display clinical or subclinical symptoms of the state, disorder or condition; (b) inhibiting the state, disorder or condition, i.e., arresting or reducing the development of the disease or at least one clinical or subclinical symptom thereof; or (c) relieving the disease, i.e., causing regression of the state, disorder or condition or at least one of its clinical or subclinical symptoms.

The term "subject" includes mammals (especially humans) and other animals, such as domestic animals (e.g., household pets including cats and dogs) and non-domestic animals (such as wildlife).

A "therapeutically effective amount" means the amount of a compound that, when administered to a subject for treating a state, disorder or condition, is sufficient to cause the effect in the subject which is the purpose of the administration. The "therapeutically effective amount" will vary depending on the compound, the disease and its severity and the age, weight, physical condition and responsiveness of the subject to be treated.

The compound described in the present patent application may form salts. Non-limiting examples of pharmaceutically acceptable salts forming part of this patent application include salts derived from inorganic bases, salts of organic bases, salts of chiral bases, salts of natural amino acids and salts of non-natural amino acids. With respect to the overall compounds described by the Formula (I), the present patent application extends to these stereoisomeric forms and to mixtures thereof. To the extent prior art teaches synthesis or separation of particular stereoisomers, the different stereoisomeric forms of the present patent application may be separated from one another by the method known in the art, or a given isomer may be obtained by stereospecific or asymmetric synthesis. Tautomeric forms and mixtures of compounds described herein are also contemplated.

Pharmaceutical Compositions

The pharmaceutical composition provided in the present invention includes at least one compound described herein and at least one pharmaceutically acceptable excipient (such as a carrier or diluent). Preferably, the contemplated pharmaceutical compositions include the compound(s) described herein in an amount sufficient to inhibit TRPV3 receptor in a subject.

The subjects contemplated include, for example, a living cell and a mammal, including human. The compound of the present invention may be associated with a pharmaceutically acceptable excipient (such as a carrier or a diluent) or be diluted by a carrier, or enclosed within a carrier which can be in the form of a capsule, sachet, paper or other container.

Examples of suitable carriers include, but are not limited to, water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicylic acid, fatty acids, fatty acid amines, fatty acid monoglycerides and diglycerides, pentaerythritol fatty acid esters, polyoxyethylene, hydroxymethylcellulose and polyvinylpyrrolidone.

The pharmaceutical composition may also include one or more pharmaceutically acceptable auxiliary agents, wetting agents, emulsifying agents, suspending agents, preserving agents, salts for influencing osmotic pressure, buffers, sweetening agents, flavoring agents, colorants, or any combination of the foregoing. The pharmaceutical composition of the invention may be formulated so as to provide quick, sustained, or delayed release of the active ingredient after administration to the subject by employing procedures known in the art.

The pharmaceutical compositions described herein may be prepared by conventional techniques known in the art. For example, the active compound can be mixed with a carrier, or diluted by a carrier, or enclosed within a carrier, which may be in the form of an ampoule, capsule, sachet, paper, or other container. When the carrier serves as a diluent, it may be a solid, semi-solid, or liquid material that acts as a vehicle, excipient, or medium for the active compound. The active compound can be adsorbed on a granular solid container, for example, in a sachet.

The pharmaceutical compositions may be in conventional forms, for example, capsules, tablets, aerosols, solutions, suspensions or products for topical application.

The route of administration may be any route which effectively transports the active compound of the invention to the appropriate or desired site of action. Suitable routes of administration include, but are not limited to, oral, nasal, pulmonary, buccal, subdermal, intradermal, transdermal, parenteral, rectal, depot, subcutaneous, intravenous, intraurethral, intramuscular, intranasal, ophthalmic (such as with an ophthalmic solution) or topical (such as with a topical ointment).

Solid oral formulations include, but are not limited to, tablets, capsules (soft or hard gelatin), dragees (containing the active ingredient in powder or pellet form), troches and lozenges. Tablets, dragees, or capsules having talc and/or a carbohydrate carrier or binder or the like are particularly suitable for oral application. Liquid formulations include, but are not limited to, syrups, emulsions, soft gelatin and sterile injectable liquids, such as aqueous or non-aqueous liquid suspensions or solutions. For parenteral application, particularly suitable are injectable solutions or suspensions formulation.

Liquid formulations include, but are not limited to, syrups, emulsions, soft gelatin and sterile injectable liquids, such as aqueous or non-aqueous liquid suspensions or solutions.

For parenteral application, particularly suitable are injectable solutions or suspensions, preferably aqueous solutions with the active compound dissolved in polyhydroxylated castor oil.

Suitable doses of the compounds for use in treating the diseases and disorders described herein can be determined by those skilled in the relevant art. Therapeutic doses are generally identified through a dose ranging study in humans based on preliminary evidence derived from the animal studies. Doses must be sufficient to result in a desired therapeutic benefit without causing unwanted side effects. For example, the daily dosage of the TRPV3 modulator can range from about 0.1 to about 30.0 mg/kg. Mode of administration, dosage forms, suitable pharmaceutical excipients, diluents or carriers can also be well used and adjusted by those skilled in the art. All changes and modifications are envisioned within the scope of the present invention.

Methods of Treatment

The present invention provides compounds and pharmaceutical formulations thereof that are useful in the treatment of diseases, conditions and/or disorders modulated by TRPV3. The present patent application further provides a method of treating a disease, condition and/or disorder modulated by TRPV3 in a subject in need thereof by administering to the subject a therapeutically effective amount of a compound or a pharmaceutical composition of the present invention.

Diseases, conditions, and/or disorders that are modulated by TRPV3 are believed to include, but are not limited to pain, nociceptive pain, dental pain, cardiac pain arising from an ischemic myocardium, pain due to migraine, acute pain, chronic pain, neuropathic pain, post-operative pain, pain due to neuralgia (e.g., post-herpetic neuralgia or trigeminal neuralgia), pain due to diabetic neuropathy, dental pain and cancer pain, inflammatory pain conditions (e.g. arthritis and osteoarthritis), arthralgia, neuropathies, neurodegeneration, retinopathy, neurotic skin disorder, stroke, urinary bladder hypersensitiveness, urinary incontinence, vulvodynia, gastrointestinal disorders such as irritable bowel syndrome, gastro-esophageal reflux disease, enteritis, ileitis, stomach-duodenal ulcer, inflammatory bowel disease, Crohn's disease, celiac disease, an inflammatory disease such as pancreatitis, a respiratory disorder such as allergic and non-allergic rhinitis, asthma or chronic obstructive pulmonary disease, irritation of skin, eye or mucous membrane, dermatitis, pruritic conditions such as uremic pruritus, fervescence, muscle spasms, emesis, dyskinesias, depression, Huntington's disease, memory deficits, restricted brain function, amyotrophic lateral sclerosis (ALS), dementia, arthritis, osteoarthritis, rheumatoid arthritis, diabetes, obesity, urticaria, actinic keratosis, keratocanthoma, alopecia, Meniere's disease, tinnitus, hyperacusis, anxiety disorders and benign prostate hyperplasia. Additional diseases, conditions and/or disorders modulated by TRPV3 is illustrated, for example in WO2007/056124; Wissenbach, U. et al, *Biology of the cell* (2004), 96, 47-54; Nilius, B. et al., *Physiol Rev* (2007), 87, 165-217; Okuhara, D. Y. et al, *Expert Opinion on Therapeutic Targets* (2007), 11, 391-401; Hu, H. Z. et al, *Journal of Cellular Physiology*, (2006), 208, 201-212 and references cited therein, all of which are incorporated herein by reference in their entirety and for the purpose stated.

General Methods of Preparation

The compounds described herein may be prepared by techniques known in the art. In addition, the compounds described herein may be prepared by following the reaction sequence as depicted in Schemes 1 to 6. Further, in the following schemes, where specific bases, acids, reagents, solvents, coupling agents, etc. are mentioned, it is understood that other bases, acids, reagents, solvents, coupling agents etc. known in the art may also be used and are therefore included within the scope of the present invention. Variations in reaction conditions, for example, temperature and/or duration of the reaction, which may be used as known in the art are also within the scope of the present invention. All the isomers of the compounds in described in these schemes, unless otherwise specified, are also encompassed within the scope of this invention Several substituted or unsubstituted heteroaryl amines (e.g., 2-amino-1,3-oxazole, 2-amino-1,3-thiazole, 2-amino-1,3,4-thiadiazole, 2-amino-1,3,4-oxadiazole 3-amino-1,2,4-triazole, 2-aminoimidazole, 2-aminopyridine, 2-aminopyrimidine, 4-aminopyrimidine, 3-aminopyridazine, 2-aminopyrazine, 2-aminobenzothiazole, 2-aminobenzoxazole, 2-aminobenzimidazole) used in the synthesis were either commercially available or can be prepared by the methods known in the art. Some of the amines used in the preparation of compounds of the invention are commercially available. 4-(Trifluoromethyl)-1,3-thiazol-2-amine used in the synthesis of the compounds of present invention, was prepared according to the procedure described Tanaka, K. et al. *J. Het. Chem.* 1991, 28, 907-910. 4-(Trifluoromethyl)-1,3-oxazol-2-amine used for the preparation of compounds of the present invention were prepared according to the procedure described in Foulis, M. *J. et al. J. Med. Chem.* 1971, 28, 1075-1077. 2-Bromoethyl acetoacetate was purchased from Aldrich.

A wide variety of substituted benzaldehydes are commercially available. Specific examples where a differentially substituted 2,3-dialkoxybenzaldehyde (5) is required, can be prepared by using commercially available (Sigma-Aldrich) 2,3-dihydroxybenzaldehyde (1) or o-vanillin (2-hydroxy-3-methoxybenzaldehyde) (4) as shown in Scheme 1. Thus, 2,3-dihydroxybenzaldehyde (1) is selectively alkylated with an appropriate cyclic halide (e.g., cyclopentyl bromide) followed by the second alkylation with 1-chloro-1,1-difluoromethane in presence of base to give compound of formula (3). The compound of formula (3) undergoes dealkylation in presence of an acid, to afford hydroxy compound which upon further alkylation by using suitable alkyl halide ($R^aX$), in presence of base gives compound of formula (5) (when $R^b$ is —$CHF_2$). 2,3-Dialkoxybenzaldehyde of the formula (5) when $R^b$ is $CH_3$, can be prepared by alkylation of o-vanillin (4) with an appropriate alkyl halide of the formula $R^aX$ in the presence of a suitable base.

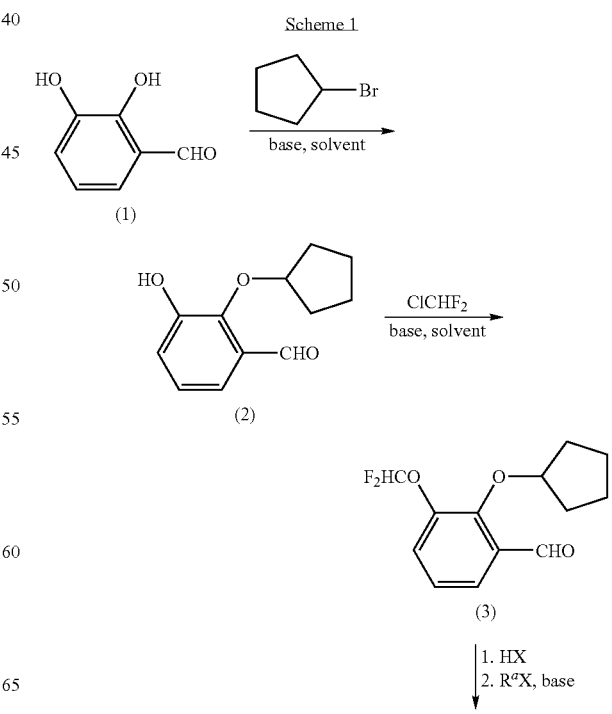

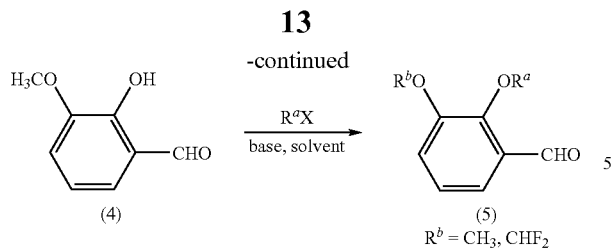

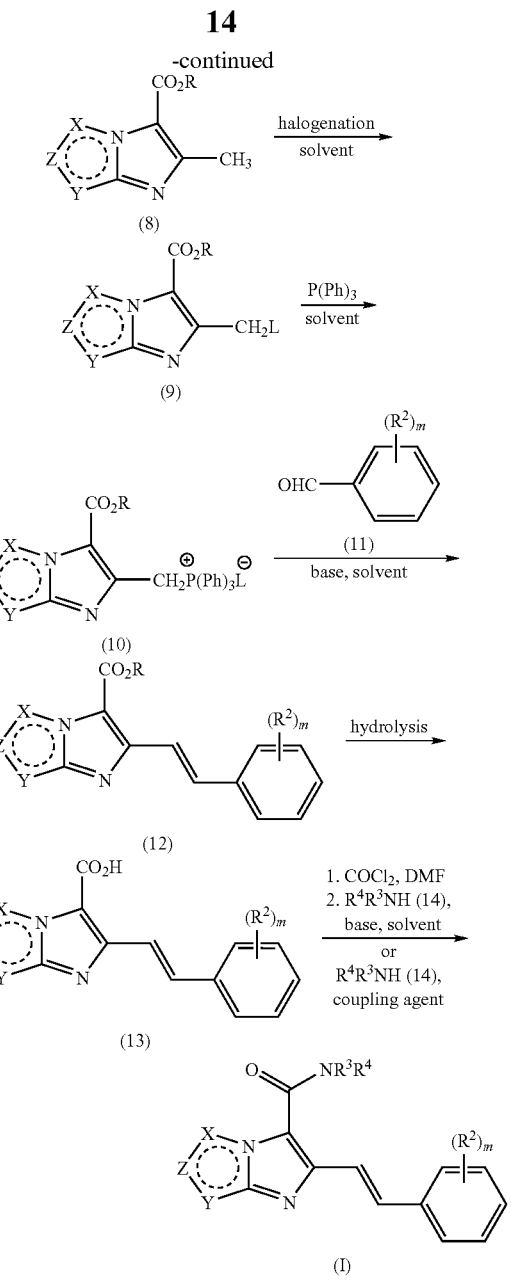

Fused imidazoles carboxylic acid intermediates (e.g., imidazo[2,1-b][1,3]thiazole-5-carboxylate, imidazo[1,2-a]pyridine-3-carboxylate) can be prepared according to methods known in the literature. Useful methods can be found in Otuk, G. *Eur. J. Med. Chem.* 1994, 29, 981-983; Krbavcic, A. et al. *J. Het. Chem.* 2000, 37, 95-101; Starrett, J. E. et al. *J. Med. Chem.* 1989, 32, 2204-2210; Laneri, S. *Eur. J. Med. Chem.* 1998, 33, 163-170.

An approach for the synthesis of compounds of the general formula (I) wherein X, Y, Z, $R^2$, $R^3$, $R^4$, and 'm' are as defined above, is described in Scheme 2. An heteroaryl amines of the formula (6) is converted to a fused bicyclic ester of formula (8) by reaction with 2-haloalkyl acetoacetate (7) (where L is halogen; and R is H or alkyl) in a suitable solvent such as ethanol. Radical halogenation of compound of formula (8) with suitable halogentaing agent [e.g., N-bromosuccinamide (NBS), N-chlorosuccinimide (NCS), N-iodosuccinimide (NIS)] in the presence of suitable free radical initiator (e.g., benzoyl peroxide, 2,2'-azobisisobutyronitrile (AIBN) and in suitable solvent (e.g., carbon tetrachloride, dichloroethane) affords corresponding bicyclic halomethyl ester of formula (9) where L is halogen. The ester halide of the formula (9) is then converted to the corresponding triphenylphosponium halide (10) by reaction with triphenylphospine in a suitable solvent (e.g., acetonitrile, toluene). This triphenylphosponium halide of general formula (10) is then converted into (E)-styryl ester of a formula (12) by reacting with appropriately substituted aldehyde of formula (11) in the presence of suitable base (e.g., sodium hydride, potassium tert-butoxide) in a suitable solvent (e.g., dimethylformamide, dimethyl sulfoxide) via a Wittig reaction. Hydrolysis of (E)-styryl ester of general formula (12) using suitable base (e.g., sodium hydroxide, potassium hydroxide, lithium hydroxide) in suitable solvent or a mixture of solvents (e.g., tetrahydrofuran, ethanol, methanol, water) affords corresponding carboxylic acid of general formula (13). Coupling of carboxylic acid of a formula (13) with an amine of a formula $HNR^3R^4$ (14) using suitable coupling agents [e.g. N-ethyl-N'-(3-dimethylaminopropyl)carbodiimide hydrochloride (EDCI), b enzotriazol-1-yloxytris(dimethylamino) phosphonium-hexafluorophosphate (BOP)] in a suitable solvent or mixture of solvents (e.g. N,N-dimethyl formamide, tetrahydrofuran, dichloromethane) gives compound of general formula (I). Alternatively, reaction of acid chloride, prepared by the reaction of carboxylic acid (13) with thionyl chloride or oxalyl chloride) with an amine of general formula $HNR^3R^4$ (14) in the presence of a suitable base (e.g., triethylamine, N, N-diisopropylethylamine) in a suitable solvent (e.g., N,N-dimethylformamide, dichloromethane, tetrahydrofuran) gives compound of general formula (I).

Scheme 2

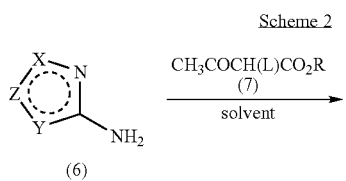

Another approach for the synthesis of compounds of the general formula (Ia) wherein X, Y, Z, $R^a$, $R^b$, $R^3$, and $R^4$ are as defined above, is described in Scheme 3. Triphenylphosponium halide of general formula (10) is converted into (E)-styryl ester of a formula (15) by reacting with appropriately substituted aldehyde of formula (5) in the presence of suitable base (e.g., sodium hydride, potassium tert-butoxide) in a suitable solvent (e.g., dimethylformamide, dimethyl sulfoxide) via a Wittig reaction. Hydrolysis of (E)-styryl ester of general formula (15) using suitable base (e.g., sodium hydroxide, potassium hydroxide, lithium hydroxide) in suitable solvent or a mixture of solvents (e.g., tetrahydrofuran, ethanol, methanol, water) affords corresponding carboxylic acid of general formula (16). The intermediate of formula (16) is coupled with an appropriate amine of the formula (14) using an appropriate coupling agent and base as described above, gives compounds of the present invention represented by the compound of formula (Ia). Compound of a general formula (Ia) also can be converted into 2,3-dihydroxy compound of formula (Ib) by exhaustive dealkylation using an appropriate Lewis acid (e.g., boron tribromide).

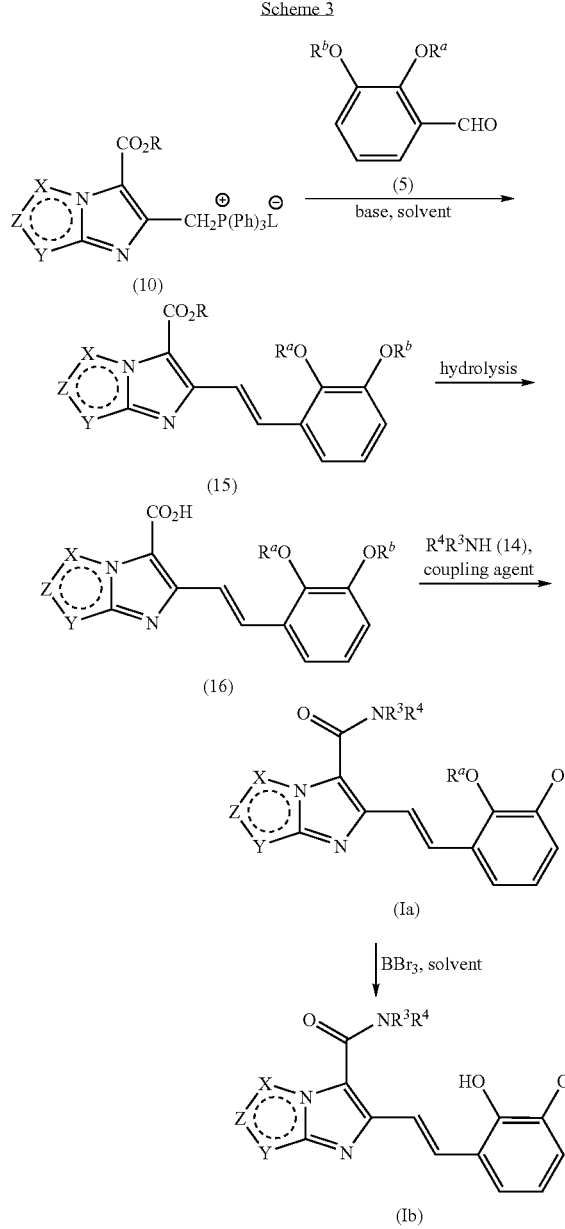

An approach for the synthesis of compound of the general formula (II) or (IIa) (wherein $R^a$, $R^1$, $R^3$, and $R^4$ are as defined above) wherein the imidazole ring is fused to a 5-membered ring (X is N, or $CR^1$ and Y is oxygen or sulfur) is described in Scheme 4. Triphenylphosponium halide of general formula (17) is converted into (E)-styryl ester of a formula (18) by reacting with 2-(cyclopentyloxy)-3-(difluoromethoxy)benzaldehyde of formula (3) in the presence of suitable base (e.g., sodium hydride, potassium tert-butoxide) in a suitable solvent (e.g., dimethylformamide, dimethyl sulfoxide) via a Wittig reaction. Decyclopentylation of (E)-styryl ester of general formula (18) under acidic condition (e.g., mixture of 48% hydrobromic acid and acetic acid) affords corresponding monohydroxy compound of general formula (19). Alkylation of monohydroxy compound of formula (19) with suit-able alkyl halide $R^aX$ using suitable base (e.g., potassium carbonate, sodium hydride, cesium carbonate) and in suitable polar solvent (e.g., N, N-dimethylformamide, tetrahydrofuran, dimethyl sulfoxide) affords (E)-styryl ester of formula (20). Hydrolysis of ester group in intermediate (20) under basic conditions affords the free acid (21). The intermediate (21) is coupled with an appropriate amine of the formula (14) using an appropriate coupling agent and base as described above, gives compounds of the present invention represented by the compound formula (II). Amides of the general formula (II), derived from primary amines such as anilines and 2-aminothiazoles can be converted to the corresponding alkali metal amides due to the acidic nature of the amide proton. Thus, selected amides of the formula (II) is treated with a suitable metal hydroxides, metal alkoxides, metal hydrides (e.g., sodium hydroxide, potassium hydroxide, sodium alkoxide, potassium alkoxide, sodium hydride, potassium hydride) in a suitable solvent to give salt of the formula (IIa).

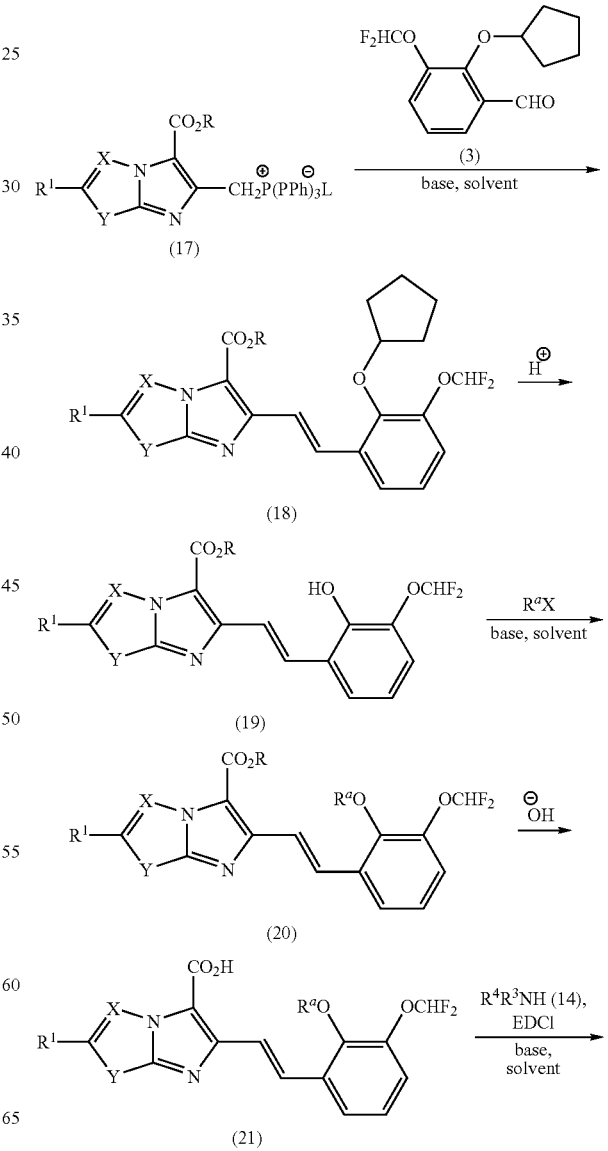

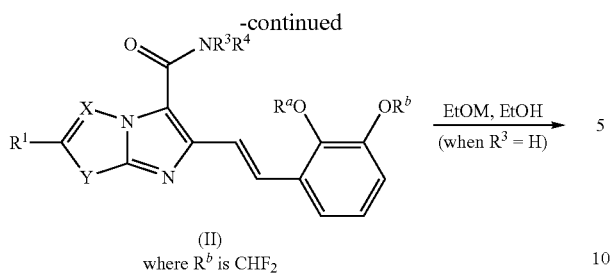

(II)
where $R^b$ is $CHF_2$

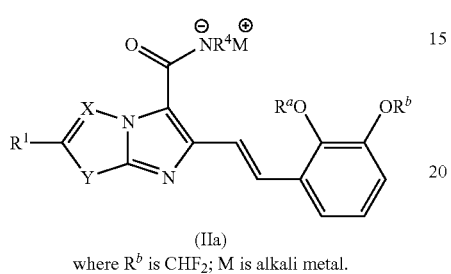

(IIa)
where $R^b$ is $CHF_2$; M is alkali metal.

An approach for the synthesis of compounds of the formula (III) or (IIIa) (wherein $R^a$, $R^b$, $R^1$, $R^3$, $R^4$, and 'n' are as defined above) where the imidazole ring is fused to a 6-membered aromatic ring to result an imidazo[1,2-a]pyridine ring is shown in Scheme 5. Substituted or unsubstituted 2-aminopyridine of the general formula (22) with 2-haloalkyl acetoacetate of a formula (7) (where L is halogen; and R is H or alkyl) in a suitable solvent (e.g. ethanol) gives the bicyclic ester (23). Ester (23) on allylic bromination under radical halogenation conditions, using a suitable halogentaing agent such as NBS in a suitable solvent gives the bromomethyl derivative (24). Intermediate (24) is converted to the corresponding Wittig salt (25) by its reaction with triphenylphospine in suitable solvent such as acetonitrile or toluene. Base mediated reaction of intermediate (25) with an appropriate aryl aldehyde of formula (5) in a suitable aprotic solvent gives trans olefin ester which further hydrolysed under basic conditions to give the free acid of general formula (26). The intermediate (26) is coupled with an appropriate amine of the formula (14) using an appropriate coupling agent and base as described above gives compounds of the present invention represented by the general formula (III). Alternatively, the amides of the general formula (III) can be prepared by base assisted coupling of amine of the general formula (14) with the acid chloride of intermediate (26), generated by means of thionyl chloride or oxalyl chloride. Amides of the formula (III) (when $R^3$=H) is converted into corresponding alkali metal salt of formula (IIIa) using suitable metal hydroxides, metal alkoxides or metal hydrides (e.g., sodium hydroxide, potassium hydroxide, sodium alkoxide, potassium alkoxide, sodium hydride, potassium hydride) in presence of a suitable solvent.

Scheme 5

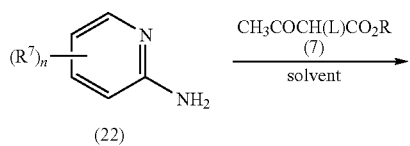

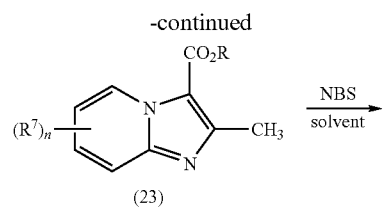

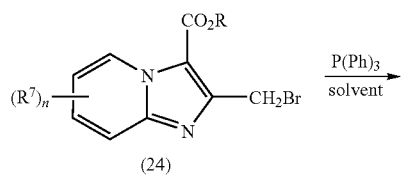

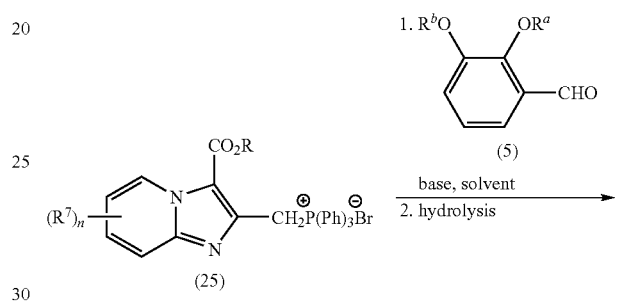

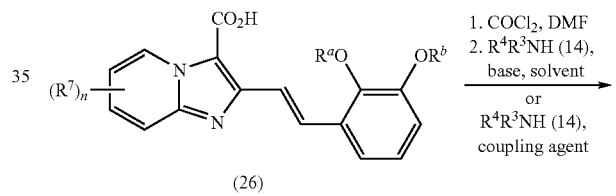

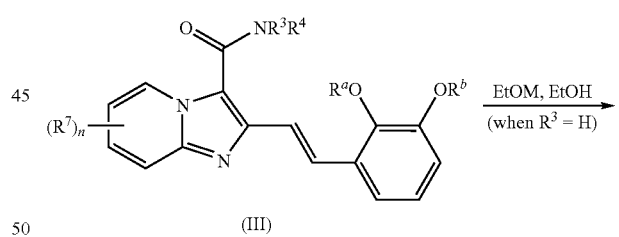

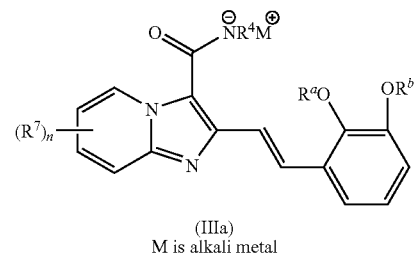

(IIIa)
M is alkali metal

Scheme 6 depicts an alternate approach for the preparation of compound of formula (II). In this scheme coupling of compound of formula (20) (where R is substituted or unsubstituted alkyl or aryl) with amine of formula (14) in presence of base affords compound of formula (II) (where $R^b$ is $CHF_2$).

Scheme 6

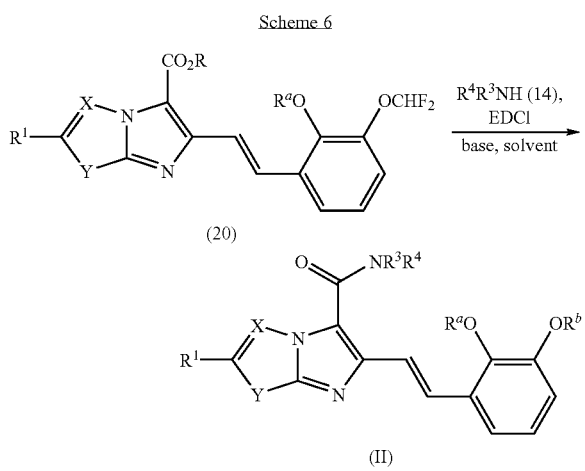

Experimental

Unless otherwise stated, work-up implies the following operations: distribution of the reaction mixture between the organic and aqueous phase, separation of layers, drying the organic layer over sodium sulfate, filtration and evaporation of the organic solvent. Purification, unless otherwise mentioned, implies purification by silica gel chromatographic techniques, generally using ethyl acetate/petroleum ether mixture of a suitable polarity as the mobile phase. The following abbreviations are used in the text: DMSO-$d_6$: hexadeuterodimethyl sulfoxide; DMF: N,N-dimethylformamide, J: coupling constant in units of Hz; RT: room temperature (22-26° C.). aq.: aqueous AcOEt: ethyl acetate; equiv.: equivalents.

Preparation of Intermediates

All (E)-phenylvinyl imidazo[2,1-b][1,3]thiazole carboxylic acid and (E)-phenylvinyl imidazo[1,2-a]pyridine-3-carboxylic acid intermediates used for the preparation of compounds of the present invention, were prepared according to the synthetic schemes provided in 'General Methods of Preparation'. However, these intermediates may be prepared by alternative approaches reported in the literature or by methods known to people skilled in the art of organic synthesis. Detailed experimental procedures for the synthesis of intermediates are given below.

Intermediate 1: 6-{(E)-2-[2-(Cyclopropylmethoxy)-3-methoxyphenyl]vinyl}imidazo[2,1-b][1,3]thiazole-5-carboxylic acid

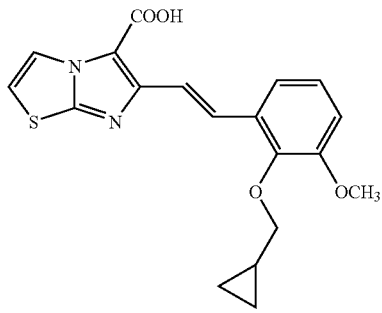

Step 1 Ethyl 6-methylimidazo[2,1-b][1,3]thiazole-5-carboxylate: A mixture of 2-aminothiazole (5.0 g. 49.931 mmol) and ethyl 2-chloroacetoacetate (11.5 g, 69.965 mmol) in absolute ethanol (50 mL) was refluxed for 24 h under stirring. The solvent was evaporated under vacuum and the residue was triturated with water (150 mL). The resulting solid was filtered, and dried to give crude product which was further purified by column chromatography to give 3.15 g of the product as an off-white solid; $^1$H NMR (300 MHz, CDCl$_3$) δ 1.41 (t, J=6.9 Hz, 3H), 2.61 (s, 3H), 4.38 (q, J=6.6 Hz, 2H), 7.41 (d, J=4.2 Hz, 1H), 8.05 (d, J=4.5 Hz, 1H); ESI-MS (m/z) 211.30 (MH)$^+$.

Step 2 Ethyl 6-(bromomethyl)imidazo[2,1-b][1,3]thiazole-5-carboxylate: To a stirred solution of Step 1 intermediate (2.60 g, 12.366 mmol) and azobisisobutyronitrile (AIBN) (0.041 g, 0.247 mmol) in carbon tetrachloride (40 mL) at reflux temperature was added N-bromosuccinimide (2.40 g, 13.602 mmol). After refluxing for 18 h, the reaction mixture was cooled to room temperature and diluted with ethyl acetate (200 mL) and water (100 mL). The layers were separated. Aqueous layer was extracted with ethyl acetate (2×50 mL) and the combined organic layers were washed with brine (2×50 mL), dried (Na$_2$SO$_4$) and filtered. The filtrate was concentrated under reduced pressure. The residue obtained after the evaporation of the solvent was purified by silica gel column chromatography using 5% ethyl acetate in petroleum ether to obtain 1.95 g of the product as a white solid; $^1$H NMR (300 MHz, DMSO-$d_6$) δ 1.36 (t, J=6.6 Hz, 3H), 4.36 (q, J=7.2 Hz, 2H), 4.85 (s, 2H), 7.52 (d, J=4.5 Hz, 1H), 8.10 (d, J=4.5 Hz, 1H); ESI-MS (m/z) 291.58 (MH)$^+$.

Step 3 5-Ethyloxycarbonylimidazo[2,1-b][1,3]thiazol-6-yl-methyl(triphenyl)phosphonium bromide: To a stirred suspension of Step 2 intermediate (1.90 g, 6.571 mmol) in acetonitrile (40 mL) was added triphenylphosphine (1.89 g, 7.228 mmol) at room temperature. The resulting reaction mixture was slowly heated to reflux overnight. The solvent was concentrated in vacuo and the residue was stirred with diisopropyl ether and filtered. The solid was dried under vacuum to afford 3.90 g of the product as an off-white solid: $^1$H NMR (300 MHz, DMSO-$d_6$) δ 1.17 (t, J=7.2 Hz, 3H), 4.08 (q, J=6.9 Hz, 2H), 5.35 (s, 1H), 5.40 (s, 1H), 7.20-7.22 (m, 1H), 7.37 (br s, 1H), 7.50 (d, J=4.5 Hz, 1H), 7.68-7.76 (m, 10H), 7.81-7.87 (m, 3H), 7.99 (d, J=3.9 Hz, 1H); ESI-MS (m/z) 471.24 (MH)$^+$.

Step 4 Ethyl 6-{(E)-2-[2-(cyclopropylmethoxy)-3-methoxyphenyl]vinyl}imidazo[2,1-b][1,3]thiazole-5-carboxylate: To a stirred suspension of Step 3 intermediate (2.0 g, 3.626 mmol) was added NaH (0.160 g, 3.989 mmol) in anhydrous DMSO (10 mL) and stirred for 30 min. A solution of 2-(cyclopropylmethoxy)-3-methoxybenzaldehyde (0.82 g, 3.989 mmol) in anhydrous DMSO (10 mL) was added drop wise to this solution at room temperature and stirred for 2 h. The reaction mixture was diluted with ethyl acetate (200 mL), washed with water (2×50 mL), brine and dried (Na$_2$SO$_4$) to yield a crude solid which was purified by column chromatography using 5% ethyl acetate in petroleum ether to afford 0.776 g of the product as an off-white solid; $^1$H NMR (300 MHz, DMSO-$d_6$) δ 0.26-0.28 (m, 2H), 0.50-0.53 (m, 2H), 1.17-1.23 (m, 1H), 1.39 (t, J=7.5 Hz, 3H), 3.75 (d, J=7.2 Hz, 2H), 3.79 (s, 3H), 4.37 (q, J=6.9 Hz, 2H), 6.95-6.99 (m, 2H), 7.08 (t, J=7.8 Hz, 1H), 7.18-7.22 (m, 1H), 7.43 (d, J=4.5 Hz, 1H), 7.69 (d, J=16.2 Hz, 1H), 7.92 (d, J=16.5 Hz, 1H), 8.10 (d, J=4.2 Hz, 1H); ESI-MS (m/z) 399.20 (MH)$^+$.

Step 5 6-{(E)-2-[2-(Cyclopropylmethoxy)-3-methoxyphenyl]vinyl}imidazo[2,1-b][1,3]thiazole-5-carboxylic acid: To a stirred solution of Step 4 intermediate (495 mg, 1.242 mmol) in THF (10 ml) was added LiOH.H$_2$O (105 mg, 2.484 mmol) dissolved in water (10 ml). The mixture was stirred for 2 h at room temperature. Solvent was evaporated under reduced pressure and the residue obtained was acidified with 1 N HCl to pH 4 and extracted with ethyl acetate (2×100 mL). The combined ethyl acetate extracts were washed with water (2×25 mL) and dried ($Na_2SO_4$). Evaporation of solvent under reduced pressure afforded 0.381 g of the product as a white solid; $^1$H NMR (300 MHz, DMSO-$d_6$) δ 0.26-0.28 (m, 2H), 0.49-0.53 (m, 2H), 1.16-1.22 (m, 1H), 3.75 (d, J=7.5 Hz, 2H), 3.79 (s, 3H), 6.95-6.99 (m, 1H), 7.04 (t, J=7.8 Hz, 1H), 7.16-7.27 (m, 1H), 7.39 (d, J=3.9 Hz, 1H), 7.71 (d, J=15.9 Hz, 1H), 7.79 (d, J=15.9 Hz, 1H), 8.10 (d, J=3.9 Hz, 1H), 13.44 (br s, 1H); ESI-MS (m/z) 369.08 (M−H)$^-$.

Intermediate 2: 6-{(E)-2-[2-(Isobutoxy)-3-methoxyphenyl]vinyl}imidazo[2,1-b][1,3]thiazole-5-carboxylic acid

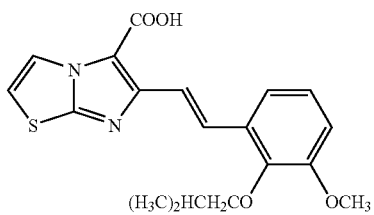

Step 1 Ethyl 6-{(E)-2-[2-(isobutoxy)-3-methoxyphenyl]vinyl}imidazo[2,1-b][1,3]thiazole-5-carboxylate: This compound was prepared as described in Intermediate 1 by the reaction of 2-isobutoxy-3-methoxybenzaldehyde (1.328 g, 5.984 mmol) with 5-ethyloxycarbonylimidazo[2,1-b][1,3]thiazol-6-yl-methyl(triphenyl)phosphonium bromide (3.0 g, 5.440 mmol) in the presence of sodium hydride (0.23 g, 5.984 mmol) in anhydrous DMSO (15 mL) to give 1.50 g of product as a white solid; $^1$H NMR (300 MHz, DMSO-$d_6$) δ 1.07 (d, J=6.9 Hz, 6H), 1.47 (t, J=6.9 Hz, 3H), 2.12-2.23 (m, 1H), 3.75 (d, J=6.6 Hz, 2H), 3.86 (s, 3H), 4.40-4.49 (m, 2H), 6.85 (d, J=7.8 Hz, 1H), 6.90 (d, J=4.5 Hz, 1H), 7.05 (t, J=7.8 Hz, 1H), 7.28-7.33 (m, 1H), 7.76 (d, J=16.2 Hz, 1H), 8.03 (d, J=16.2 Hz, 1H), 8.07-8.11 (m, 1H); APCI-MS (m/z) 399.09 (M−H)$^-$.

Step 2 6-{(E)-2-[2-(Isobutoxy)-3-methoxyphenyl]vinyl}imidazo[2,1-b][1,3]thiazole-5-carboxylic acid: Lithium hydroxide assisted hydrolysis of Step 1 intermediate (200 mg, 0.499 mmol) as described in Intermediate 1 gave 170 mg of the desired product as a white solid; $^1$H NMR (300 MHz, DMSO-$d_6$) δ 1.07 (d, J=6.3 Hz, 6H), 2.14-2.27 (m, 1H), 3.76 (d, J=6.3 Hz, 2H), 3.87 (s, 3H), 6.86 (d, J=7.8 Hz, 1H), 6.95 (d, J=4.5 Hz, 1H), 7.06 (t, J=7.8 Hz, 1H), 7.32 (d, J=7.2 Hz, 1H), 7.84 (d, J=16.2 Hz, 1H), 8.07 (d, J=16.2 Hz, 1H), 8.12-8.17 (m, 1H); APCI-MS (m/z) 373.07 (MH)$^+$.

Intermediate 3: 6-{(E)-2-[2-(2,2-Dimethylpropoxy)-3-methoxyphenyl]vinyl}imidazo[2,1-b][1,3]thiazole-5-carboxylic acid

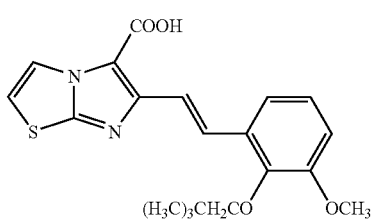

Step 1 Ethyl 6-{(E)-2-[2-(2,2-dimethylpropoxy)-3-methoxyphenyl]vinyl}imidazo[2,1-b][1,3]thiazole-5-carboxylate: This compound was prepared as described in Intermediate 1 by the reaction of 2-(2,2-dimethylpropoxy)-3-methoxybenzaldehyde (1.328 g, 5.984 mmol) with 5-ethyloxycarbonylimidazo[2,1-b][1,3]thiazol-6-yl-methyl (triphenyl)phosphonium bromide (3.0 g, 5.440 mmol) in the presence of sodium hydride (0.23 g, 5.984 mmol) in anhydrous DMSO (25 mL) to give 1.650 g of the product as an off-white solid; $^1$H NMR (300 MHz, DMSO-$d_6$) δ 1.05 (s, 9H), 1.39 (t, J=6.9 Hz, 3H), 3.57 (s, 2H), 3.80 (s, 3H), 4.39 (q, J=7.2 Hz, 2H), 6.99-7.02 (m, 1H), 7.10 (t, J=7.8 Hz, 1H), 7.22-7.25 (m, 1H), 7.46 (d, J=4.5 Hz, 1H), 7.67 (d, J=15.9 Hz, 1H), 7.94 (d, J=16.8 Hz, 1H), 8.12 (d, J=4.5 Hz, 1H); ESI-MS (m/z) 415.33 (M+H)$^+$.

Step 2 6-{(E)-2-[2-(2,2-Dimethylpropoxy)-3-methoxyphenyl]vinyl}imidazo[2,1-b][1,3]thiazole-5-carboxylic acid: Lithium hydroxide assisted hydrolysis of Step 1 intermediate (1.50 g, 3.618 mmol) as described in Intermediate 1 gave 1.20 g of the product as a white solid; $^1$H NMR (300 MHz, DMSO-$d_6$) δ 1.05 (s, 9H), 3.57 (s, 2H), 3.80 (s, 3H), 6.98-7.01 (m, 1H), 7.09 (t, J=8.1 Hz, 1H), 7.19-7.22 (m, 1H), 7.42 (d, J=4.5 Hz, 1H), 7.68 (d, J=16.5 Hz, 1H), 7.90 (d, J=16.2 Hz, 1H), 8.12 (d, J=4.2 Hz, 1H); ESI-MS (m/z) 387.11 (MH)$^+$.

Intermediate 4: 6-{(E)-2-[2-(Cyclopentyloxy)-3-methoxyphenyl]vinyl}imidazo[2,1-b][1,3]thiazole-5-carboxylic acid

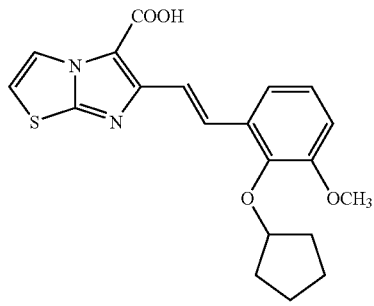

Step 1 Ethyl 6-{(E)-2-[2-(cyclopentyloxy)-3-methoxyphenyl]vinyl}imidazo[2,1-b][1,3]thiazole-5-carboxylate: This compound was prepared as described in Intermediate 1 by the reaction of 2-(cyclopentyloxy)-3-methoxybenzaldehyde (1.318 g, 5.984 mmol) with 5-ethyloxycarbonylimidazo[2,1-b][1,3]thiazol-6-yl-methyl(triphenyl)phosphonium bromide (3.0 g, 5.440 mmol) in the presence of sodium hydride (239 mg, 5.984 mmol) in anhydrous DMSO (20 mL) to give 1.610 g of the product as an off-white solid; $^1$H NMR (300 MHz, DMSO-$d_6$) δ 1.40 (t, J=6.9 Hz, 3H), 1.54-1.65 (m, 4H), 1.78-1.85 (m, 4H), 3.81 (s, 3H), 4.39 (q, J=7.2 Hz, 2H), 4.83-4.86 (m, 1H), 6.99-7.02 (m, 1H), 7.09 (t, J=8.1 Hz, 1H), 7.21-7.25 (m, 1H), 7.46 (d, J=4.5 Hz, 1H), 7.67 (d, J=16.2 Hz, 1H), 7.88 (d, J=16.2 Hz, 1H), 8.12 (d, J=4.5 Hz, 1H); ESI-MS (m/z) 413.27 (M+H)$^+$.

Step 2 6-{(E)-2-[2-(Cyclopentyloxy)-3-methoxyphenyl]vinyl}imidazo[2,1-b][1,3]thiazole-5-carboxylic acid: Lithium hydroxide assisted hydrolysis of Step 1 intermediate (1.50 g, 3.901 mmol) as described in Intermediate 1 gave 1.20 g of the desired product as a white solid; $^1$H NMR (300 MHz, DMSO-$d_6$) δ 1.54-1.64 (m, 4H), 1.77-1.82 (m, 4H), 3.81 (s, 3H), 4.83-4.86 (br s, 1H), 6.98-7.00 (m, 1H), 7.07 (t, J=7.8 Hz, 1H), 7.10-7.21 (m, 1H), 7.42 (d, J=4.5 Hz, 1H), 7.69 (d, J=16.5 Hz, 1H), 7.84 (d, J=16.2 Hz, 1H), 8.12 (d, J=4.5 Hz, 1H), 13.20 (br s, 1H); ESI-MS (m/z) 384.93 (MH)$^+$.

Intermediate 5: 6-{(E)-2-[2-(Cyclopentyloxy)-3-(difluoromethoxy)phenyl]vinyl}imidazo[2,1-b][1,3]thiazole-5-carboxylic acid

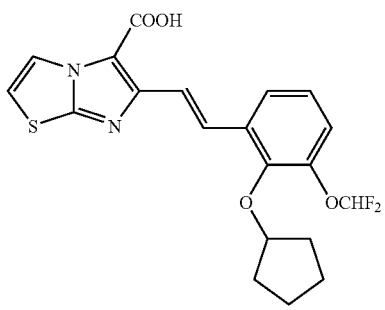

Step 1 Ethyl 6-{(E)-2-[2-(cyclopentyloxy)-3-(difluoromethoxy)phenyl]vinyl}imidazo[2,1-b][1,3]thiazole-5-carboxylate: This compound was prepared as described in Intermediate 1, step-4, by the reaction of 2-(cyclopentyloxy)-3-(difluoromethoxy)benzaldehyde (3.26 g, 12.766 mmol) with 5-ethyloxy carbonylimidazo[2,1-b][1,3]thiazol-6-yl-methyl (triphenyl)phosphonium bromide (6.40 g, 11.605 mmol) in the presence of sodium hydride (510 mg, 12.766 mmol) in anhydrous DMSO (20 mL) to give 4.20 g the product as an off-white solid; $^1$H NMR (300 MHz, DMSO-$d_6$) δ 1.40 (t, J=6.9 Hz, 3H), 1.54-1.60 (m, 2H), 1.65-1.72 (m, 2H), 1.80-1.86 (m, 4H), 4.35-4.44 (m, 2H), 4.70-4.78 (m, 1H), 7.10-7.16 (m, 2H), 7.18 (t, J=73.2 Hz, 1H), 7.40-7.46 (m, 1H), 7.54-7.60 (m, 1H), 7.74 (d, J=15.9 Hz, 1H), 7.85 (d, J=16.2 Hz, 1H), 8.10-8.16 (m, 1H); ESI-MS (m/z) 449.10 (M+H)$^+$.

Step 2 6-{(E)-2-[2-(Cyclopentyloxy)-3-(difluoromethoxy)phenyl]vinyl}imidazo[2,1-b][1,3]thiazole-5-carboxylic acid: Lithium hydroxide assisted hydrolysis of Step 1 intermediate (0.400 g, 0.892 mmol) as described in Intermediate 1 gave 0.375 g of the desired product as a white solid; $^1$H NMR (300 MHz, DMSO-$d_6$) δ 1.80-1.90 (m, 8H), 4.70-4.78 (m, 1H), 7.10-7.16 (m, 2H), 7.18 (t, J=74.1 Hz, 1H), 7.40-7.46 (m, 1H), 7.50-7.56 (m, 1H), 7.75-7.82 (m, 2H), 8.10-8.16 (m, 1H), 13.48 (br s, 1H); APCI-MS (m/z) 421.06 (MH)$^+$.

Intermediate 6: Ethyl 6-{(E)-2-[3-(difluoromethoxy)-2-hydroxyphenyl]vinyl}imidazo[2,1-b][1,3]thiazole-5-carboxylate

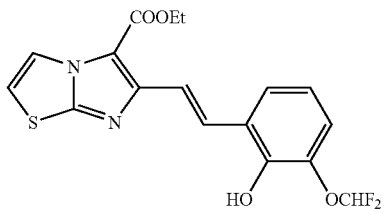

A solution of Ethyl 6-{(E)-2-[2-(cyclopentyloxy)-3-(difluoromethoxy)phenyl]vinyl}imidazo[2,1-b][1,3]thiazole-5-carboxylate (4.10 g, 9.149 mmol) from Intermediate 5, Step 1 in a mixture of 48% hydrobromic acid (20 mL) and glacial acetic acid (20 mL) was heated at 60° C. for 2 h. The reaction mixture was cooled to room temperature and neutralized with saturated solution of NaHCO$_3$. The mixture was extracted with ethyl acetate (2×100 mL) and the combined organic layers were washed with water (2×100 mL), dried over anhydrous Na$_2$SO$_4$. The residue obtained after the evaporation of the solvent was purified by silica gel column chromatography using 2% ethyl acetate in petroleum ether to obtain 3.0 g of the product as an off-white solid; $^1$H NMR (300 MHz, DMSO-$d_6$) δ 1.40 (t, J=6.3 Hz, 3H), 4.34-4.43 (m, 2H), 6.80-6.90 (m, 1H), 7.05-7.10 (m, 1H), 7.12 (t, J=69.0 Hz, 1H), 7.40-7.48 (m, 2H), 7.78 (d, J=16.2 Hz, 1H), 7.87 (d, J=16.2 Hz, 1H), 8.10-8.16 (m, 1H), 9.79 (br s, 1H); APCI-MS (m/z) 381.15 (MH)$^+$.

Intermediate 7A: 6-{(E)-2-[3-(Difluoromethoxy)-2-(2,2-dimethylpropoxy)phenyl]vinyl}imidazo[2,1-b][1,3]thiazole-5-carboxylic acid

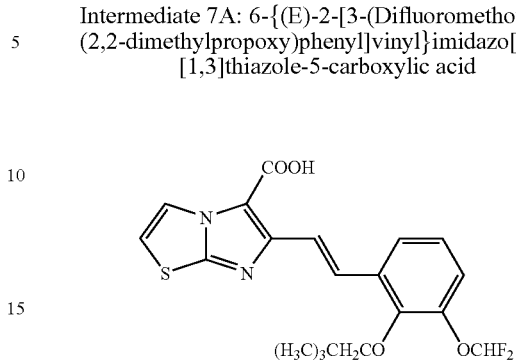

Step 1 Ethyl 6-{(E)-2-[3-(difluoromethoxy)-2-(2,2-dimethylpropoxy)phenyl]vinyl}imidazo[2,1-b][1,3]thiazole-5-carboxylate: To a stirred solution of Intermediate 6 (1.60 g, 4.209 mmol) in anhydrous N,N-dimethylformamide (10 mL) was added cesium carbonate (2.74 g, 8.418 mmol) followed by 1-bromo-2,2-dimethylpropane (1.60 mL, 12.629 mmol) at room temperature. The resulting suspension was stirred at 110° C. overnight under nitrogen atmosphere. The reaction mixture was cooled to room temperature and diluted with ethyl acetate (200 mL) and water (100 mL). The layers were separated. Aqueous layer was extracted with ethyl acetate (2×50 mL) and the combined organic layers were washed with brine (2×50 mL), dried (Na$_2$SO$_4$) and filtered. The filtrate was concentrated under reduced pressure. The residue obtained after the evaporation of the solvent was purified by silica gel column chromatography using 10% ethyl acetate in petroleum ether to obtain 1.20 g of the product as an off-white solid; $^1$H NMR (300 MHz, DMSO-$d_6$) δ 1.07 (s, 9H), 1.39 (t, J=6.9 Hz, 3H), 3.57 (s, 2H), 4.35-4.42 (m, 2H), 7.18 (t, J=74.7 Hz, 1H), 7.20-7.25 (m, 2H), 7.47 (d, J=3.9 Hz, 1H), 7.52-7.58 (m, 1H), 7.73 (d, J=16.2 Hz, 1H), 7.90 (d, J=16.2 Hz, 1H), 8.10-8.16 (m, 1H); APCI-MS (m/z) 451.10 (MH)$^+$.

Step 2 6-{(E)-2-[3-(Difluoromethoxy)-2-(2,2-dimethylpropoxy)phenyl]vinyl}imidazo [2,1-b][1,3]thiazole-5-carboxylic acid: Lithium hydroxide assisted hydrolysis of Step 1, ester (1.20 g, 2.665 mmol) as described in Intermediate 1 afforded 1.04 g of product as a white solid; $^1$H NMR (300 MHz, DMSO-$d_6$) δ 1.07 (s, 9H), 3.34 (s, 2H), 7.19 (t, J=77.7 Hz, 1H), 7.20-7.25 (m, 2H), 7.38-7.45 (m, 1H), 7.50-7.55 (m, 1H), 7.75 (d, J=16.2 Hz, 1H), 7.86 (d, J=16.2 Hz, 1H), 8.10-8.16 (m, 1H), 13.48 (br, 1H); APCI-MS (m/z) 451.12 (MH)$^+$.

Intermediate 7B: 4-Nitrophenyl, 6-{(E)-2-[3-(difluoromethoxy)-2-(2,2-dimethyl propoxy)phenyl]vinyl}imidazo[2,1-b][1,3]thiazole-5-carboxylate

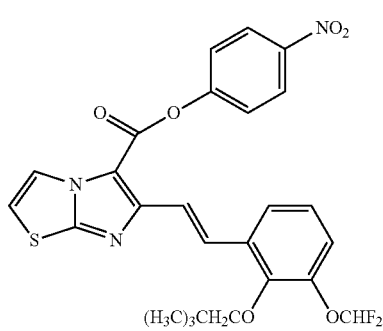

The title compound was prepared from Intermediate 7A. To a solution of Intermediate 7A (1.0 gm, 2.73 mmole) and EDCI (0.68 gm, 3.56 mmole) in THF (10 mL) was added 4-nitrophenol (0.395 gm, 2.84 mmol) at 60-65° C. The heating continued for 1 h and then solvent was removed under reduced pressure. The crude product thus obtained was further purified by column chromatography to give 0.90 gm of 4-nitrophenyl 6-{(E)-2-[3-(difluoromethoxy)-2-(2,2-dimethylpropoxy)phenyl]vinyl}imidazo[2,1-b][1,3]thiazole-5-carboxylate as a pale yellow solid; $^1$H NMR (300 MHz, DMSO-d6) δ 1.077 (s, 9H), 3.59 (s, 2H), 7.15-7.420 (m, 3H), 7.543-7.590 (m, 2H), 7.60-7.7785 (m, 3H), 7.980-8.036 (d, J=16.8 Hz, 1H), 8.225-8.239 (d, J=4.2 Hz, 1H), 8.374-8.405 (d, J=9.0 Hz, 2H); APCI-MS (m/z) 544.16 (M+H)$^+$ Intermediate 8: 6-{(E)-2-[3-(Difluoromethoxy)-2-(3-methylbutoxy)phenyl]vinyl}imidazo[2,1-b][1,3]thiazole-5-carboxylic acid

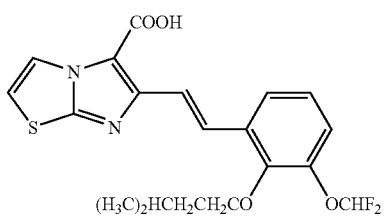

Step 1 Ethyl 6-{(E)-2-[3-(difluoromethoxy)-2-(3-methylbutoxy)phenyl]vinyl}imidazo[2,1-b][1,3]thiazole-5-carboxylate: Alkylation of Intermediate 6 (400 mg, 1.052 mmol) with 1-bromo-3-methylbutane (159 mg, 1.262 mmol) in presence of potassium carbonate (159 mg, 1.157 mmol) in anhydrous N,N-dimethylformamide (4 mL) as described in Intermediate 7A gave 475 mg of the compound as a white solid; $^1$H NMR (300 MHz, DMSO-d$_6$) δ 0.93 (t, J=6.6 Hz, 6H), 1.40 (t, J=7.2 Hz, 3H), 1.66 (q, J=6.3 Hz, 2H), 1.82-1.90 (m, 1H), 3.96 (t, J=6.3 Hz, 2H), 4.40 (q, J=6.9 Hz, 2H), 7.19 (t, J=71.4 Hz, 1H), 7.20-7.28 (m, 2H), 7.42-7.50 (m, 1H), 7.53-7.60 (m, 1H), 7.80 (s, 2H), 8.13 (d, J=4.2 Hz, 1H); APCI-MS (m/z) 451.23 (M+H)$^+$.

Step 2 6-{(E)-2-[3-(Difluoromethoxy)-2-(3-methylbutoxy)phenyl]vinyl}imidazo[2,1-b][1,3]thiazole-5-carboxylic acid: Lithium hydroxide assisted hydrolysis of Step 1 intermediate (450 mg, 0.999 mmol) as described in Intermediate 1 afforded 425 mg of the desired product as a white solid; $^1$H NMR (300 MHz, DMSO-d$_6$) δ 0.93 (t, J=6.6 Hz, 6H), 1.66 (q, J=6.6 Hz, 2H), 1.80-1.93 (m, 1H), 3.96 (t, J=6.6 Hz, 2H), 7.18 (t, J=74.7 Hz, 1H), 7.20-7.26 (m, 2H), 7.45 (s, 1H), 7.50-7.56 (m, 1H), 7.77 (d, J=15.6 Hz, 1H), 7.84 (d, J=15.9 Hz, 1H), 8.13 (d, J=4.5 Hz, 1H), 13.48 (br, 1H); APCI-MS (m/z) 423.14 (MH)$^+$.

Intermediate 9: 6-{(E)-2-[3-(Difluoromethoxy)-2-(pentyloxy)phenyl]vinyl}imidazo[2,1-b][1,3]thiazole-5-carboxylic acid

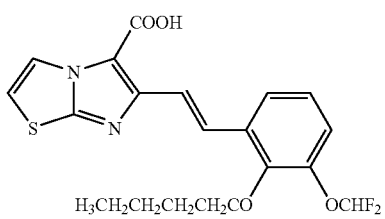

Step 1 Ethyl 6-{(E)-2-[3-(difluoromethoxy)-2-(pentyloxy)phenyl]vinyl}imidazo[2,1-b][1,3]thiazole-5-carboxylate: Alkylation of Intermediate 6 (400 mg, 1.052 mmol) with 1-bromopentane (157 mg, 1.262 mmol) in presence of potassium carbonate (160 mg, 1.157 mmol) in anhydrous N,N-dimethylformamide (4 mL) as described in Intermediate 7A gave 475 mg of the compound as a white solid; $^1$H NMR (300 MHz, DMSO-d$_6$) δ 0.90 (t, J=7.2 Hz, 3H), 1.30-1.40 (m, 5H), 1.44-1.52 (m, 2H), 1.72-1.78 (m, 2H), 3.93 (t, J=6.6 Hz, 2H), 4.40 (q, J=6.9 Hz, 2H), 7.19 (t, J=73.8 Hz, 1H), 7.21-7.30 (m, 2H), 7.43-7.49 (m, 1H), 7.53-7.58 (m, 1H), 7.77 (d, J=16.2 Hz, 1H), 7.86 (d, J=16.2 Hz, 1H), 8.14 (d, J=4.2 Hz, 1H); ESI-MS (m/z) 451.19 (M+H)$^+$.

Step 2 6-{(E)-2-[3-(Difluoromethoxy)-2-(pentyloxy)phenyl]vinyl}imidazo[2,1-b][1,3]thiazole-5-carboxylic acid: Lithium hydroxide assisted hydrolysis of Step 1 intermediate (460 mg, 1.021 mmol) as described in Intermediate 1 affords 450 mg of the desired product as a white solid; $^1$H NMR (300 MHz, DMSO-d$_6$) δ 0.84-0.92 (m, 3H), 1.27-1.36 (m, 2H), 1.40-1.50 (m, 2H), 1.70-1.80 (m, 2H), 3.93 (t, J=6.6 Hz, 2H), 7.19 (t, J=71.4 Hz, 1H), 7.20-7.30 (m, 2H), 7.44 (s, 1H), 7.51-7.58 (m, 1H), 7.81 (s, 2H), 8.13 (d, J=4.5 Hz, 1H), 13.48 (br, 1H); APCI-MS (m/z) 423.15 (MH)$^+$.

Intermediate 10: 6-{(E)-2-[2-(Cyclobutylmethoxy)-3-(difluoromethoxy)phenyl]vinyl}imidazo[2,1-b][1,3]thiazole-5-carboxylic acid

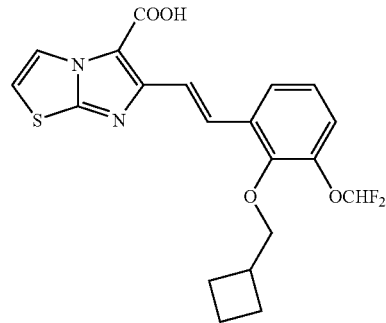

Step 1 Ethyl 6-{(E)-2-[2-(cyclobutylmethoxy)-3-(difluoromethoxy)phenyl]vinyl}imidazo[2,1-b][1,3]thiazole-5-carboxylate: Alkylation of Intermediate 6 (500 mg, 1.315 mmol) with (bromomethyl)cyclobutane (178 mg, 1.578 mmol) in presence of potassium carbonate (199 mg, 1.446 mmol) in anhydrous N,N-dimethylformamide (5 mL) as described in Intermediate 7A gave 520 mg of the product as a white solid; $^1$H NMR (300 MHz, DMSO-d$_6$) δ 1.40 (t, J=6.9 Hz, 3H), 1.84-1.93 (m, 4H), 2.02-2.10 (m, 2H), 2.70-2.76 (m, 1H), 3.93 (d, J=6.9 Hz, 2H), 4.41 (q, J=6.9 Hz, 2H), 7.19 (t, J=74.7 Hz, 1H), 7.20-7.28 (m, 2H), 7.42-7.51 (m, 1H), 7.54-7.60 (m, 1H), 7.70-7.78 (m, 1H), 7.85 (d, J=15.9 Hz, 1H), 8.13 (d, J=4.2 Hz, 1H); APCI-MS (m/z) 449.18 (M+H)$^+$.

Step 2 6-{(E)-2-[2-(Cyclobutylmethoxy)-3-(difluoromethoxy)phenyl]vinyl}imidazo[2,1-b][1,3]thiazole-5-carboxylic acid: Lithium hydroxide assisted hydrolysis of Step 1 intermediate (550 mg, 1.227 mmol) as described in Intermediate 1 gave 525 mg of the desired product as a white solid; $^1$H NMR (300 MHz, DMSO-d$_6$) δ 1.84-1.94 (m, 4H), 2.03-2.11 (m, 2H), 2.70-2.76 (m, 1H), 3.95 (d, J=6.9 Hz, 2H), 7.18 (t, J=75.6 Hz, 1H), 7.20-7.26 (m, 2H), 7.45 (s, 1H), 7.50-7.56 (m, 1H), 7.80 (s, 2H), 8.14 (d, J=4.5 Hz, 1H), 13.51 (br s, 1H); APCI-MS (m/z) 421.04 (MH)$^+$.

Intermediate 11: 2-[(E)-2-(2-(2,2-Dimethylpropoxy)-3-methoxyphenyl)vinyl]imidazo[1,2-c]pyridine-3-carboxylic acid

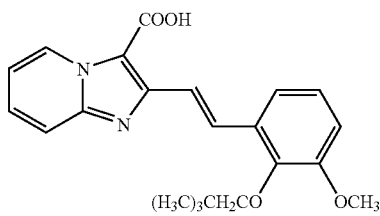

Step 1 Ethyl 2-methylimidazo[1,2-a]pyridine-3-carboxylate: To a stirred solution of 2-aminopyridine (15.0 g. 159.00 mmol) in dimethoxyethane (150 mL) was added NaHCO$_3$ (14.72 g, 175 mmol) followed by ethyl 2-chloroacetoacetate (39.34 g, 239 mmol) at room temperature. After refluxing for 16 h the solvent was removed under reduced pressure. The residue was taken up in water (200 mL) and extracted with dichloromethane (2×200 mL). The combined organic layers were washed with water (100 mL), brine (100 mL), and dried over anhydrous Na$_2$SO$_4$. Evaporation of solvents under reduced pressure afforded crude product which was further purified by column chromatography to give 20 g of the product as an off-white solid; $^1$H NMR (300 MHz, CDCl$_3$) δ 1.44 (t, J=6.9 Hz, 3H), 2.72 (s, 3H), 4.43 (q, J=7.2 Hz, 2H), 6.98 (t, J=6.6 Hz, 1H), 7.38 (t, J=8.7 Hz, 1H), 7.62 (d, J=8.7 Hz, 1H), 9.31 (d, J=6.9 Hz, 1H); ESI-MS (m/z) 205.13 (MH)$^+$.

Step 2 Ethyl 2-(bromomethyl)imidazo[1,2-a]pyridine-3-carboxylate: The Step 1 intermediate (7.20 g, 35.266 mmol) was brominated using N-bromosuccinimide (6.90 g, 38.793 mmol) in the presence of azobisisobutyronitrile (AIBN) (115 mg, 0.705 mmol) in carbon tetrachloride (200 mL) as described in Intermediate 1 gave 3.0 g of the product as a white solid; $^1$H NMR (300 MHz, CDCl$_3$) δ 1.49 (t, J=7.5 Hz, 3H), 4.49 (q, J=6.9 Hz, 2H), 4.93 (s, 2H), 7.05 (t, J=6.0 Hz, 1H), 7.45 (t, J=7.8 Hz, 1H), 7.70 (d, J=9.0 Hz, 1H), 9.31 (d, J=6.9 Hz, 1H); ESI-MS (m/z) 283.11 (MH)$^+$.

Step 3 3-Ethyloxycarbonylimidazo[1,2-a]pyridine-2-ylethyl(triphenyl)phosphonium bromide: The Step 2 intermediate (2.00 g, 7.063 mmol) was treated with triphenylphosphine (2.03 g, 7.770 mmol) in acetonitrile (75 mL) as described in Intermediate 1 afforded 4.0 g of product as an off-white solid; $^1$H NMR (300 MHz, CDCl$_3$) δ 1.31 (t, J=7.2 Hz, 3H), 4.29 (q, J =6.6 Hz, 2H), 5.57 (s, 1H), 5.62 (s, 1H), 7.30-7.33 (m, 1H), 7.42-7.55 (m, 2H), 7.67-7.68 (m, 6H), 7.75-7.82 (m, 9H), 9.07 (d, J=7.5 Hz, 1H); ESI-MS (m/z) 466.27 (MH)$^+$.

Step 4 Ethyl 2-{(E)-2-[2-(2,2-dimethylpropoxy)-3-methoxyphenyl]vinyl}imidazo[1,2-a]pyridine-3-carboxylate: This compound was prepared by the reaction of Step 3 intermediate (1.30 g, 2.383 mmol) with 2-(2,2-dimethylpropoxy)-3-methoxybenzaldehyde (0.582 g, 2.622 mmol) in the presence of NaH (104 mg, 2.621 mmol) in anhydrous DMSO (10 mL) to afford 0.712 g of the product as an off-white solid; $^1$H NMR (300 MHz, CDCl$_3$) δ 1.13 (s, 9H), 1.53 (t, J=7.5 Hz, 3H), 3.65 (s, 2H), 3.86 (s, 3H), 4.48 (q, J=6.9 Hz, 2H), 6.87 (d, J=8.4 Hz, 1H), 6.95 (t, J=7.2 Hz, 1H), 7.06 (t, J=8.4 Hz, 1H), 7.28-7.31 (m, 1H), 7.39 (t, J=8.4 Hz, 1H), 7.65 (d, J=9.0 Hz, 1H), 7.89 (d, J=15.9 Hz, 1H), 8.23 (d, J=15.9 Hz, 1H), 9.33 (d, J=6.9 Hz, 1H); ESI-MS (m/z) 409.28 (MH)$^+$.

Step 5 2-[(E)-2-(2-(2,2-Dimethylpropoxy)-3-methoxyphenyl)vinyl]imidazo[1,2-a]pyridine-3-carboxylic acid: Lithium hydroxide assisted hydrolysis of Step 4 ester (700 mg, 1.713 mmol) as described in Intermediate 1 afforded 500 mg of product as a white solid; $^1$H NMR (300 MHz, CDCl$_3$) δ 1.12 (s, 9H), 3.66 (s, 2H), 3.86 (s, 3H), 6.87 (d, J=8.4 Hz, 1H), 6.87 (t, J=8.1 Hz, 1H), 6.98-7.08 (m, 2H), 7.35 (d, J=7.8 Hz, 1H), 7.45 (t, J=8.4 Hz, 1H), 7.74 (d, J=9.3 Hz, 1H), 7.98 (d, J=16.2 Hz, 1H), 8.27 (d, J=16.2 Hz, 1H), 9.37 (d, J=6.9 Hz, 1H); ESI-MS (m/z) 379.20 (M−H)$^-$.

Intermediate 12: Ethyl 2-{(E)-2-[3-(difluoromethoxy)-2-hydroxyphenyl]vinyl}imidazo[1,2-a]pyridine-3-carboxylate

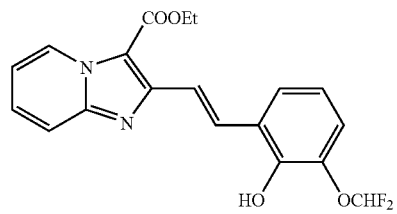

Step 1 Ethyl 2-{(E)-2-[2-(cyclopentyloxy)-3-(difluoromethoxy)phenyl]vinyl}imidazo [1,2-a]pyridine-3-carboxylate: Prepared by the reaction of 2-(cyclopentyloxy)-3-(difluoromethoxy)benzaldehyde (3.595 g, 14.040 mmol) with 3-ethyloxycarbonylimidazo[1,2-a]pyridine-2-yl-methyl(triphenyl)phosphonium bromide (7.0 g, 12.763 mmol) in the presence of NaH (0.561 g, 23.375 mmol) in anhydrous DMSO (15 mL) to afford 4.325 g of the product as an off-white solid; $^1$H NMR (300 MHz, DMSO-d$_6$) δ 1.44 (t, J=6.9 Hz, 3H), 1.55-1.61 (m, 2H), 1.67-1.75 (m, 2H), 1.84-1.93 (m, 4H), 4.40-4.50 (m, 2H), 4.72-4.78 (m, 1H), 7.20 (t, J=74.7 Hz, 1H), 7.22-7.30 (m, 3H), 7.55-7.65 (m, 2H), 7.75 (d, J=8.7 Hz, 1H), 7.91 (d, J=16.8 Hz, 1H), 8.05 (d, J=16.2 Hz, 1H), 8.24 (d, J=5.1 Hz, 1H); APCI-MS (m/z) 443.28 (M)$^+$.

Step 2 Ethyl 2-{(E)-2-[3-(difluoromethoxy)-2-hydroxyphenyl]vinyl}imidazo[1,2-a]pyridine-3-carboxylate: The Step 1 intermediate (4.3 g, 9.674 mmol) was treated with 48% hydrobromic acid (20 mL) in glacial AcOH (20 mL) as described in Intermediate 6 gave 3.1 g of the product as white solid; $^1$H NMR (300 MHz, DMSO-d$_6$) δ 1.44 (t, J=7.2 Hz, 3H), 4.44 (q, J=7.2 Hz, 2H), 6.92 (d, J=7.8 Hz, 1H), 7.12 (t, J=74.1 Hz, 1H), 7.15-7.22 (m, 2H), 7.48 (d, J=7.8 Hz, 1H), 7.57 (t, J=7.8 Hz, 1H), 7.75 (d, J=9.3 Hz, 1H), 7.95 (d, J=16.2 Hz, 1H), 8.08 (d, J=15.9 Hz, 1H), 9.24 (d, J=6.9 Hz, 1H), 9.83 (br, 1H); APCI-MS (m/z) 375.16 (MH)$^+$.

Intermediate 13: 2-{(E)-2-[2-(2,2-Dimethylpropoxy)-3-(difluoromethoxy)phenyl]vinyl}imidazo[1,2-a]pyridine-3-carboxylic acid

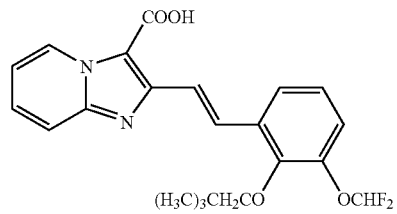

Step 1 Ethyl 2-{(E)-2-[2-(2,2-Dimethylpropoxy)-3-difluoromethoxy)phenyl]vinyl}imidazo[1,2-a]pyridine-3-carboxylate: Alkylation of Intermediate 12 (1.8 g, 4.811 mmol) with 1-bromo-2,2-dimethylpropane (1.83 ml, 14.434 mmol) in presence of cesium carbonate (3.135 g, 9.622 mmol) in anhydrous N,N-dimethylformamide (10 mL) as described in Intermediate 7A, Step 1 gave 1.56 g of the product as a white solid; $^1$H NMR (300 MHz, DMSO-$d_6$) δ 1.09 (s, 9H), 1.43 (t, J=7.5 Hz, 3H), 3.59 (s, 2H), 4.44 (q, J=7.2 Hz, 2H), 7.10-7.16 (m, 1H), 7.18 (t, J=72.3 Hz, 1H), 7.19-7.26 (m, 2H), 7.53-7.65 (m, 2H), 7.70 (d, J=9.3 Hz, 1H), 7.90 (d, J=16.2 Hz, 1H), 8.10 (d, J=16.2 Hz, 1H), 9.23 (d, J=6.6 Hz, 1H); APCI-MS (m/z) 445.21 (MH)$^+$.

Step 2 2-{(E)-2-[2-(2,2-Dimethylpropoxy)-3-(difluoromethoxy)phenyl]vinyl}imidazo[1,2-a]pyridine-3-carboxylic acid: Lithium hydroxide assisted hydrolysis of Step 1 intermediate (1.5 g, 3.376 mmol) as described in Intermediate 1 gave 1.45 g of the desired product as a white solid; $^1$H NMR (300 MHz, DMSO-$d_6$) δ 1.08 (s, 9H), 3.59 (s, 2H), 7.10-7.17 (m, 1H), 7.19 (t, J=74.1 Hz, 1H), 7.21-7.30 (m, 2H), 7.50-7.60 (m, 2H), 7.68 (d, J=8.7 Hz, 1H), 7.93 (d, J=16.2 Hz, 1H), 8.07 (d, J=16.5 Hz, 1H), 9.30 (d, J=6.9 Hz, 1H), 13.48 (br, 1H); APCI-MS (m/z) 415.10 (M−H)$^−$.

Intermediate 14: 2-{(E)-2-[3-(Difluoromethoxy)-2-(3-methylbutoxy)phenyl]vinyl}imidazo[1,2-c]pyridine-3-carboxylic acid

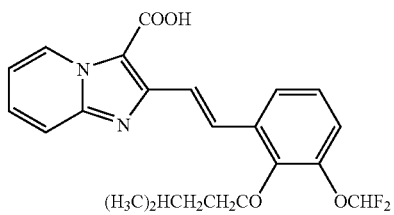

Step 1 Ethyl 2-{(E)-2-[3-(Difluoromethoxy)-2-(3-methylbutoxy)phenyl]vinyl}imidazo[1,2-a]pyridine-3-carboxylate: Alkylation of Intermediate 12 (400 mg, 1.069 mmol) with 1-bromo-3-methylbutane (193.8 mg, 1.283 mmol) in presence of potassium carbonate (163 mg, 1.175 mmol) in anhydrous N,N-dimethylformamide (4 mL) as described in Intermediate 7A, Step 1 gave 480 mg of the compound as a white solid; $^1$H NMR (300 MHz, DMSO-$d_6$) δ 0.94 (d, J=6.9, 6H), 1.40-1.47 (m, 3H), 1.64-1.71 (m, 2H), 1.88-1.95 (m, 1H), 3.97-4.03 (m, 2H), 4.40-4.48 (m, 2H), 7.12-7.20 (m, 2H), 7.21 (t, J=74.7 Hz, 1H), 7.22-7.28 (m, 1H), 7.53-7.62 (m, 2H), 7.74 (d, J=8.4 Hz, 1H), 7.94 (d, J=15.9 Hz, 1H), 8.04 (d, J=16.2 Hz, 1H), 9.23 (d, J=6.3 Hz, 1H); ESI-MS (m/z) 445.25 (M)$^+$.

Step 2 2-{(E)-2-[3-(Difluoromethoxy)-2-(3-methylbutoxy)phenyl]vinyl}imidazo[1,2-c]pyridine-3-carboxylic acid: Lithium hydroxide (173 mg, 4.054 mmol) assisted hydrolysis of Step 1 intermediate (450 mg, 1.013 mmol) as described in Intermediate 1 gave 400 mg of the desired product as a white solid; $^1$H NMR (300 MHz, DMSO-$d_6$) δ 0.94 (d, J=6.9, 6H), 1.65-1.75 (m, 2H), 1.85-1.93 (m, 1H), 3.95-4.01 (m, 2H), 7.10-7.17 (m, 2H), 7.20 (t, J=75.6 Hz, 1H), 7.22-7.28 (m, 1H), 7.53-7.60 (m, 2H), 7.72 (d, J=8.7 Hz, 1H), 7.96-8.02 (m, 2H), 9.30 (d, J=6.3 Hz, 1H), 13.47 (br, 1H); APCI-MS (m/z) 417.22 (MH)$^+$.

EXAMPLES

General Procedure for the Preparation of Amide Derivatives
Method A
Step 1: To a well stirred and cooled (0° C.) suspension of (E)-phenylvinyl carboxylic acid intermediates (1.0 equiv) in anhydrous dichloromethane (5 volume) was added catalytic amount of anhydrous N,N-dimethylformamide, followed by oxalyl chloride (2.0 equiv). The reaction mixture was stirred at the same temperature for 30 minutes. The reaction mixture was warmed gradually to room temperature and further stirred for 1 h. Excess oxalyl chloride and dichloromethane was evaporated under reduced pressure and the crude acid chloride obtained was directly used for the next step.

Step 2: To a stirred and cooled (0° C.) solution of acid chloride (1.0 equiv) in anhydrous dichloromethane (5 volume), was added appropriate amine derivative (1.0 equiv) followed by triethylamine (2.2 equiv). The resulting mixture was stirred overnight at room temperature. Excess of solvent was evaporated and obtained crude was purified by silica gel column chromatography using acetone in chloroform to obtain the product as white to off-white solid.
Method B
To a stirred solution of carboxylic acid derivative (1.0 equiv) in a 4:1 mixture of dichloromethane and N,N-dimethylformamide (5 volume) or in a 1:1 mixture of tetrahydrofuran and N,N-dimethylformamide (5 volume) was added EDCI (2.0 equiv) and DMAP (1.5 equiv) and the mixture was stirred for 30 min. An appropriate amine (1.0 equiv) was added and mixture was stirred for another 18 h. Solvent was evaporated and the residue obtained was diluted with ethyl acetate and water. The layers were separated. The aqueous layer was extracted with ethyl acetate and the combined ethyl acetate extracts were washed with brine and dried (Na$_2$SO$_4$). The solvent was evaporated and the residue obtained was purified by silica gel column chromatography to afford the desired product.

Example 1

6-[(E)-2-(2-Cyclopropylmethoxy-3-methoxyphenyl)vinyl]-N-[4-(trifluoromethoxy)phenyl]imidazo[2,1-b][1,3]thiazole-5-carboxamide

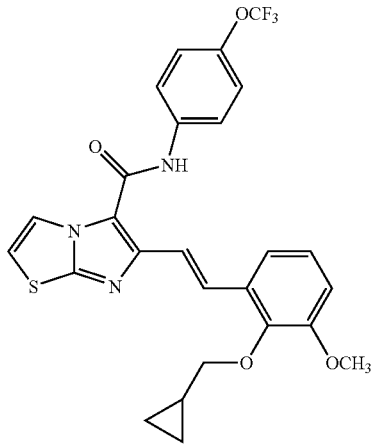

The title compound was prepared according to the general procedure (Method B) by coupling Intermediate 1 (95 mg, 0.256 mmol) with 4-(trifluoromethoxy)aniline (54 mg, 0.307 mmol) in the presence of EDCI hydrochloride (98 mg, 0.512 mmol) and DMAP (47 mg, 0.384 mmol) in a mixture of DCM and DMF (4:1, 5 mL) to give 68 mg of the product as an off-white solid; $^1$H NMR (300 MHz, DMSO-$d_6$) δ 0.23-0.26 (m, 2H), 0.43-0.47 (m, 2H), 1.13-1.15 (m, 1H), 3.73 (d, J=6.6

Hz, 2H), 3.78 (s, 3H), 6.92-6.96 (m, 1H), 7.04 (t, J=7.8 Hz, 1H), 7.22-7.25 (m, 1H), 7.35-7.38 (m, 3H), 7.44 (d, J=16.2 Hz, 1H), 7.77-7.81 (m, 2H), 7.86 (d, J=16.2 Hz, 1H), 8.01 (d, J=4.2 Hz, 1H), 10.47 (s, 1H); ESI-MS (m/z) 530.37 (MH)+.

Example 2

6-[(E)-2-(2-Cyclopropylmethoxy-3-methoxyphenyl)vinyl]-N-[4-(trifluoromethyl)-1,3-thiazol-2-yl]imidazo[2,1-b][1,3]thiazole-5-carboxamide

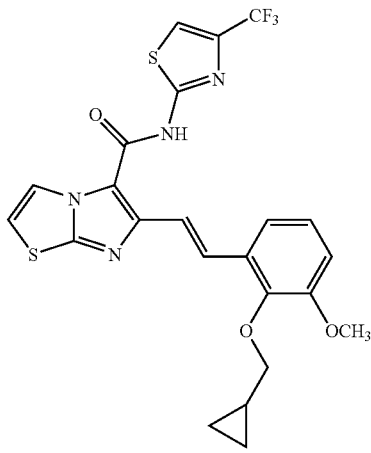

The title compound was prepared according to the general procedure (Method B) by coupling Intermediate 1 (200 mg, 0.539 mmol) with 4-(trifluoromethyl)-1,3-thiazol-2-amine (100 mg, 0.593 mmol) in the presence of EDCI hydrochloride (206 mg, 1.079 mmol) and DMAP (99 mg, 0.809 mmol) in a mixture of DCM and DMF (4:1, 5 mL) to give 72 mg of the product as an off-white solid; $^1$H NMR (300 MHz, DMSO-$d_6$) δ 0.24-0.26 (m, 2H), 0.47-0.49 (m, 2H), 1.15-1.18 (m, 1H), 3.75 (d, J=6.9 Hz, 2H), 3.79 (s, 3H), 6.96-6.99 (m, 1H), 7.09 (t, J=7.8 Hz, 1H), 7.30-7.33 (m, 1H), 7.40-7.42 (m, 1H), 7.46 (d, J=15.6 Hz, 1H), 7.87 (d, J=15.6 Hz, 1H), 8.03 (s, 1H), 8.06 (d, J=4.2 Hz, 1H), 12.94 (s, 1H); ESI-MS (m/z) 521.34 (MH)+.

Example 3

1-({6-[(E)-2-(2-Cyclopropylmethoxy-3-methoxyphenyl)vinyl]imidazo[2,1-b][1,3]thiazol-5-yl}carbonyl)-1,2,3,4-tetrahydroquinoline

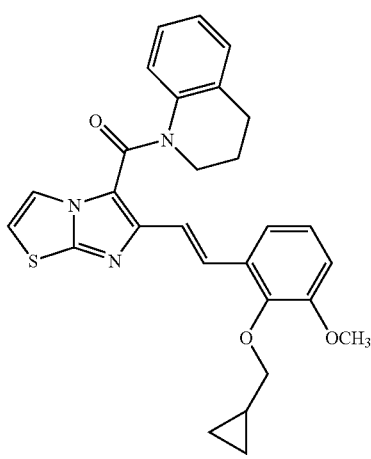

The title compound was prepared according to the general procedure (Method A) by coupling Intermediate 1 (100 mg, 0.269 mmol) with 1,2,3,4-tetrahydroquinoline (39 μL, 0.296 mmol) in the presence of triethylamine (68 mg, 0.674 mmol) in dichloromethane (5 mL) gave 79 mg of the product as an off-white solid; $^1$H NMR (300 MHz, DMSO-$d_6$) δ 0.21-0.22 (m, 2H), 0.45-0.47 (m, 2H), 1.09-1.11 (m, 1H), 1.97-2.00 (m, 2H), 2.85-2.87 (m, 2H), 3.66 (d, J=6.6 Hz, 2H), 3.76 (s, 3H), 3.83-3.85 (m, 2H), 6.75 (d, J=16.2 Hz, 1H), 6.85-6.93 (m, 4H), 6.98-7.03 (m, 2H), 7.13-7.15 (m, 1H), 7.26 (d, J=4.2 Hz, 1H), 7.56 (s, 1H), 7.61-7.64 (m, 1H); ESI-MS (m/z) 486.45 (MH)+.

Example 4

6-[(E)-2-(2-Cyclopropylmethoxy-3-methoxyphenyl)vinyl]imidazo[2,1-b][1,3]thiazol-5-yl-4-(5-trifluoromethyl-2-pyridyl)piperazinomethanone

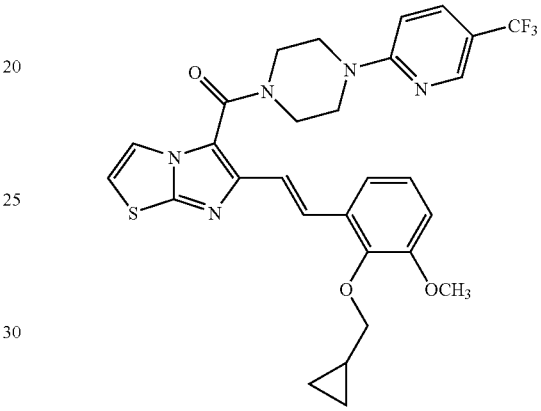

The title compound was prepared according to the general procedure (Method A) by coupling Intermediate 1 (50 mg, 0.134 mmol) with 1-[5-(trifluoromethyl)pyridin-2-yl]piperazine in the presence of triethylamine (34 mg, 0.337 mmol) in dichloromethane (5 mL) gave 46 mg of the product as an off-white solid; $^1$H NMR (300 MHz, CDCl$_3$) δ 0.25-0.29 (m, 2H), 0.52-0.58 (m, 2H), 1.25-1.28 (m, 1H), 3.72-3.74 (m, 4H), 3.78-3.82 (m, 6H), 3.83 (s, 3H), 6.61 (d, J=9.0 Hz, 1H), 6.79-6.82 (m, 1H), 6.87-6.88 (m, 1H), 7.00 (t, J=7.8 Hz, 1H), 7.09-7.12 (m, 1H), 7.19-7.22 (m, 1H), 7.61-7.63 (m, 1H), 7.74 (d, J=3.9 Hz, 1H), 7.80 (d, J=15.9 Hz, 1H), 8.36 (br s, 1H); ESI-MS (m/z) 584.35 (MH)+.

Example 5

6-(4-{6-(E)-2-(2-Cyclopropylmethoxy-3-methoxyphenyl)-1-ethenyl]imidazo[2,1-b][1,3]thiazol-5-ylcarbonyl}piperazino)nicotinonitrile

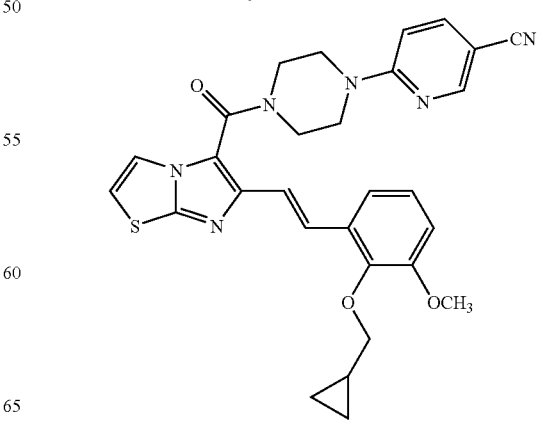

The title compound was prepared according to the general procedure (Method A) by coupling Intermediate 1 (50 mg, 0.134 mmol) with 6-piperazin-1-ylnicotinonitrile (33 mg, 0.148 mmol) in the presence of triethylamine (34 mg, 0.337 mmol) in dichloromethane (5 mL) gave 68 mg of the product as an off-white solid; $^1$H NMR (300 MHz, DMSO-$d_6$) δ 0.25-0.27 (m, 2H), 0.50-0.52 (m, 2H), 1.16-1.17 (m, 1H), 3.33-3.60 (m, 2H), 3.69-3.75 (m, 8H), 3.77 (s, 3H), 6.92-6.98 (m, 2H), 7.03 (t, J=7.8 Hz, 1H), 7.13 (d, J=16.2 Hz, 1H), 7.29-7.34 (m, 1H), 7.74-7.82 (m, 2H), 8.05-8.09 (m, 2H), 8.39-8.40 (m, 1H); ESI-MS (m/z) 541.33 (MH)$^+$.

Example 6

6-{(E)-2-[2-(Isobutoxy)-3-methoxyphenyl]vinyl}-N-[4-(trifluoromethyl)-1,3-thiazol-2-yl]imidazo[2,1-b][1,3]thiazole-5-carboxamide

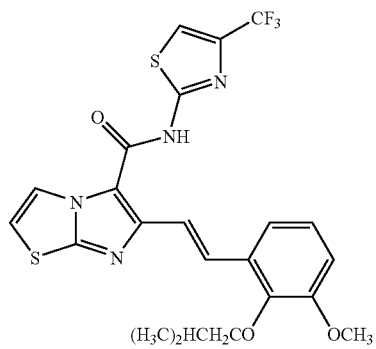

The title compound was prepared according to the general procedure (Method B) by coupling Intermediate 2 (150 mg, 0.403 mmol) with 4-(trifluoromethyl)-1,3-thiazol-2-amine (79 mg, 0.484 mmol) in the presence of EDCI hydrochloride (154 mg, 0.807 mmol) and DMAP (73 mg, 0.605 mmol) in a mixture of DCM and DMF (4:1, 5 mL) to give 10 mg of the product as an off-white solid; $^1$H NMR (300 MHz, DMSO-$d_6$) δ 0.97 (d, J=6.3 Hz, 6H), 1.98-2.04 (m, 2H), 3.65-3.71 (m, 2H), 3.81 (s, 3H), 6.97-7.03 (m, 1H), 7.07-7.14 (m, 1H), 7.30-7.36 (m, 1H), 7.42-7.52 (m, 2H), 7.83 (d, J=16.2 Hz, 1H), 7.97-8.07 (m, 2H), 13.00 (br s, 1H); APCI-MS (m/z) 523.12 (MH)$^+$.

Example 7

6-{(E)-2-[2-(2,2-Dimethylpropoxy)-3-methoxyphenyl]vinyl}-N-[4-(trifluoromethyl)-1,3-thiazol-2-yl]imidazo[2,1-b][1,3]thiazole-5-carboxamide

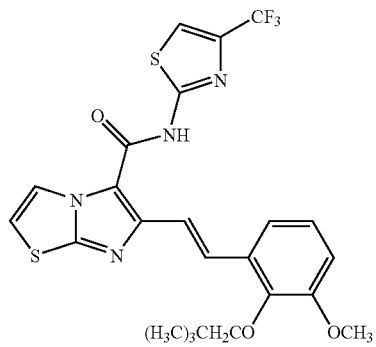

The title compound was prepared according to the general procedure (Method B) by coupling Intermediate 3 (200 mg, 0.517 mmol) with 4-(trifluoromethyl)-1,3-thiazol-2-amine (105 mg, 0.621 mmol) in the presence of EDCI hydrochloride (198 mg, 1.035 mmol) and DMAP (95 mg, 0.776 mmol) in a mixture of DCM and DMF (4:1, 5 mL) to give 114 mg of the product as a pale yellow solid; $^1$H NMR (300 MHz, DMSO-$d_6$) δ 1.01 (s, 9H), 3.56 (s, 2H), 3.80 (s, 3H), 6.98-6.99 (m, 1H), 7.11 (t, J=7.8 Hz, 1H), 7.34 (d, J=7.8 Hz, 1H), 7.43-7.48 (m, 2H), 7.85 (d, J=16.2 Hz, 1H), 8.05-8.09 (m, 2H), 12.97 (br s, 1H); ESI-MS (m/z) 535.20 (M–H)$^-$.

Example 8

6-{(E)-2-[2-(2,2-Dimethylpropoxy)-3-methoxyphenyl]vinyl}-N-[4-(tert-butyl)-1,3-thiazol-2-yl]imidazo[2,1-b][1,3]thiazole-5-carboxamide

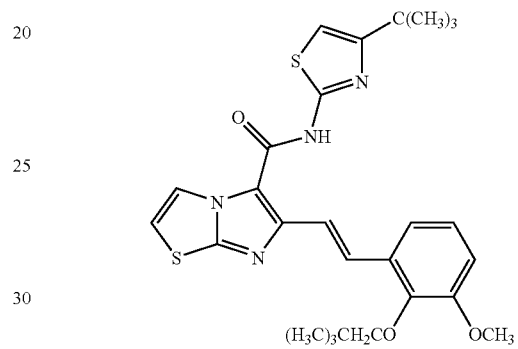

The title compound was prepared according to the general procedure (Method B) by coupling Intermediate 3 (150 mg, 0.388 mmol) with 4-tert-butyl-1,3-thiazol-2-amine (72 mg, 0.465 mmol) in the presence of EDCI hydrochloride (148 mg, 0.776 mmol) and DMAP (71 mg, 0.582 mmol) in a mixture of DCM and DMF (4:1, 10 mL) to give 70 mg of the product as an off-white solid; $^1$H NMR (300 MHz, DMSO-$d_6$) δ 1.06 (s, 9H), 1.33 (s, 9H), 3.57 (s, 2H), 3.80 (s, 3H), 6.58 (s, 1H), 6.98 (d, J=8.1 Hz, 1H), 7.10 (t, J=7.8 Hz, 1H), 7.32-7.34 (m, 1H), 7.41 (d, J=4.5 Hz, 1H), 7.87 (d, J=16.8 Hz, 1H), 8.11 (d, J=16.5 Hz, 1H), 8.79 (d, J=3.9 Hz, 1H), 12.68 (br s, 1H); ESI-MS (m/z) 525.43 (MH)$^+$.

Example 9

6-{(E)-2-[2-(2,2-Dimethylpropoxy)-3-methoxyphenyl]vinyl}-N-4-(tert-butyl)-1,3-thiazol-2-yl]imidazo[2,1-b][1,3]thiazole-5-carboxamide sodium salt

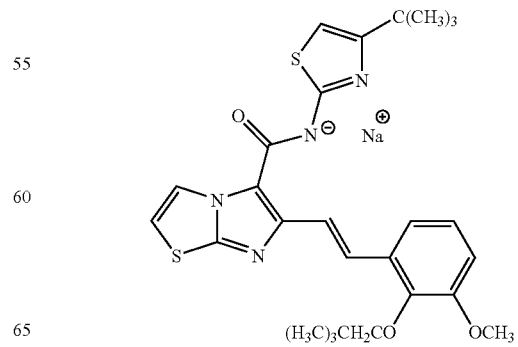

To a stirred solution of Example 8 (30 mg, 0.057 mmol) in ethanol (1.5 mL) was added sodium ethoxide (4.2 mg, 0.062 mmol) at room temperature. Resulting mixture was stirred for 1 h at the same temperature and then refluxed for another 1 h. Solvent was evaporated under vacuum and the residue was triturated with diethyl ether and hexane. The solid obtained was collected by filtration to give 19 mg of the product as a yellow solid; $^1$H NMR (300 MHz, DMSO-d$_6$) δ 1.07 (s, 9H), 1.25 (s, 9H), 3.56 (s, 2H), 3.80 (s, 3H), 6.22 (s, 1H), 6.92 (d, J=7.8 Hz, 1H), 7.08 (t, J=7.8 Hz, 1H), 7.22-7.30 (m, 2H), 7.70 (d, J=16.2 Hz, 1H), 8.31 (d, J=16.8 Hz, 1H), 8.79 (d, J=4.2 Hz, 1H); ESI-MS (m/z) 523.40 (M–H)$^-$.

Example 10

6-{(E)-2-[2-(2,2-Dimethylpropoxy)-3-methoxyphenyl]vinyl}-N-(4-methyl-1,3-thiazol-2-yl)imidazo[2,1-b][1,3]thiazole-5-carboxamide

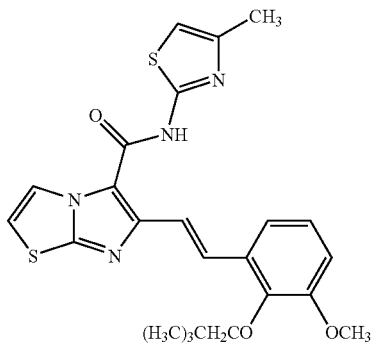

The title compound was prepared according to the general procedure (Method B) by coupling Intermediate 3 (250 mg, 0.646 mmol) with 4-methyl-1,3-thiazol-2-amine (82 mg, 0.711 mmol) in the presence of EDCI hydrochloride (247 mg, 1.292 mmol) and DMAP (36.33 mg, 0.323 mmol) in a mixture of DCM and DMF (4:1, 10 mL) to give 110 mg of the product as an off-white solid; $^1$H NMR (300 MHz, DMSO-d$_6$) δ 1.06 (s, 9H), 2.28 (s, 3H), 3.57 (s, 2H), 3.80 (s, 3H), 6.62 (s, 1H), 6.98 (d, J=7.8 Hz, 1H), 7.11 (t, J=7.8 Hz, 1H), 7.36-7.40 (m, 2H), 7.88 (d, J=16.2 Hz, 1H), 7.98-8.20 (br m, 1H), 8.55 (br m, 1H), 12.89 (br s, 1H); ESI-MS (m/z) 483.33 (MH)$^+$.

Example 11

N-Ethyl-6-{(E)-2-[2-(2,2-dimethylpropoxy)-3-methoxyphenyl]vinyl}-N-[4-(trifluoro-methyl)-1,3-thiazol-2-yl]imidazo[2,1-b][1,3]thiazole-5-carboxamide

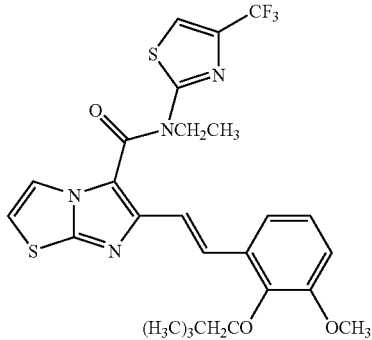

To a stirred solution of Example 7 (80 mg, 0.149 mmol) in anhydrous N,N-dimethylformamide (2.0 mL) was added K$_2$CO$_3$ (41 mg, 0.298 mmol) followed by iodoethane (0.018 mL, 0.223 mmol) at room temperature. Resulting suspension was stirred at 80° C. for 18 h under nitrogen atmosphere. The reaction mixture was diluted with ethyl acetate (100 mL) and water (50 mL). The layers were separated. Aqueous layer was extracted with ethyl acetate (2×25 mL) and the combined organic layers were washed with brine (2×25 mL), dried (Na$_2$SO$_4$) and filtered. The filtrate was concentrated under reduced pressure. The residue obtained after the evaporation of the solvent was purified by silica gel column chromatography using 2% ethyl acetate in petroleum ether to obtain 20 mg of the product as an off-white solid; $^1$H NMR (300 MHz, CDCl$_3$) δ 1.11 (s, 9H), 1.49 (t, J=6.9 Hz, 3H), 3.65 (s, 2H), 3.86 (s, 3H), 4.44 (q, J=6.9 Hz, 2H), 6.83-6.89 (m, 2H), 7.02 (t, J=7.8 Hz, 1H), 7.19 (s, 1H), 7.28-7.30 (m, 1H), 8.05 (d, J=16.5 Hz, 1H), 8.23 (d, J=15.9 Hz, 1H), 8.48 (d, J=4.5 Hz, 1H); ESI-MS (m/z) 565.35 (MH)$^+$.

Example 12

6-{(E)-2-[2-(2,2-Dimethylpropoxy)-3-methoxyphenyl]vinyl}-N-[5-(trifluoromethyl)-1,3,4-thiadiazol-2-yl]imidazo[2,1-b][1,3]thiazole-5-carboxamide

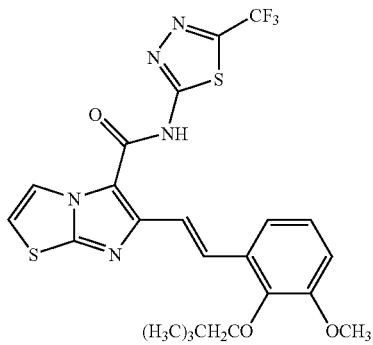

The title compound was prepared according to the general procedure (Method B) by coupling Intermediate 3 (150 mg, 0.388 mmol) with 5-(trifluoromethyl)-1,3,4-thiadiazol-2-amine (78 mg, 0.465 mmol) in the presence of EDCI hydrochloride (148 mg, 0.776 mmol) and DMAP (71 mg, 0.582 mmol) in a mixture of DCM and DMF (4:1, 10 mL) to give 80 mg of the product as an off-white solid; $^1$H NMR (300 MHz, CDCl$_3$) δ 1.02 (s, 9H), 3.56 (s, 2H), 3.83 (s, 3H), 6.79-6.82 (m, 2H), 6.84-6.94 (m, 2H), 7.28 (d, J=16.5 Hz, 1H), 7.66 (d, J=15.9 Hz, 1H), 8.11 (d, J=4.5 Hz, 1H); ESI-MS (m/z) 538.27 (MH)$^+$.

Example 13

6-{[(E)-2-(2,2-Dimethylpropoxy)-3-methoxyphenyl]vinyl}-N-[4-(trifluoromethyl)-1,3-oxazol-2-yl]imidazo[2,1-b][1,3]thiazole-5-carboxamide

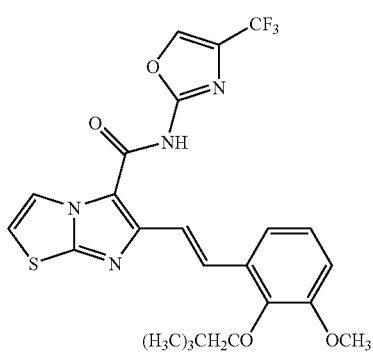

The title compound was prepared according to the general procedure (Method B) by coupling Intermediate 3 (150 mg, 0.388 mmol) with 4-(trifluoromethyl)-1,3-oxazol-2-amine (70 mg, 0.465 mmol) in the presence of EDCI hydrochloride (148 mg, 0.776 mmol) and DMAP (71 mg, 0.582 mmol) in a mixture of DCM and DMF (4:1, 10 mL) to give 15 mg of the product as an off-white solid; ¹H NMR (300 MHz, DMSO-d₆) δ 1.04 (s, 9H), 3.56 (s, 2H), 3.79 (s, 3H), 6.99 (d, J=7.8 Hz, 1H), 7.08 (t, J=7.8 Hz, 1H), 7.33 (d, J=7.8 Hz, 1H), 7.43-7.47 (m, 2H), 7.90 (d, J=15.6 Hz, 1H), 8.08 (d, J=3.9 Hz, 1H), 8.75 (s, 1H), 11.99 (br s, 1H); ESI-MS (m/z) 521.12 (MH)⁺.

Example 14

6-[(E)-2-(2,2-Dimethylpropoxy)-3-methoxyphenyl)vinyl]imidazo[2,1-b][1,3]thiazol-5-yl-3-trifluoromethyl-5,6,7,8-tetrahydro[1,2,4]triazolo[4,3-a]pyrazin-7-ylmethanone

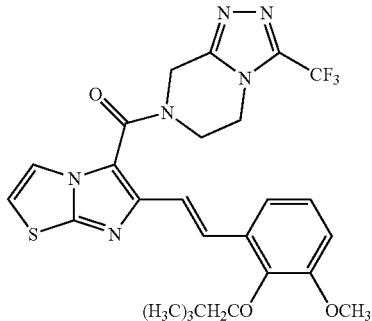

The title compound was prepared according to the general procedure (Method B) by coupling Intermediate 3 (100 mg, 0.258 mmol) with 3-(trifluoromethyl)-5,6,7,8-tetrahydro[1,2,4]triazolo[4,3-a]pyrazine hydrochloride (65 mg, 0.284 mmol) in the presence of EDCI hydrochloride (99 mg, 0.517 mmol) and DMAP (58 mg, 0.517 mmol) in a mixture of DCM and DMF (4:1, 10 mL) to give 85 mg of the product as an off-white solid; ¹H NMR (300 MHz, DMSO-d₆) δ 1.04 (s, 9H), 3.56 (s, 2H), 3.79 (s, 3H), 4.07 (br m, 2H), 4.24 (br m, 2H), 5.03 (s, 2H), 6.97-7.05 (m, 2H), 7.13 (d, J=15.6 Hz, 1H), 7.31 (d, J=6.0 Hz, 1H), 7.54 (d, J=4.5 Hz, 1H), 7.79-7.85 (m, 2H); ESI-MS (m/z) 561.38 (MH)⁺.

Example 15

N-[4-(4-Cyanophenyl)-1,3-thiazol-2-yl]-6-{(E)-2-[2-(2,2-dimethylpropoxy)-3-methoxyphenyl]vinyl}imidazo[2,1-b][1,3]thiazole-5-carboxamide

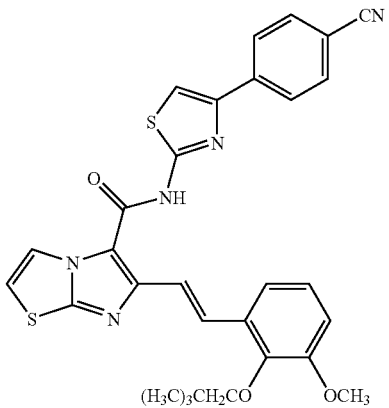

The title compound was prepared according to the general procedure (Method B) by coupling Intermediate 3 (130 mg, 0.336 mmol) with 4-(2-amino-1,3-thiazol-4-yl)benzonitrile (81 mg, 0.403 mmol) in the presence of EDCI hydrochloride (128 mg, 0.672 mmol) and DMAP (61 mg, 0.504 mmol) in a mixture of DCM and DMF (4:1, 5 mL) to give 27 mg of the product as an off-white solid; ¹H NMR (300 MHz, DMSO-d₆) δ 1.02 (s, 9H), 3.57 (s, 2H), 3.80 (s, 3H), 7.00 (d, J=8.4 Hz, 1H), 7.11 (t, J=7.8 Hz, 1H), 7.34 (d, J=7.2 Hz, 1H), 7.40-7.50 (m, 2H), 7.84 (s, 1H), 7.91-7.96 (m, 2H), 7.98-8.05 (m, 1H), 8.10-8.15 (m, 2H), 12.79 (br s, 1H); APCI-MS (m/z) 570.17 (MH)⁺.

Example 16

6-[(E)-2-(2-Cyclopentyloxy-3-methoxyphenyl)vinyl]-N-[4-(trifluoromethyl)-1,3-thiazol-2-yl]imidazo[2,1-b][1,3]thiazole-5-carboxamide

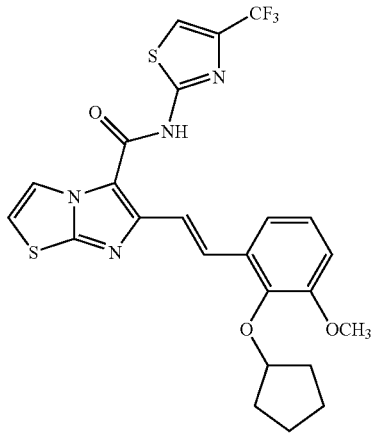

The title compound was prepared according to the general procedure (Method B) by coupling Intermediate 4 (200 mg, 0.520 mmol) with 4-(trifluoromethyl)-1,3-thiazol-2-amine (105 mg, 0.624 mmol) in the presence of EDCI hydrochloride (200 mg, 1.040 mmol) and DMAP (159 mg, 1.300 mmol) in a mixture of DCM and DMF (4:1, 5 mL) to give 86 mg of the product as an off-white solid; ¹H NMR (300 MHz, DMSO-d₆) δ 1.52-1.62 (m, 4H), 1.76-1.79 (m, 4H), 3.81 (s, 3H), 4.85 (br s, 1H), 7.00 (d, J=7.8 Hz, 1H), 7.10 (t, J=8.1 Hz, 1H), 7.34 (d, J=7.8 Hz, 1H), 7.43-7.49 (m, 2H), 7.82 (d, J=16.2 Hz, 1H), 8.06-8.10 (m, 2H), 12.99 (br s, 1H); ESI-MS (m/z) 535.11 (MH)⁺.

Example 17

6-{(E)-2-[2-Cyclopentyloxy-3-(difluoromethoxy)phenyl]vinyl}-N-[4-(trifluoromethyl)-1,3-thiazol-2-yl]imidazo[2,1-b][1,3]thiazole-5-carboxamide

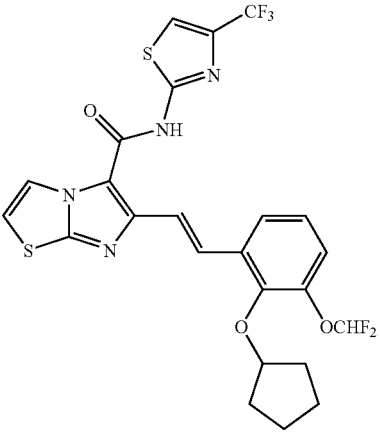

The title compound was prepared according to the general procedure (Method B) by coupling Intermediate 5 (365 mg, 0.868 mmol) with 4-(trifluoromethyl)-1,3-thiazol-2-amine (157 mg, 0.965 mmol) in the presence of EDCI hydrochloride (333 mg, 1.737 mmol) and DMAP (98 mg, 0.868 mmol) in a mixture of THF and DMF (1:1, 6 mL) to give 34 mg of the product as an off-white solid; $^1$H NMR (300 MHz, DMSO-$d_6$) δ 1.75-1.85 (m, 8H), 4.70-4.78 (m, 1H), 7.18 (t, J=74.7 Hz, 1H), 7.20-7.5 (m, 2H), 7.40-7.46 (m, 1H), 7.53 (d, J=15.9 Hz, 1H), 7.60-7.70 (m, 1H), 7.79 (d, J=15.0 Hz, 1H), 8.05-8.12 (m, 2H), 13.03 (br s, 1H); APCI-MS (m/z) 571.07 (MH)$^+$.

Example 18

6-{(E)-2-[3-Difluoromethoxy-2-(2,2-dimethylpropoxy)phenyl]vinyl}-N-[4-(trifluoro-methyl)-1,3-thiazol-2-yl]imidazo[2,1-b][1,3]thiazole-5-carboxamide

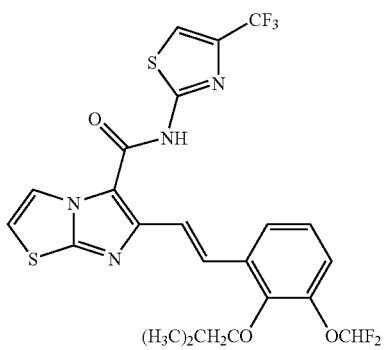

The title compound was prepared according to the general procedure (Method B) by coupling Intermediate 7A (270 mg, 0.639 mmol) with 4-(trifluoromethyl)-1,3-thiazol-2-amine (116 mg, 0.703 mmol) in the presence of EDCI hydrochloride (245 mg, 1.278 mmol) and DMAP (72 mg, 0.639 mmol) in a mixture of THF and DMF (1:1, 6 mL) to give 127 mg of the product as an off-white solid; $^1$H NMR (300 MHz, DMSO-$d_6$) δ 1.02 (s, 9H), 3.56 (s, 2H), 7.17 (t, J=74.1 Hz, 1H), 7.20-7.31 (m, 2H), 7.42-7.45 (m, 1H), 7.52 (d, J=15.9 Hz, 1H), 7.67-7.69 (m, 1H), 7.81 (d, J=16.2 Hz, 1H), 8.06-8.10 (m, 2H), 13.01 (br s, 1H); APCI-MS (m/z) 573.26 (MH)$^+$.

Alternatively, the title compound can be prepared by coupling Intermediate 7B (1.0 gm, 1.83 mmol) with 4-(trifluoromethyl)-1,3-thiazol-2-amine (0.34 gm, 0.202 mmol) in DMF (8.0 mL) and NaH 60% dispersion on mineral oil (0.165 gm, 4.12 mmole) was added at 0° C. and stirred for 30 minutes. The reaction mixture was quenched in water, acidified with acetic acid and filtered to yield solid product which was further purified by crystallization with toluene to afford 0.70 gm of product; $^1$H NMR (300 MHz, DMSO-d6) δ 1.03 (s, 9H), 3.56 (s, 2H), 7.16-7.22 (m, 2H), 7.40-7.55 (m, 3H), 7.62-7.70 (m, 1H), 7.82 (d, J=15.6 Hz, 1H), 8.04-8.10 (m, 2H), 13.02 (br s, 1H); APCI-MS (m/z) 573.26 (M+H)$^+$.

Example 19

6-[(E)-2-(2,3-Dihydroxyphenyl)vinyl]-N-[4-(trifluoromethyl)-1,3-thiazol-2-yl]imidazo[2,1-b][1,3]thiazole-5-carboxamide

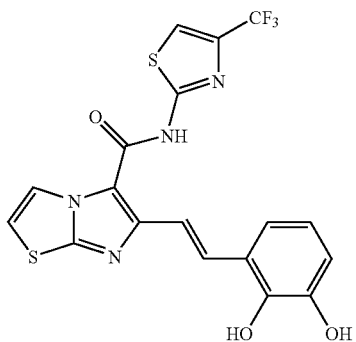

To a well stirred and cooled (−75° C.) suspension of Example 18 (300 mg, 0.524 mmol) in anhydrous dichloromethane (5 mL) was added drop-wise a solution of BBr$_3$ in anhydrous dichloromethane (394 mg, 1.573 mmol). The mixture was stirred at the same temperature for 30 minutes. The mixture was then gradually warmed to room temperature over a period of 2 h. The reaction mixture was neutralized with saturated solution of NaHCO$_3$ and extracted with ethyl acetate (2×100 mL). The combined organic extracts were washed with brine (100 mL) and dried (Na$_2$SO$_4$). The solvent was evaporated under reduced pressure to obtain 90 mg of the product as an off-white solid; $^1$H NMR (300 MHz, DMSO-$d_6$) δ 6.66-6.75 (m, 2H), 7.11 (d, J=7.2 Hz, 1H) 7.34-7.43 (m, 2H), 7.89 (d, J=15.6 Hz, 1H), 8.04-8.10 (m, 2H), 8.74 (s, 1H), 9.49 (s, 1H), 12.93 (br s, 1H); APCI-MS (m/z) 453.08 (MH)$^+$.

Example 20

6-{(E)-2-[2-(2,2-Dimethylpropoxy)-3-(difluoromethoxy)phenyl]vinyl}-N-(4-isopropyl-1,3-thiazol-2-yl)imidazo[2,1-b][1,3]thiazole-5-carboxamide

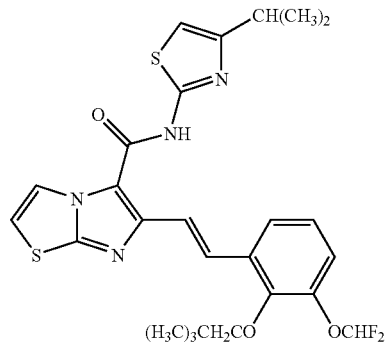

The title compound was prepared according to the general procedure (Method B) by coupling Intermediate 7A (100 mg, 0.236 mmol) with 4-(isopropyl)-1,3-thiazol-2-amine (41 mg, 0.260 mmol) in the presence of EDCI hydrochloride (90 mg, 0.472 mmol) and DMAP (26 mg, 0.236 mmol) in a mixture of THF and DMF (1:1, 4 mL) to give 60 mg of the product as an off-white solid; $^1$H NMR (300 MHz, DMSO-$d_6$) δ 1.07 (s, 9H), 1.26 (d, J=6.9 Hz, 6H), 2.92-2.98 (m, 1H), 3.57 (s, 2H), 6.64 (s, 1H), 7.18 (t, J=74.7 Hz, 1H), 7.20-7.30 (m, 2H), 7.42 (s, 1H), 7.64-7.70 (m, 1H), 7.83 (d, J=15.6 Hz, 1H), 8.12-8.18 (m, 1H), 8.60-8.70 (m, 1H), 12.86 (br s, 1H); APCI-MS (m/z) 547.26 (MH)$^+$.

Example 21

6-[(E)-2-(3-(Difluoromethoxy)-2-(2,2-dimethylpropoxy)-phenyl)vinyl]-N-(4-tert-butyl-1,3-thiazol-2-yl)imidazo[2,1-b][1,3]thiazole-5-carboxamide

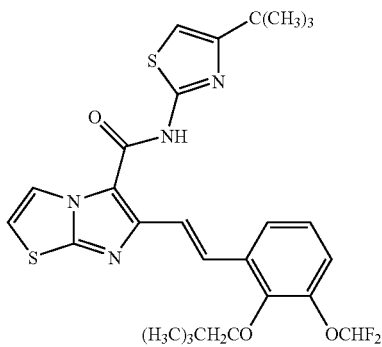

The title compound was prepared according to the general procedure (Method B) by coupling Intermediate 7 (100 mg, 0.236 mmol) with 4-(tert-butyl)-1,3-thiazol-2-amine (40 mg, 0.260 mmol) in the presence of EDCI hydrochloride (90 mg, 0.472 mmol) and DMAP (26 mg, 0.236 mmol) in a mixture of THF and DMF (1:1, 4 mL) to give 30 mg of the product as an off-white solid; $^1$H NMR (300 MHz, DMSO-$d_6$) δ 1.05 (s, 9H), 1.22 (s, 9H), 3.57 (s, 2H), 6.60-6.66 (m, 1H), 6.78-6.84 (m, 1H), 7.18 (t, J=75.0 Hz, 1H), 7.21-7.31 (m, 1H), 7.42 (s, 1H), 7.65 (d, J=6.9 Hz, 1H), 7.81 (d, J=15.6 Hz, 1H), 8.12-8.20 (m, 1H), 8.75-8.81 (m, 1H), 12.78 (br s, 1H); ESI-MS (m/z) 561.24 (MH)$^+$.

Example 22

6-{(E)-2-[2-(2,2-Dimethylpropoxy)-3-(difluoromethoxy)phenyl]vinyl}-N-(4-cyclobutyl-1,3-thiazol-2-yl)imidazo[2,1-b][1,3]thiazole-5-carboxamide

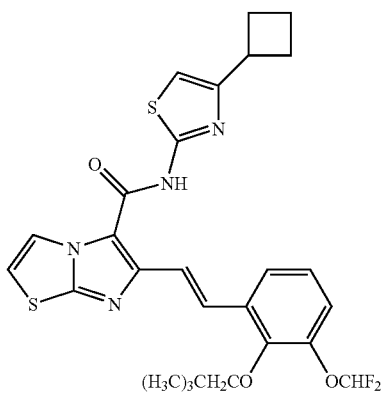

The title compound was prepared according to the general procedure (Method B) by coupling Intermediate 7A (100 mg, 0.236 mmol) with 4-(cyclobutyl)-1,3-thiazol-2-amine (40 mg, 0.260 mmol) in the presence of EDCI hydrochloride (90 mg, 0.472 mmol), DMAP (26 mg, 0.236 mmol) in a mixture of THF and DMF (1:1, 4 mL) to give 50 mg of the product as an off-white solid; $^1$H NMR (300 MHz, DMSO-$d_6$) δ 1.07 (s, 9H), 1.84-1.90 (m, 2H), 1.95-2.05 (m, 1H), 2.15-2.30 (m, 4H), 3.58 (s, 2H), 6.73 (s, 1H), 7.18 (t, J=75.0 Hz, 1H), 7.20-7.30 (m, 2H), 7.38-7.44 (m, 1H), 7.66-7.72 (m, 1H), 7.83 (d, J=16.2 Hz, 1H), 8.10-8.18 (m, 1H), 8.62-8.68 (m, 1H), 12.87 (br s, 1H); ESI-MS (m/z) 559.22 (MH)$^+$.

Example 23

6-{(E)-2-[2-(2,2-Dimethylpropoxy)-3-(difluoromethoxy)phenyl]vinyl}-N-(4-cyclo-propyl-1,3-thiazol-2-yl)imidazo[2,1-b][1,3]thiazole-5-carboxamide

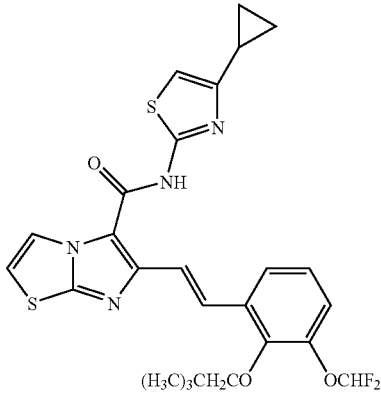

The title compound was prepared according to the general procedure (Method B) by coupling Intermediate 7A (100 mg, 0.236 mmol) with 4-(cyclopropyl)-1,3-thiazol-2-amine (36 mg, 0.260 mmol) in the presence of EDCI hydrochloride (90 mg, 0.472 mmol) and DMAP (26 mg, 0.236 mmol) in a mixture of THF and DMF (1:1, 4 mL) to give 40 mg of the product as an off-white solid; $^1$H NMR (300 MHz, DMSO-$d_6$) δ0.80-0.86 (m, 2H), 1.06 (s, 9H), 1.13-1.23 (m, 2H), 1.94-2.00 (m, 1H), 3.57 (s, 2H), 6.60-6.66 (m, 1H), 7.18 (t, J=74.7 Hz, 1H), 7.22-7.30 (m, 2H), 7.40-7.48 (m, 1H), 7.68 (d, J=7.5 Hz, 1H), 7.82 (d, J=15.6 Hz, 1H), 8.08-8.16 (m, 1H), 8.52-8.60 (m, 1H), 12.99 (br s, 1H); APCI-MS (m/z) 545.18 (MH)$^+$.

Example 24

6-{(E)-2-[3-(Difluoromethoxy)-2-(2,2-dimethylpropoxy)phenyl]vinyl}-N-(3-trifluoromethylphenyl)imidazo[2,1-b][1,3]thiazole-5-carboxamide

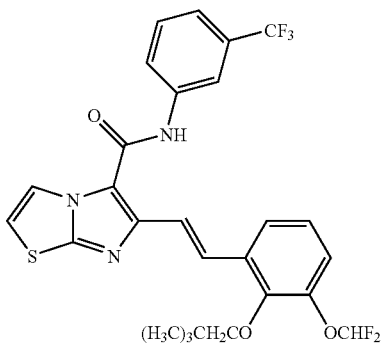

The title compound was prepared according to the general procedure (Method B) by coupling Intermediate 7A (80 mg, 0.189 mmol) with 3-trifluoromethyl)aniline (33 mg, 0.208 mmol) in the presence of EDCI hydrochloride (72 mg, 0.378 mmol), DMAP (21 mg, 0.189 mmol) in a mixture of THF and DMF (1:1, 4 mL) to give 25 mg of the product as an off-white solid; $^1$H NMR (300 MHz, DMSO-$d_6$) δ 1.02 (s, 9H), 3.54 (s, 2H), 7.10-7.18 (m, 3H), 7.38-7.51 (m, 3H), 7.57-7.63 (m, 2H), 7.82 (d, J=16.2 Hz, 1H), 7.89 (d, J=7.8 Hz, 1H), 8.02-8.08 (m, 1H), 8.17 (s, 1H), 10.58 (br s, 1H); ESI-MS (m/z) 566.28 (MH)$^+$.

Example 25

6-{(E)-2-[3-(Difluoromethoxy)-2-(2,2-dimethylpropoxy)phenyl]vinyl}-N-(3-trifluoro methylbenzyl)imidazo[2,1-b][1,3]thiazole-5-carboxamide

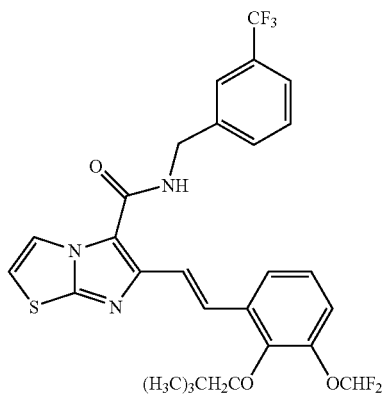

The title compound was prepared according to the general procedure (Method B) by coupling Intermediate 7A (100 mg, 0.236 mmol) with 1-[3-(trifluoromethyl)phenyl]methanamine (45.58 mg, 0.260 mmol) in the presence of EDCI hydrochloride (90 mg, 0.472 mmol) and DMAP (27 mg, 0.236 mmol) in a mixture of THF and DMF (1:1, 4 mL) to give 75 mg of the product as an off-white solid; $^1$H NMR (300 MHz, DMSO-$d_6$) δ 1.06 (s, 9H), 3.56 (s, 2H), 4.61 (s, 2H), 7.16 (t, J=75.3 Hz, 1H), 7.18-7.25 (m, 1H), 7.36-7.51 (m, 2H), 7.57-7.65 (m, 3H), 7.71-7.77 (m, 2H), 7.83 (d, J=15.6 Hz, 1H), 8.02-8.08 (m, 1H), 8.82-8.88 (m, 1H); APCI-MS (m/z) 580.29 (MH)$^+$.

Example 26

N-(5-Cyanopyridin-2-yl)-6-{(E)-2-[3-(difluoromethoxy)-2-(2,2-dimethylpropoxy)phenyl]vinyl}imidazo[2,1-b][1,3]thiazole-5-carboxamide

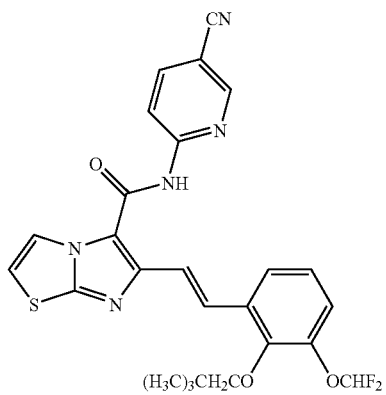

The title compound was prepared according to the general procedure (Method B) by coupling Intermediate 7A (80 mg, 0.189 mmol) with 6-aminonicotinonitrile (27 mg, 0.226 mmol) in the presence of EDCI hydrochloride (72 mg, 0.378 mmol), DMAP (22 mg, 0.189 mmol) in a mixture of THF and DMF (1:1, 4 mL) to give 25 mg of the product as an off-white solid; $^1$H NMR (300 MHz, DMSO-$d_6$) δ 1.03 (s, 9H), 3.56 (s, 2H), 7.17 (t, J=74.1 Hz, 1H), 7.19-7.25 (m, 2H), 7.42-7.50 (m, 2H), 7.55-7.62 (m, 1H), 7.82 (d, J=15.6 Hz, 1H), 8.02-8.08 (m, 1H), 8.18-8.24 (m, 1H), 8.28-8.35 (m, 1H), 8.83-8.90 (m, 1H), 11.39 (br s, 1H); APCI-MS (m/z) 524.25 (MH)$^+$.

Example 27

N-[3-Chloro-5-(trifluoromethyl)pyridin-2-yl]-6-{(E)-2-[3-(difluoromethoxy)-2-(2,2-dimethylpropoxy)phenyl]vinyl}imidazo[2,1-b][1,3]thiazole-5-carboxamide

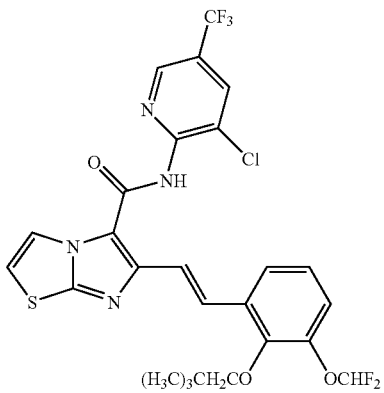

The title compound was prepared according to the general procedure (Method B) by coupling Intermediate 7A (100 mg, 0.236 mmol) with 3-chloro-5-(trifluoromethyl)pyridin-2-amine (51 mg, 0.260 mmol) in the presence of EDCI hydrochloride (90 mg, 0.472 mmol) and DMAP (27 mg, 0.236 mmol) in the mixture of THF and DMF (1:1, 6 mL) to give 25 mg of the product as an off-white solid; $^1$H NMR (300 MHz, DMSO-$d_6$) δ 1.07 (s, 9H), 3.57 (s, 2H), 7.16 (t, J=73.5 Hz, 1H), 7.20-7.46 (m, 3H), 7.53-7.62 (m, 2H), 7.88 (d, J=15.9 Hz, 1H), 8.09 (s, 1H), 8.57 (s, 1H), 8.86 (s, 1H), 11.12 (br s, 1H); APCI-MS (m/z) 601.30 (MH)$^+$.

Example 28

6-{(E)-2-[2-(2,2-Dimethylpropoxy)-3-(difluoromethoxy)phenyl]vinyl}-N-(5,6-dihydro-4H-cyclopenta[d][1,3]thiazol-2-yl)imidazo[2,1-b][1,3]thiazole-5-carboxamide

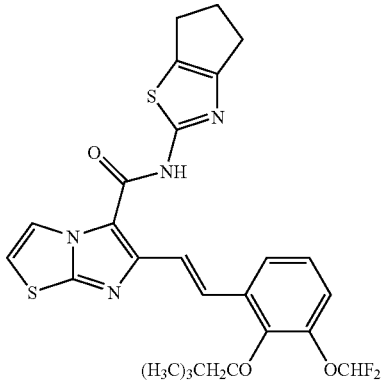

The title compound was prepared according to the general procedure (Method B) by coupling Intermediate 7A (100 mg, 0.236 mmol) with 5,6-dihydro-4H-cyclopenta[d][1,3]thiazol-2-amine (37 mg, 0.260 mmol) in the presence of EDCI hydrochloride (91 mg, 0.472 mmol) and DMAP (26 mg, 0.236 mmol) in a mixture of THF and DMF (1:1, 4 mL) to give 20 mg of the product as an off-white solid; $^1$H NMR (300 MHz, DMSO-$d_6$) δ 1.07 (s, 9H), 2.42-2.52 (m, 2H), 2.75-2.81 (m, 4H), 3.58 (s, 2H), 7.18 (t, J=76.2 Hz, 1H), 7.20-7.28 (m, 2H), 7.38-7.45 (m, 1H), 7.71 (d, J=6.9 Hz, 1H), 7.84 (d, J=15.9 Hz, 1H), 8.05-8.12 (m, 1H), 8.46-8.53 (m, 1H), 13.03 (br s, 1H); APCI-MS (m/z) 545.53 (MH)$^+$.

Example 29

6-{(E)-2-[3-(Difluoromethoxy)-2-(2,2-dimethylpropoxy)phenyl]vinyl}-N-(6-fluoro-1,3-benzothiazol-2-yl)imidazo[2,1-b][1,3]thiazole-5-carboxamide

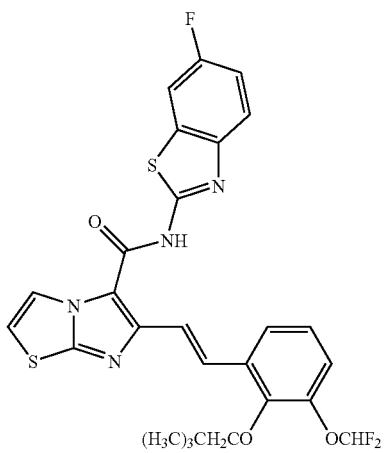

The title compound was prepared according to the general procedure (Method B) by coupling Intermediate 7A (100 mg, 0.236 mmol) with 6-fluoro-1,3-benzothiazol-2-amine (44 mg, 0.260 mmol) in the presence of EDCI hydrochloride (90 mg, 0.472 mmol), DMAP (27 mg, 0.236 mmol) in a mixture of THF and DMF (1:1, 4 mL) to give 15 mg of the product as an off-white solid; $^1$H NMR (300 MHz, DMSO-$d_6$) δ 1.07 (s, 9H), 3.59 (s, 2H), 7.19 (t, J=74.7 Hz, 1H), 7.21-7.28 (m, 1H), 7.32-7.38 (m, 1H), 7.42-7.48 (m, 2H), 7.57-7.62 (m, 1H), 7.70-7.76 (m, 1H), 7.84-7.93 (m, 2H), 8.05-8.12 (m, 1H), 8.47-8.53 (m, 1H), 13.48 (br s, 1H); ESI-MS (m/z) 573.46 (MH)$^+$.

Example 30

N-(2-Cyanoethyl)-6-{(E)-2-[3-(difluoromethoxy)-2-(2,2-dimethylpropoxy)phenyl]vinyl}imidazo[2,1-b][1,3]thiazole-5-carboxamide

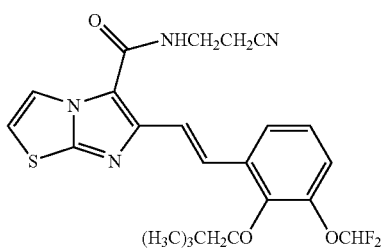

The title compound was prepared according to the general procedure (Method B) by coupling Intermediate 7A (80 mg, 0.189 mmol) with 3-aminopropanenitrile (14.56 mg, 0.208 mmol) in the presence of EDCI hydrochloride (72 mg, 0.378 mmol), DMAP (21 mg, 0.189 mmol) in a mixture of THF and DMF (1:1, 4 mL) to give 60 mg of the product as an off-white solid; $^1$H NMR (300 MHz, DMSO-$d_6$) δ 1.08 (s, 9H), 2.82-2.86 (m, 2H), 3.52-3.60 (m, 4H), 7.16 (t, J=73.5 Hz, 1H), 7.18-7.30 (m, 2H), 7.37-7.52 (m, 2H), 7.72-7.88 (m, 2H), 8.00-8.06 (m, 1H), 8.59 (br s, 1H); APCI-MS (m/z) 475.28 (MH)$^+$.

Example 31

6-{(E)-2-[3-(Difluoromethoxy)-2-(2,2-dimethylpropoxy)phenyl]vinyl}-N-(2,2,2-trifluoroethyl)imidazo[2,1-b][1,3]thiazole-5-carboxamide

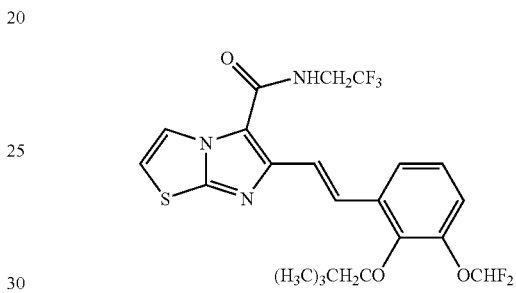

The title compound was prepared according to the general procedure (Method B) by coupling Intermediate 7A (80 mg, 0.189 mmol) with 2,2,2-trifluoroethanamine hydrochloride (28 mg, 0.208 mmol) in the presence of EDCI hydrochloride (72 mg, 0.378 mmol), DMAP (43 mg, 0.378 mmol) in a mixture of THF and DMF (1:1, 4 mL) to give 60 mg of the product as an off-white solid; $^1$H NMR (300 MHz, DMSO-$d_6$) δ 1.07 (s, 9H), 3.57 (s, 2H), 4.10-4.18 (m, 2H), 7.17 (t, J=74.7 Hz, 1H), 7.20 (d, J=7.5 Hz, 2H), 7.39-7.48 (m, 2H), 7.60-7.66 (m, 1H), 7.84 (d, J=15.6 Hz, 1H), 8.00 (s, 1H), 8.85 (br s, 1H); ESI-MS (m/z) 504.22 (MH)$^+$.

Example 32

6-{(E)-2-[3-(Difluoromethoxy)-2-[3-methylbutoxy)phenyl]vinyl}-N-[4-(trifluoromethyl)-1,3-thiazol-2-yl]imidazo[2,1-b][1,3]thiazole-5-carboxamide

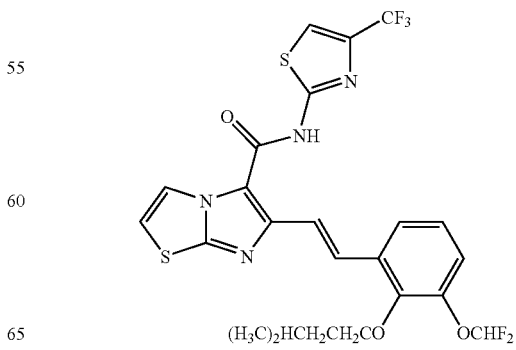

The title compound was prepared according to the general procedure (Method B) by coupling Intermediate 8 (300 mg, 0.710 mmol) with 4-(trifluoromethyl)-1,3-thiazol-2-amine (128 mg, 0.781 mmol) in the presence of EDCI hydrochloride (272 mg, 1.42 mmol), DMAP (80 mg, 0.710 mmol) in a mixture of THF and DMF (1:1, 6 mL) to give 35 mg of the product as an off-white solid; $^1$H NMR (300 MHz, CDCl$_3$) δ 0.86 (d, J=6.6 Hz, 6H), 1.56-1.65 (m, 2H), 1.77-1.86 (m, 1H), 3.95 (t, J=6.3 Hz, 2H), 7.20 (t, J=74.4 Hz, 1H), 7.22-7.30 (m, 2H), 7.46 (s, 1H), 7.57-7.64 (m, 2H), 7.76 (d, J=15.9 Hz, 1H), 8.05-8.12 (m, 2H), 13.03 (br s, 1H); APCI-MS (m/z) 573.23 (MH)$^+$.

Example 33

6-{(E)-2-[3-(Difluoromethoxy)-2-pentyloxy)phenyl]vinyl}-N-(4-trifluoromethyl-1,3-thiazol-2-yl)imidazo[2,1-b][1,3]thiazole-5-carboxamide

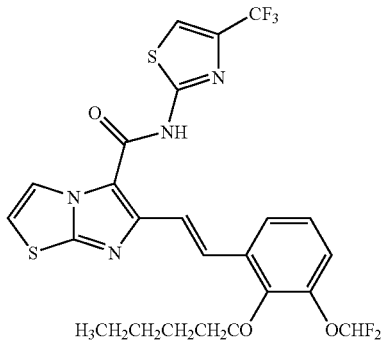

The title compound was prepared according to the general procedure (Method B) by coupling Intermediate 9 (300 mg, 0.711 mmol) with 4-(trifluoromethyl)-1,3-thiazol-2-amine (128 mg, 0.781 mmol) in the presence of EDCI hydrochloride (272 mg, 1.42 mmol), DMAP (80 mg, 0.710 mmol) in a mixture of THF and DMF (1:1, 6 mL) to give 25 mg of the product as an off-white solid; $^1$H NMR (300 MHz, DMSO-d$_6$) δ 0.87 (t, J=6.6 Hz, 3H), 1.20-1.30 (m, 2H), 1.40-1.47 (m, 2H), 1.66-1.76 (m, 2H), 3.90-3.96 (m, 2H), 7.17 (t, J=74.7 Hz, 1H), 7.22-7.28 (m, 2H), 7.45 (s, 1H), 7.57 (d, J=16.2 Hz, 1H), 7.62-7.68 (m, 1H), 7.70 (d, J=15.6 Hz, 1H), 8.05-8.12 (m, 2H), 13.02 (br s, 1H); APCI MS (m/z) 573.25 (MH)$^+$.

Example 34

6-{(E)-2-[3-(Difluoromethoxy)-2-pentyloxy)phenyl]vinyl}-N-(4-cyclopropyl-1,3-thiazol-2-yl)imidazo[2,1-b][1,3]thiazole-5-carboxamide

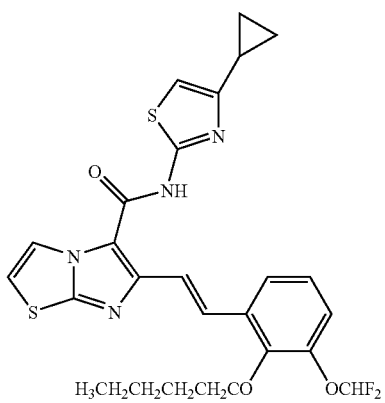

The title compound was prepared according to the general procedure (Method B) by coupling Intermediate 9 (100 mg, 0.236 mmol) with 4-cyclopropyl-1,3-thiazol-2-amine (36 mg, 0.260 mmol) in the presence of EDCI hydrochloride (90 mg, 0.472 mmol) and DMAP (26 mg, 0.236 mmol) in a mixture of THF and DMF (1:1, 4 mL) to give 33 mg of the product as an off-white solid; $^1$H NMR (300 MHz, DMSO-d$_6$) δ 0.78-0.83 (m, 2H), 0.87-0.95 (m, 5H), 1.30-1.37 (m, 2H), 1.42-1.50 (m, 2H), 1.72-1.78 (m, 2H), 1.94-2.00 (m, 1H), 3.90-3.96 (m, 2H), 6.58-6.66 (m, 1H), 7.19 (t, J=73.5 Hz, 1H), 7.21-7.30 (m, 1H), 7.38-7.46 (m, 1H), 7.66 (d, J=7.5 Hz, 1H), 7.79 (d, J=15.6 Hz, 1H), 8.05-8.14 (m, 2H), 8.50-8.60 (m, 1H), 12.99 (br s, 1H); APCI-MS (m/z) 545.17 (MH)$^+$.

Example 35

6-{(E)-2-[2-(Cyclobutylmethoxy)-3-(difluoromethoxy)phenyl]vinyl}-N-(4-cyclopropyl-1,3-thiazol-2-yl)imidazo[2,1-b][1,3]thiazole-5-carboxamide

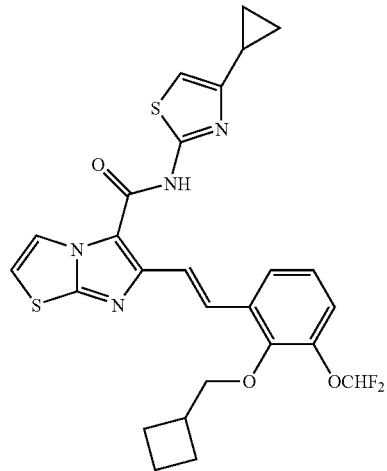

The title compound was prepared according to the general procedure (Method B) by coupling Intermediate 10 (200 mg, 0.476 mmol) with 4-cyclopropyl-1,3-thiazol-2-amine (73 mg, 0.523 mmol) in the presence of EDCI hydrochloride (182 mg, 0.952 mmol) and DMAP (53 mg, 0.476 mmol) in a mixture of THF and DMF (1:1, 4 mL) to give 120 mg of the product as an off-white solid; $^1$H NMR (300 MHz, CDCl$_3$) δ 0.80-0.86 (m, 2H), 0.88-0.96 (m, 2H), 1.23-1.29 (m, 1H), 1.85-1.94 (m, 4H), 2.00-2.10 (m, 2H), 2.72-2.80 (m, 1H), 3.98 (d, J=6.6 Hz, 2H), 6.36 (s, 1H), 6.58 (t, J=75.3 Hz, 1H), 6.95 (d, J=4.5 Hz, 1H), 7.00-7.10 (m, 2H), 7.48-7.53 (m, 1H), 7.62 (d, J=15.6 Hz, 1H), 7.82 (d, J=15.6 Hz, 1H), 8.24-8.30 (m, 1H); APCI-MS (m/z) 543.31 (MH)$^+$.

Example 36

6-{(E)-2-[2-(Cyclobutylmethoxy)-3-(difluoromethoxy)phenyl]vinyl}-N-[4-(trifluoro-methyl)-1,3-thiazol-2-yl]imidazo[2,1-b][1,3]thiazole-5-carboxamide

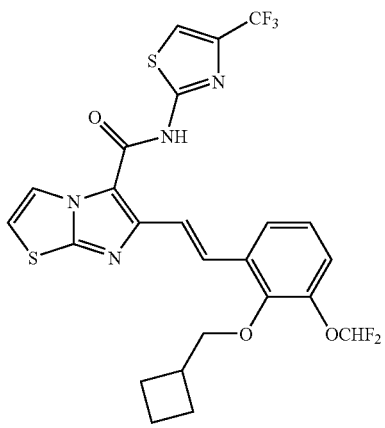

The title compound was prepared according to the general procedure (Method B) by coupling Intermediate 10 (300 mg, 0.714 mmol) with 4-(trifluoromethyl)-1,3-thiazol-2-amine (128 mg, 0.785 mmol) in the presence of EDCI hydrochloride (273 mg, 1.428 mmol), DMAP (80 mg, 0.714 mmol) in a mixture of THF and DMF (1:1, 6 mL) to give 27 mg of the product as an off-white solid; $^1$H NMR (300 MHz, CDCl$_3$) δ 1.80-1.90 (m, 4H), 1.98-2.08 (m, 2H), 2.66-2.76 (m, 1H), 3.89-3.95 (m, 2H), 7.15-7.25 (m, 3H), 7.40-7.47 (m, 1H), 7.52-7.67 (m, 2H), 7.78 (d, J=15.9 Hz, 1H), 8.00-8.10 (m, 2H), 13.03 (br s, 1H); APCI-MS (m/z) 571.18 (MH)$^+$.

Example 37

2-{(E)-2-[2-(2,2-Dimethylpropoxy)-3-methoxyphenyl]vinyl}-N-[4-(trifluoromethyl)-1,3-thiazol-2-yl]imidazo[1,2-c]pyridine-3-carboxamide

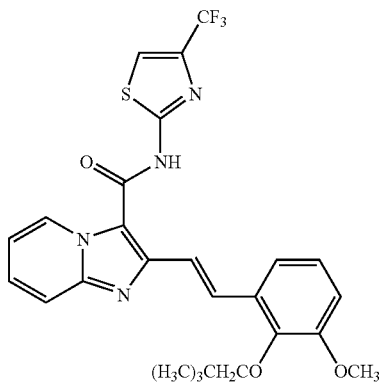

The title compound was prepared according to the general procedure (Method B) by coupling Intermediate 11 (150 mg, 0.394 mmol) with 4-(trifluoromethyl)-1,3-thiazol-2-amine (77 mg, 0.473 mmol) in the presence of EDCI hydrochloride (150 mg, 0.788 mmol) and DMAP (72 mg, 0.591 mmol) in a mixture of DCM and DMF (4:1, 10 mL) to give 40 mg of the product as an off-white solid; $^1$H NMR (300 MHz, DMSO-d$_6$) δ 1.00 (s, 9H), 3.57 (s, 2H), 3.81 (s, 3H), 7.03 (d, J=7.8 Hz, 1H), 7.09-7.12 (m, 2H), 7.34 (d, J=7.8 Hz, 1H), 7.51-7.56 (m, 2H), 7.69 (d, J=9.3 Hz, 1H), 7.99 (d, J=16.2 Hz, 1H), 8.07 (s, 1H), 8.89 (d, J=6.9 Hz, 1H), 13.11 (s, 1H); ESI-MS (m/z) 531.19 (MH)$^+$.

Example 38

2-{(E)-2-[3-(Difluoromethoxy)-2-(2,2-dimethylpropoxy)phenyl]vinyl}-N-[4-(trifluoro-methyl)-1,3-thiazol-2-yl]imidazo[1,2-c]pyridine-3-carboxamide

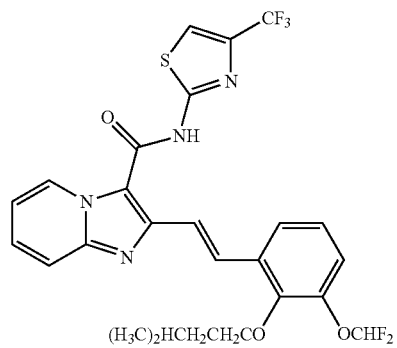

The title compound was prepared according to the general procedure (Method B) by coupling Intermediate 13 (150 mg, 0.360 mmol) with 4-(trifluoromethyl)-1,3-thiazol-2-amine (70 mg, 0.432 mmol) in the presence of EDCI hydrochloride (137 mg, 0.720 mmol) and DMAP (66 mg, 0.540 mmol) in a mixture of DCM and DMF (4:1, 5 mL) to give 30 mg of the product as an off-white solid; $^1$H NMR (300 MHz, CDCl$_3$) δ 1.06 (s, 9H), 3.58 (s, 2H), 7.12 (t, J=6.9 Hz, 1H), 7.18 (t, J=74.1 Hz, 1H), 7.21-7.30 (m, 2H), 7.40-7.54 (m, 2H), 7.62-7.71 (m, 3H), 7.97 (d, J=15.6 Hz, 1H), 8.85-8.93 (m, 1H), 13.13 (br s, 1H); APCI-MS (m/z) 567.22 (MH)$^+$.

Example 39

2-{(E)-2-[2-(2,2-Dimethylpropoxy)-3-(difluoromethoxy)phenyl]vinyl}-N-(4-cyclo-propyl-1,3-thiazol-2-yl)imidazo[1,2-a]pyridine-3-carboxamide

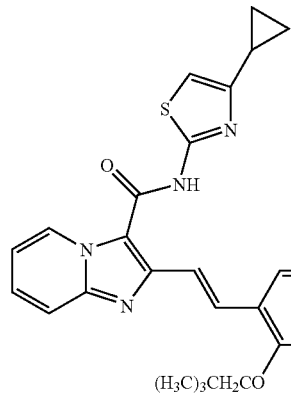

The title compound was prepared according to the general procedure (Method B) by coupling Intermediate 13 (100 mg, 0.240 mmol) with 4-cyclopropyl-1,3-thiazol-2-amine (37 mg, 0.264 mmol) in the presence of EDCI hydrochloride (91 mg, 0.480 mmol) and DMAP (27 mg, 0.240 mmol) in a mixture of THF and DMF (1:1, 4 mL) to give 35 mg of the product as an off-white solid; $^1$H NMR (300 MHz, CDCl$_3$) δ

0.79-0.85 (m, 2H), 1.05 (s, 9H), 1.20-1.26 (m, 2H), 1.95-2.01 (m, 1H), 3.58 (d, J=5.4 Hz, 2H), 6.60-6.71 (m, 1H), 6.90-6.98 (m, 1H), 7.10-7.27 (m, 3H), 7.38-7.46 (m, 1H), 7.50-7.56 (m, 2H), 7.63-7.70 (m, 1H), 7.92 (d, J=15.6 Hz, 1H), 7.99 (d, J=15.0 Hz, 1H), 13.03 (br s, 1H); APCI-MS (m/z) 539.45 (MH)$^+$.

Example 40

N-(4-Cyclobutyl-1,3-thiazol-2-yl)-2-{(E)-2-[3-(difluoromethoxy)-2-(2,2-dimethyl-propoxy)phenyl]vinyl}imidazo[1,2-c]pyridine-3-carboxamide

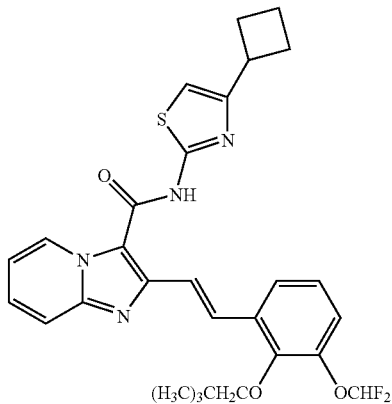

The title compound was prepared according to the general procedure (Method B) by coupling Intermediate 13 (100 mg, 0.240 mmol) with 4-cyclobutyl-1,3-thiazol-2-amine (41 mg, 0.264 mmol) in the presence of EDCI hydrochloride (91 mg, 0.480 mmol) and DMAP (27 mg, 0.240 mmol) in a mixture of THF and DMF (1:1, 4 mL) to give 40 mg of the product as an off-white solid; $^1$H NMR (300 MHz, DMSO-d$_6$) δ 1.06 (s, 9H), 1.95-2.04 (m, 2H), 2.17-2.28 (m, 4H), 3.50-3.56 (m, 1H), 3.59 (s, 2H), 6.75-6.85 (m, 1H), 7.02-7.10 (m, 1H), 7.19 (t, J=74.7 Hz, 1H), 7.21-7.27 (m, 2H), 7.43-7.50 (m, 2H), 7.60-7.65 (m, 1H), 7.69-7.75 (m, 1H), 7.98-8.05 (m, 1H), 9.68-9.75 (m, 1H), 12.94 (br s, 1H); APCI-MS (m/z) 553.38 (MH)$^+$.

Example 41

2-{(E)-2-[3-(Difluoromethoxy)-2-(3-methylbutoxy)phenyl]vinyl}-N-[4-(trifluoromethyl)-1,3-thiazol-2-yl]imidazo[1,2-c]pyridine-3-carboxamide

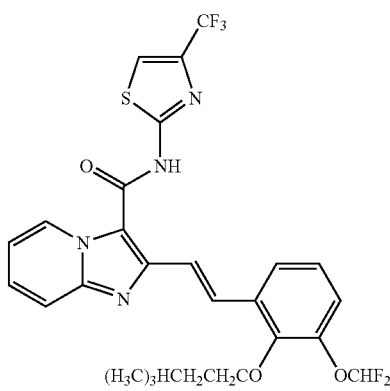

The title compound was prepared according to the general procedure (Method B) by coupling Intermediate 14 (200 mg, 0.480 mmol) with 4-(trifluoromethyl)-1,3-thiazol-2-amine (97 mg, 0.576 mmol) in the presence of EDCI hydrochloride (184 mg, 0.96 mmol) and DMAP (81 mg, 0.72 mmol) in the mixture of DCM and DMF (1:1, 4 mL) to give 25 mg of the product as an off-white solid; $^1$H NMR (300 MHz, DMSO-d$_6$) δ 0.85 (d, J=6.6 Hz, 6H), 1.57-1.63 (m, 2H), 1.79-1.85 (m, 1H), 3.95-4.01 (m, 2H), 7.10-7.15 (m, 1H), 7.21 (t, J=74.1 Hz, 1H), 7.22-7.30 (m, 1H), 7.40-7.46 (m, 1H), 7.50-7.56 (m, 1H), 7.63-7.72 (m, 3H), 7.92 (d, J=15.6 Hz, 1H), 8.06-8.12 (m, 1H), 8.86-8.92 (m, 1H), 13.15 (br s, 1H); APCI-MS (m/z) 567.24 (MH)$^+$.

Pharmacological Activity

Certain illustrative compounds within the scope of the present invention are screened for TRPV3 activity according to a modified procedure described in (a) Tóth, A. et al. *Life Sciences* 2003, 73, 487-498. (b) McNamara C, R. et al. *Proc. Natl. Acad. Sci. U.S.A.*, 2007, 104, 13525-13530. The screening of the compounds may be carried out by other methods and procedures known to persons skilled in the art.

Screening for TRPV3 Antagonist Using the $^{45}$Calcium Uptake Assay

The inhibition of TRPV3 receptor activation was followed as inhibition of 2-aminoethxydiphenylborate (2-APB) induced cellular uptake of radioactive calcium. Test compounds were dissolved in dimethyl sulfoxide (DMSO) to prepare 20 mM stock solution and then diluted using plain medium with DMEM/F-12 containing 1.8 mM CaCl$_2$ to get desired concentration. Final concentration of DMSO in the reaction was 0.5% (v/v). Human TRPV3 expressing CHO cells were grown in DMEM/F-12 medium with 10% FBS, 1% penicillin-streptomycin solution, 400 µg/mL of G-418. Cells were seeded 24 h prior to the assay in 96 well plates so as to get ~50,000 cells per well on the day of experiment. Cells were treated with test compounds for 10 minutes followed by addition of 2-APB at a final concentration of 500 µM and 5 µCi/mL $^{45}$Ca$^{+2}$ for 4 minutes. Cells were washed and lysed using buffer containing 1% Triton X-100, 0.1% deoxycholate and 0.1% SDS. Radioactivity in the lysate was measured in Packardt Top count after addition of liquid scintillant. Concentration response curves were plotted as a % of maximal response obtained in the absence of test antagonist. IC$_{50}$ value was calculated from concentration response curve by nonlinear regression analysis using GraphPad PRISM software.

The compounds prepared were tested using the above assay procedure and the results obtained are given in Table 1. Percentage inhibition at concentrations of 1.0 µM and 10.0 µM are given in the table along with IC$_{50}$ (nM) details for selected examples. The IC$_{50}$ (nM) values of the compounds are set forth in Table 1 wherein "A" refers to an IC$_{50}$ value of less than 100 nM, "B" refers to IC$_{50}$ value in range of 100.01 to 250.0 nM and "C" refers to an IC$_{50}$ value in range of 250.01 to 1000.0 nM.

TABLE 1

In-vitro screening results of compounds of invention

| Examples | Percentage inhibition | | IC$_{50}$ (nM) |
|---|---|---|---|
| | at 1.0 µM | at 10.0 µM | |
| Example 1 | 9.30 | 38.61 | — |
| Example 2 | 73.21 | 97.56 | C |
| Example 3 | 34.62 | 90.60 | — |

TABLE 1-continued

In-vitro screening results of compounds of invention

| Examples | Percentage inhibition at 1.0 µM | Percentage inhibition at 10.0 µM | IC$_{50}$ (nM) |
|---|---|---|---|
| Example 4 | 36.17 | 91.73 | — |
| Example 5 | 5.32 | 38.23 | — |
| Example 6 | 93.02 | 98.75 | C |
| Example 7 | 95.50 | 99.51 | A |
| Example 8 | 88.08 | 91.11 | A |
| Example 9 | NA | NA | A |
| Example 10 | 69.32 | 80.56 | C |
| Example 11 | 75.07 | 84.79 | A |
| Example 12 | 13.28 | 82.79 | — |
| Example 13 | 10.75 | 31.51 | — |
| Example 14 | 10.33 | 15.45 | — |
| Example 15 | 20.71 | 26.57 | — |
| Example 16 | 81.71 | 93.09 | C |
| Example 17 | 85.34 | 94.61 | C |
| Example 18 | 96.94 | 98.19 | A |
| Example 19 | 13.94 | 4.88 | — |
| Example 20 | 53.30 | 81.72 | — |
| Example 21 | 80.76 | 89.85 | B |
| Example 22 | 47.87 | 86.53 | — |
| Example 23 | 93.15 | 90.04 | A |
| Example 24 | 22.47 | 37.27 | — |
| Example 25 | 0 | 18.18 | — |
| Example 26 | 70.10 | 77.49 | — |
| Example 27 | 25.71 | 33.94 | — |
| Example 28 | 9.45 | 15.56 | — |
| Example 29 | 23.97 | 15.35 | — |
| Example 30 | 21.09 | 94.02 | — |
| Example 31 | 60.89 | 97.72 | — |
| Example 32 | 63.71 | 96.62 | — |
| Example 33 | 51.77 | 93.11 | — |
| Example 34 | 78.13 | 94.95 | B |
| Example 35 | 84.27 | 96.45 | A |
| Example 36 | 93.72 | 97.72 | B |
| Example 37 | 94.91 | 97.88 | A |
| Example 38 | 87.67 | 97.11 | A |
| Example 39 | 76.08 | 58.73 | — |
| Example 40 | 56.41 | 72.35 | — |
| Example 41 | 52.99 | 84.65 | — |

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as described above.

All publications, patents, and patent applications cited in this application are herein incorporated by reference to the same extent as if each individual publication, patent, or patent application was specifically and individually indicated to be incorporated herein by reference.

The invention claimed is:

1. The compound having the formula (II):

(II)

wherein X is CR$^1$; and Y is S;
R$^1$ is hydrogen;
R$^3$ is hydrogen, alkali (including lithium, sodium, or potassium), or substituted or unsubstituted alkyl;
R$^4$ is substituted or unsubstituted alkyl, haloalkyl, cyanoalkyl, aryl, heteroaryl, heterocyclyl; or R$^3$ and R$^4$, together with the nitrogen atom to which they are attached, may form an optionally substituted 4 to 12 membered cyclic ring; which cyclic ring may be heterocyclyl or heteroaryl; and
R$^a$ and R$^b$, which may be same or different, are each independently hydrogen, substituted or unsubstituted alkyl, haloalkyl, cyanoalkyl, cycloalkyl, cycloalkylalkyl or alkoxyalkyl;
or pharmaceutically acceptable salt thereof.

2. The compound of claim 1, wherein R$^a$ is alkyl.
3. The compound of claim 2, wherein alkyl is n-pentyl.
4. The compound of claim 2, wherein alkyl is neo-pentyl.
5. The compound of claim 1, wherein R$^a$ is cycloalkylalkyl.
6. The compound of claim 5, wherein cycloalkylalkyl is cyclobutylmethyl.
7. The compound of claim 1, wherein R$^b$ is alkyl.
8. The compound of claim 7, wherein alkyl methyl.
9. The compound of claim 1, wherein R$^b$ is haloalkyl.
10. The compound of claim 9, wherein haloalkyl is difluoromethyl.
11. The compound of claim 1, wherein R$^3$ is hydrogen.
12. The compound of claim 1, wherein R$^3$ is alkali.
13. The compound of claim 12, wherein alkalimetal is sodium or potassium.
14. The compound of claim 1, wherein R$^4$ is heteroaryl.
15. The compound of claim 14, wherein heteroaryl is substituted thiazole.
16. The compound of claim 15, wherein substituent(s) on thiazole is trifluoromethyl, tent-butyl, or cyclopropyl.
17. A compound of claim 1, which is:
6-[(E)-2-(2-Cyclopropylmethoxy-3-methoxyphenyl)vinyl]-N-[4-(trifluoromethoxy)phenyl]imidazo[2,1-b][1,3]thiazole-5-carboxamide;
6-[(E)-2-(2-Cyclopropylmethoxy-3-methoxyphenyl)vinyl]-N-[4-(trifluoromethyl)-1,3-thiazol-2-yl]imidazo[2,1-b][1,3]thiazole-5-carboxamide;
1-({6-[(E)-2-(2-Cyclopropylmethoxy-3-methoxyphenyl)vinyl]imidazo[2,1-b][1,3]thiazol-5-yl}carbonyl)-1,2,3,4-tetrahydroquinoline;
6-[(E)-2-(2-Cyclopropylmethoxy-3-methoxyphenyl)vinyl]imidazo[2,1-b][1,3]thiazol-5-yl-4-(5-trifluoromethyl-2-pyridyl)piperazinomethanone;
6-(4-{6-(E)-2-(2-Cyclopropylmethoxy-3-methoxyphenyl)-1-ethenyl]imidazo[2,1-b][1,3]thiazol-5-ylcarbonyl}piperazino)nicotinonitrile;
6-{(E)-2-[2-(Isobutoxy)-3-methoxyphenyl]vinyl}-N-[4-(trifluoromethyl)-1,3-thiazol-2-yl]imidazo[2,1-b][1,3]thiazole-5-carboxamide;
6-{(E)-2-[2-(2,2-Dimethylpropoxy)-3-methoxyphenyl]vinyl}-N-[4-(trifluoromethyl)-1,3-thiazol-2-yl]imidazo[2,1-b][1,3]thiazole-5-carboxamide;
6-{(E)-2-[2-(2,2-Dimethylpropoxy)-3-methoxyphenyl]vinyl}-N-[4-(tert-butyl)-1,3-thiazol-2-yl]imidazo[2,1-b][1,3]thiazole-5-carboxamide;
6-{(E)-2-[2-(2,2-Dimethylpropoxy)-3-methoxyphenyl]vinyl}-N-[4-(tert-butyl)-1,3-thiazol-2-yl]imidazo[2,1-b][1,3]thiazole-5-carboxamide sodium salt;
6-{(E)-2-[2-(2,2-Dimethylpropoxy)-3-methoxyphenyl]vinyl}-N-(4-methyl-1,3-thiazol-2-yl)imidazo[2,1-b][1,3]thiazole-5-carboxamide;

N-Ethyl-6-{(E)-2-[2-(2,2-dimethylpropoxy)-3-methoxyphenyl]vinyl}-N-[4-(trifluoromethyl)-1,3-thiazol-2-yl]imidazo[2,1-b][1,3]thiazole-5-carboxamide;

6-{(E)-2-[2-(2,2-Dimethylpropoxy)-3-methoxyphenyl]vinyl}-N-[5-(trifluoromethyl)-1,3,4-thiadiazol-2-yl]imidazo[2,1-b][1,3]thiazole-5-carboxamide;

6-{[(E)-2-(2,2-Dimethylpropoxy)-3-methoxyphenyl]vinyl}-N-[4-(trifluoromethyl)-1,3-oxazol-2-yl]imidazo[2,1-b][1,3]thiazole-5-carboxamide;

6-[(E)-2-(2,2-Dimethylpropoxy)-3-methoxyphenyl)vinyl]imidazo[2,1-b][1,3]thiazol-5-yl-3-trifluoromethyl-5,6,7,8-tetrahydro[1,2,4]triazolo[4,3-a]pyrazin-7-yl-methanone;

N-[4-(4-Cyanophenyl)-1,3-thiazol-2-yl]-6-{(E)-2-[2-(2,2-dimethylpropoxy)-3-methoxyphenyl]vinyl}imidazo[2,1-b][1,3]thiazole-5-carboxamide;

6-[(E)-2-(2-Cyclopentyloxy-3-methoxyphenyl)vinyl]-N-[4-(trifluoromethyl)-1,3-thiazol-2-yl]imidazo[2,1-b][1,3]thiazole-5-carboxamide;

6-{(E)-2-[2-Cyclopentyloxy-3-(difluoromethoxy)phenyl]vinyl}-N-[4-(trifluoromethyl)-1,3-thiazol-2-yl]imidazo[2,1-b][1,3]thiazole-5-carboxamide;

6-{(E)-2-[3-Difluoromethoxy-2-(2,2-dimethylpropoxy)phenyl]vinyl}-N-[4-(trifluoromethyl)-1,3-thiazol-2-yl]imidazo[2,1-b][1,3]thiazole-5-carboxamide;

6-[(E)-2-(2,3-Dihydroxyphenyl)vinyl]-N-[4-(trifluoromethyl)-1,3-thiazol-2-yl]imidazo[2,1-b][1,3]thiazole-5-carboxamide;

6-{(E)-2-[2-(2,2-Dimethylpropoxy)-3-(difluoromethoxy)phenyl]vinyl}-N-(4-isopropyl-1,3-thiazol-2-yl)imidazo[2,1-b][1,3]thiazole-5-carboxamide;

6-[(E)-2-(3-(Difluoromethoxy)-2-(2,2-dimethylpropoxy)-phenyl)vinyl]-N-(4-tert-butyl-1,3-thiazol-2-yl)imidazo[2,1-b][1,3]thiazole-5-carboxamide;

6-{(E)-2-[2-(2,2-Dimethylpropoxy)-3-(difluoromethoxy)phenyl]vinyl}-N-(4-cyclobutyl-1,3-thiazol-2-yl)imidazo[2,1-b][1,3]thiazole-5-carboxamide;

6-{(E)-2-[2-(2,2-Dimethylpropoxy)-3-(difluoromethoxy)phenyl]vinyl}-N-(4-cyclopropyl-1,3-thiazol-2-yl)imidazo[2,1-b][1,3]thiazole-5-carboxamide;

6-{(E)-2-[3-(Difluoromethoxy)-2-(2,2-dimethylpropoxy)phenyl]vinyl}-N-(3-trifluoromethylphenyl)imidazo[2,1-b][1,3]thiazole-5-carboxamide;

6-{(E)-2-[3-(Difluoromethoxy)-2-(2,2-dimethylpropoxy)phenyl]vinyl}-N-(3-trifluoromethylbenzyl)imidazo[2,1-b][1,3]thiazole-5-carboxamide;

N-(5-Cyanopyridin-2-yl)-6-{(E)-2-[3-(difluoromethoxy)-2-(2,2-dimethylpropoxy)phenyl]vinyl}imidazo[2,1-b][1,3]thiazole-5-carboxamide;

N-[3-Chloro-5-(trifluoromethyl)pyridin-2-yl]-6-{(E)-2-[3-(difluoromethoxy)-2-(2,2-dimethylpropoxy)phenyl]vinyl}imidazo[2,1-b][1,3]thiazole-5-carboxamide;

6-{(E)-2-[2-(2,2-Dimethylpropoxy)-3-(difluoromethoxy)phenyl]vinyl}-N-(5,6-dihydro-4H-cyclopenta[d][1,3]thiazol-2-yl)imidazo[2,1-b][1,3]thiazole-5-carboxamide;

6-{(E)-2-[3-(Difluoromethoxy)-2-(2,2-dimethylpropoxy)phenyl]vinyl}-N-(6-fluoro-1,3-benzothiazol-2-yl)imidazo[2,1-b][1,3]thiazole-5-carboxamide;

N-(2-Cyanoethyl)-6-{(E)-2-[3-(difluoromethoxy)-2-(2,2-dimethylpropoxy)phenyl]vinyl}imidazo[2,1-b][1,3]thiazole-5-carboxamide;

6-{(E)-2- [3-(Difluoromethoxy)-2-(2,2dimethylpropoxy)phenyl]vinyl}-N-(2,2,2-trifluoroethyl) imidazo[2,1-b][1,3]thiazole-5-carboxamide;

6-{(E)-2- [3-(Difluoromethoxy)-2-(3 -methylbutoxy)phenyl]vinyl}-N-[4-(trifluoromethyl)-1,3-thiazol-2-yl]imidazo [2,1-b][1,3]thiazole-5-carboxamide;

6-{(E)-2-[3-(Difluoromethoxy)-2-pentyloxy)phenyl]vinyl}-N-(4-trifluoromethyl- 1,3-thiazol-2-yl) imidazo[2,1-b][1,3]thiazole-5 -carboxamide;

6-{(E)-2-[3-(Difluoromethoxy)-2-pentyloxy)phenyl]vinyl}-N-(4-cyclopropyl-1,3-thiazol-2-yl) imidazo [2,1-b][1,3]thiazole-5 -carboxamide;

6-{(E)-2-[2-(Cyclobutylmethoxy)-3-(difluoromethoxy)phenyl]vinyl}-N-(4-cyclopropyl-1,3-thiazol-2-yl)imidazo [2,1-b][1,3]thiazole-5 -carboxamide;

6-{(E)-2-[2-(Cyclobutylmethoxy)-3-(difluoromethoxy)phenyl]vinyl}-N-[4-(trifluoromethyl)-1,3-thiazol-2yl] limidazo [2,1-b][1,3]thiazole-5-carboxamide;

or pharmaceutically acceptable salts thereof.

18. The compounds of claim 1, or pharmaceutically acceptable salts thereof, that possess IC50 of less 100 nM as measured by a $^{45}$Calcium uptake assay.

19. 6-55 (E)-2-[3-Difluoromethoxy-2-(2,2-dimethylpropoxy)phenyl]vinyl}-N-[4-(trifluoro-methyl)-1,3-thiazol-2-yl]imidazo[2,1-b][1,3]thiazole-5-carboxamide, or pharmaceutically acceptable salt thereof.

20. A pharmaceutical composition comprising a compound according to claims 19 either as a free base or pharmaceutically acceptable salt form and a pharmaceutically acceptable excipient.

* * * * *